(12) United States Patent
Guzov et al.

(10) Patent No.: US 7,655,838 B2
(45) Date of Patent: Feb. 2, 2010

(54) **INSECT INHIBITORY *BACILLUS THURINGIENSIS* PROTEINS, FUSIONS, AND METHODS OF USE THEREFOR**

(75) Inventors: Victor M. Guzov, Manchester, MO (US); Thomas M. Malvar, Troy, MO (US); James K. Roberts, Chesterfield, MO (US); Sakuntala Sivasupramaniam, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 179 days.

(21) Appl. No.: 11/796,742

(22) Filed: Apr. 27, 2007

(65) Prior Publication Data

US 2007/0208168 A1    Sep. 6, 2007

Related U.S. Application Data

(62) Division of application No. 10/380,077, filed as application No. PCT/US01/28746 on Sep. 12, 2001, now Pat. No. 7,214,788.

(60) Provisional application No. 60/232,099, filed on Sep. 12, 2000.

(51) Int. Cl.
*A01H 5/00*     (2006.01)
*C12N 15/82*    (2006.01)
*C12N 15/32*    (2006.01)

(52) U.S. Cl. .............. 800/302; 800/279; 435/418; 435/320.1; 435/468; 536/23.71

(58) Field of Classification Search .............. None
See application file for complete search history.

(56) References Cited

U.S. PATENT DOCUMENTS

| | | | |
|---|---|---|---|
| 6,037,522 A | 3/2000 | Dong et al. | 800/287 |
| 6,063,756 A | 5/2000 | Donovan et al. | 514/2 |
| 6,083,499 A | 7/2000 | Narva et al. | 424/93 |

FOREIGN PATENT DOCUMENTS

| | | |
|---|---|---|
| EP | 0382990 A1 | 8/1990 |
| WO | WO 91/01087 A | 2/1991 |
| WO | WO 98/13498 A | 4/1998 |
| WO | WO 99/31248 A | 6/1999 |
| WO | WO 00/66742 | 11/2000 |
| WO | WO 01/14417 A2 | 3/2001 |

*Primary Examiner*—Anne Kubelik
(74) *Attorney, Agent, or Firm*—Timothy K. Ball, Esq.; Howrey LLP

(57) ABSTRACT

Novel insect inhibitory proteins are disclosed comprising two different components, both of which are required for biological activity. Various methods of linking both components together, so that a single protein provides insect inhibitory activity, are disclosed. Also disclosed are novel *Bacillus thuringiensis* nucleic acid sequences encoding Coleopteran-inhibitory crystal proteins, designated tIC100 (29-kDa) and tIC101 (14-kDa). Also disclosed are methods of making and using nucleic acid sequences in the development of the transgenic plant cells containing the novel nucleic acid sequences disclosed herein.

25 Claims, 1 Drawing Sheet

INSECT INHIBITORY *BACILLUS THURINGIENSIS* PROTEINS, FUSIONS, AND METHODS OF USE THEREFOR

CROSS REFERENCE TO RELATED APPLICATION

This application is a divisional of U.S. patent application Ser. No. 10/380,077, filed Mar. 7, 2003, now U.S. Pat. No. 7,214,788 which is a §371 U.S. National phase application of International Application No. PCT/US01/28746 filed Sep. 12, 2001 and claims the benefit of priority to U.S. Provisional Application No. 60/232,099, filed Sep. 12, 2000. All of the above priority documents are incorporated herewith by reference in their entirety.

BACKGROUND OF THE INVENTION

1. Field of the Invention

The present invention relates generally to the field of molecular biology. More particularly, the present invention concerns a new class of insect inhibitory proteins comprising two different components, both of which are required for biological activity. The present invention concerns the construction of coleopteran-inhibitory crystal proteins, in particular CryET33/CryET34 and tIC100/tIC101 from *Bacillus thuringiensis*. Various methods of linking the proteins together, so that a single protein provides insect inhibitory activity, are disclosed. The use of nucleic acid sequences as diagnostic probes and templates for protein synthesis, and the use of polypeptides, fusion proteins, antibodies, and peptide fragments in various insect inhibitory, immunological, and diagnostic applications are also disclosed, as are methods of making and using nucleic acid sequences in the development of transgenic plant cells containing the nucleic acid sequences disclosed herein.

2. Description of the Related Art

Environmentally-sensitive methods for controlling or eradicating insect infestation are desirable in many instances, in particular when crops of commercial interest are at issue. The most widely used environmentally-sensitive insect inhibitory formulations developed in recent years have been composed of microbial pest control agents derived from the bacterium *Bacillus thuringiensis*. *B. thuringiensis* is well known in the art, and is characterized morphologically as a Gram-positive bacterium that produces crystal proteins or inclusion bodies which are aggregations of proteins specifically active against certain orders and species of insects. Many different strains of *B. thuringiensis* have been shown to produce insect inhibitory crystal proteins. Compositions including *B. thuringiensis* strains which produce insect inhibitory proteins have been commercially available and used as environmentally-acceptable pest control agents because they are quite toxic to the specific target insect, but are harmless to plants and other non-targeted organisms.

There are several B.t. crystal protein categories established based on primary structure information and the degree of protein similarities to one another. Over the past decade, research on the structure and function of *B. thuringiensis* crystal proteins has covered all of the major categories, and while these proteins differ in specific structure and function, general similarities in the structure and function are assumed. Based on the accumulated knowledge of *B. thuringiensis* insect inhibitory proteins, a generalized mode of action for *B. thuringiensis* insect inhibitory proteins has been created and includes: ingestion by the insect, solubilization in the insect midgut (a combination of stomach and small intestine), resistance to digestive enzymes sometimes with partial digestion actually "activating" the insect inhibitory protein, binding to the midgut cells, formation of a pore in the insect cells and the disruption of cellular homeostasis (English and Slatin, 1992).

Many of the δ-endotoxins are related to various degrees by similarities in their amino acid sequences. Historically, the proteins and the genes which encode them were classified based largely upon their spectrum of insect inhibitory activity. The review by Schnepf et al. (Microbiol. Mol. Biol. Rev. (1998) 62:775-806) discusses the genes and proteins that were identified in *B. thuringiensis* prior to 1998, and sets forth the most recent nomenclature and classification scheme as applied to *B. thuringiensis* insect inhibitory genes and proteins. Using older nomenclature classification schemes, cry1 genes were deemed to encode lepidopteran-inhibitory Cry1 proteins, cry2 genes were deemed to encode lepidopteran- and dipteran-inhibitory Cry2 proteins, cry3 genes were deemed to encode coleopteran-inhibitory Cry3 proteins, and cry4 genes were deemed to encode dipteran-inhibitory Cry4 proteins. However, new nomenclature systematically classifies the Cry proteins based upon amino acid sequence homology rather than upon insect target specificities. The classification scheme for many known proteins, not including allelic variations in individual proteins, including dendograms and full *Bacillus thuringiensis* protein lists is summarized and regularly updated at http://epunix.biols.susx.ac.uk/Home/Nil_Crickmore/Bt/index.html.

Most of the nearly 200 B.t. crystal proteins presently known have some degree of lepidopteran activity associated with them. The large majority of *Bacillus thuringiensis* insect inhibitory proteins which have been identified do not have coleopteran controlling activity. Therefore, it is particularly important, at least for commercial purposes, to identify additional coleopteran specific insect inhibitory proteins.

The B.t. proteins which have been identified as having coleopteran-inhibitory activity are either related to the Cry3 protein class, or are greater than about 74 kDa in size. (Berhnard, 1986; Donovan et al., 1988, 1992; Herrnstadt et al., 1986; Hofte et al., 1987, 1989; Kreig et al., 1983, 1984, 1987; McPherson et al., 1988; Sekar et al., 1987; Sick et al., 1990; U.S. Pat. No. 4,766,203; U.S. Pat. No. 4,771,131; U.S. Pat. No. 4,797,279; U.S. Pat. No. 4,910,016; U.S. Pat. No. 4,966,155; U.S. Pat. No. 4,966,765; U.S. Pat. No. 4,999,192; U.S. Pat. No. 5,006,336; U.S. Pat. No. 5,024,837; U.S. Pat. No. 5,055,293; U.S. Pat. No. 6,023,013; European Pat. Appl. Publ. No. 0318143; Eur. Pat. Appl. Publ. No. 0324254; Eur. Pat. Appl. Publ. No. 0382990; PCT Intl. Pat. Appl. Publ. No. WO 90/13651; Intl. Pat. Appl. Publ. No. WO 91/07481).

U.S. Pat. No. 6,063,756 disclosed *Bacillus thuringiensis* strains comprising novel crystal proteins which exhibit insect inhibitory activity against coleopteran insects including red flour beetle larvae (*Tribolium castaneum*) and Japanese beetle larvae (*Popillia japonica*). Also disclosed therein are novel *B. thuringiensis* genes, designated cryET33 and cryET34, which encode the coleopteran-inhibitory crystal proteins ET33 and ET34. cryET33 encodes the CryET33 (29-kDa) crystal protein, and the cryET34 gene encodes the 14-kDa CryET34 crystal protein. Also disclosed therein are methods of making and using transgenic cells comprising the novel nucleic acid sequences of the invention.

Rupar et al. (WO00/066742; PCT/US00/12136) describe still other expression systems isolated from *Bacillus thuringiensis* stains which express proteins, which, when present in approximately equimolar concentrations, exhibit Coleopteran insecticidal activity. In particular, a binary toxin system referred to as CryET80 and CryET76, ET76 being about 44 kDa and ET80 being about 14 kDa, are effective in controlling corn rootworms.

Narva et al. (U.S. patent application Ser. No. 09/378,088; WO01/14417(A2); PCT/US00/22942) disclose yet at least one other coleopteran inhibitory binary toxin exhibiting corn rootworm controlling bioactivity, isolated from *Bacillus thuringiensis*, and describe the construction of a fusion between the two components of the toxin, but failed do demonstrate any bioactivity of this fusion.

It would be useful to provide a protein to plants which exhibits coleopteran-inhibitory activity, which is less than about 74-kDa in size, which is expressed from a single open reading frame in order to, at least in plants, ensure simultaneous expression, and in particular in plants, in consideration of conservation of the genetic elements, create an easier means for breeding purposes.

SUMMARY OF THE INVENTION

The present invention discloses novel coleopteran-inhibitory proteins and fusions of these proteins which also surprisingly exhibit insecticidal activity equivalent to the levels of activity exhibited by the native proteins, as well as novel nucleic acid sequences which encode these proteins. Some of the improvements in the art claimed and disclosed herein include the expression of a nucleic acid sequence encoding two-component toxins in planta driven by one promoter, wherein said sequence encodes a fusion of the two components which allows for conservation of genetic elements and ensures expression of the whole toxin within one cell at the same time. Also disclosed are methods of making and using said nucleic acid sequence in the development of transgenic plant cells containing the nucleic acid sequences disclosed herein.

One aspect of the present invention includes the amino acid and nucleic acid sequences as set forth in SEQ ID:2 and SEQ ID:4, respectively corresponding to *Bacillus thuringiensis* insecticidal crystal proteins tIC100 and tIC101. These proteins can be isolated and purified after expression from such nucleic acids as those set forth in SEQ ID NO:1 and SEQ ID NO:3.

Another aspect of the present invention includes novel amino acid and nucleic acid sequences resulting from the fusion of the CryET33 coding sequence in frame with the CryET34 coding sequence (SEQ ID NO:11, SEQ ID NO:13, SEQ ID NO:15, SEQ ID NO:17), and novel amino acid and nucleic acid sequences resulting from the fusion of the CryET34 coding sequence in frame with the CryET33 coding sequence (SEQ ID NO:19, SEQ ID NO:21). The present invention also includes novel amino acid and nucleic acid sequences resulting from the fusion of the tIC100 coding sequence in frame with the tIC101 coding sequence (SEQ ID NO:7, SEQ ID NO:9), and amino acid and nucleic acid sequences resulting from the fusion of the tIC101 coding sequence in frame with the tIC100 coding sequence (SEQ ID NO:5). Given the similarity in size, sequence, and insect inhibitory spectrum activity between the CryET33 and tIC100 proteins, as well as between the CryET34 and tIC101 proteins, fusions comprising the CryET33 sequence in frame with the tIC101 sequence and the tIC100 sequence in frame with the CryET34 sequence are also envisioned. tIC100 and tIC101 are each believed to be novel proteins which have been shown to exhibit Coleopteran insecticidal activity when present together in a composition in about equimolar ratios.

Another aspect of the present invention relates to a recombinant vector comprising a nucleic acid sequence encoding a CryET33/CryET34, CryET34/CryET33, tIC100/tIC101, tIC101/tIC100, CryET33/tIC101, or tIC100/CryET34 fusion protein, wherein the sequence encoding the protein is within a single expression cassette and its expression is controlled or driven by a single promoter. A recombinant host cell transformed with such a recombinant vector, and a biologically pure culture of the recombinant host cell so transformed are also exemplified herein. The host cell can be a plant cell or a bacterium, the bacterium preferably is being a *B. thuringiensis* bacterium. In addition, a recombinant vector comprising a nucleic acid sequence encoding the tIC100 and the tIC101 proteins from within a single operon is also disclosed. A recombinant host cell transformed with such a recombinant vector and a biologically pure culture of the recombinant host cell so transformed are also exemplified herein. The host cell can be a plant cell or a bacterium, the bacterium preferably being a *Pseudomonas* or a *B. thuringiensis* species of bacterium.

The present invention discloses an isolated insecticidal polypeptide selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, and SEQ ID NO:26. The isolated insecticidal polypeptide exhibits insecticidal activity when provided in an orally acceptable insect diet to a susceptible Coleopteran insect or Coleopteran insect larva. The isolated insecticidal polypeptide exhibits insecticidal activity when provided in an orally administrable diet to a susceptible Coleopteran insect or Coleopteran insect larva. The isolated insecticidal polypeptide exhibits a preferred insect inhibitory activity against a Coleopteran insect, and the preferred Coleopteran insect is a cotton boll weevil adult or a cotton boll weevil larva.

The insecticidal polypeptide can be formulated into a composition comprising an insecticidally effective amount of the polypeptide wherein the composition is a bacterial cell which expresses the polypeptide from a polynucleotide sequence that encodes said polypeptide. The composition can be any of or a combination of a cell extract, a cell suspension, a cell homogenate, a cell lysate, a cell supernatant, a cell filtrate, or a cell pellet. The bacterial cell composition is preferably a bacterial cell comprised of a bacterial species selected from the species consisting of a *Bacillus* species, an *Escherichia* species, a *Salmonella* species, an *Agrobacterium* species, and a *Pseudomonas* species of bacterial cell. The more preferable bacterial cell composition can be selected from the group of bacterial cells containing a recombinant plasmid, the group of bacterial cells being selected from a sIC2000 bacterial cell, a sIC2001 bacterial cell, a sIC2002 bacterial cell, a sIC2003 bacterial cell, a sIC2006 bacterial cell, a sIC2007 bacterial cell, a sIC2008 bacterial cell, and a sIC2010 bacterial cell.

The insecticidal composition can be an insecticidally effective amount of any of the polypeptides disclosed herein and can be formulated as a powder, dust, pellet, granule, spray, emulsion, colloid, or solution. The composition can be prepared by desiccation, lyophilization, homogenization, extraction, filtration, centrifugation, sedimentation, or concentration. The composition should contain the insecticidal polypeptide present in a concentration of from about 0.001% to about 99% by weight.

The present invention also discloses an isolated polynucleotide sequence encoding an insecticidal polypeptide, wherein said polynucleotide is selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, and SEQ ID NO:25, and biologically functional equivalents thereof. These polynucleotide sequences encode polypeptides which exhibit Coleopteran insecticidal activity when provided orally to a susceptible Coleopteran insect or Coleopteran insect larva. These polynucleotide sequences encode polypeptides which exhibit Coleopteran insecticidal activity when provided in an orally administrable diet or composition to a Coleopteran insect or Coleopteran insect larva. These polynucleotide sequences or variants of these sequences which encode the polypeptides as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, and SEQ ID NO:26 or functional equivalents of these polypeptides are useful for controlling Coleopteran insects, in particular cotton boll weevils and cotton boll weevil larvae. A further useful polynucleotide sequence which is disclosed herein is a polynucleotide sequence which is or is complementary to one or more of the polynucleotide sequences as set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, and SEQ ID NO:25 which hybridizes under stringent conditions as defined herein to a polynucleotide sequence which is complementary to or which encodes a polypeptide selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, and SEQ ID NO:26, and biologically functional equivalents thereof.

Nucleic Acid and Amino Acid Sequences

The present invention concerns nucleic acid sequences that can be isolated from *Bacillus thuringiensis* stains, or synthesized entirely in vitro using methods that are well-known to those of skill in the art. As used herein, the term "nucleic acid sequence" refers to a DNA molecule that has been isolated free of total genomic DNA of a particular species. Therefore, a nucleic acid sequence encoding a crystal protein or a fusion of crystal proteins refers to a DNA molecule that contains crystal protein coding sequences yet is isolated away from, or purified free from, total genomic DNA of the species from which the nucleic acid sequence is obtained, which in the instant case is the genome of the Gram-positive bacterial genus, *Bacillus*, and in particular, the species of *Bacillus* known as *B. thuringiensis*. Also included within the term "nucleic acid sequence", are recombinant vectors, including, for example, plasmids, cosmids, phagemids, phage, viruses, and the like.

Similarly, a nucleic acid sequence comprising an isolated or purified crystal protein-encoding gene or a nucleic acid sequence encoding a fusion of crystal proteins refers to a nucleic acid sequence which may include, in addition to peptide encoding sequences, certain other elements such as, regulatory sequences, isolated substantially away from other naturally occurring genes or protein-encoding sequences. In this respect, the term "gene" is used for simplicity to refer to a functional protein-, polypeptide- or peptide-encoding unit. As will be understood by those in the art this functional term includes both genomic sequences, operon sequences and smaller engineered gene sequences that express, or may be adapted to express, proteins, polypeptides or peptides.

"Isolated substantially away from other coding sequences" means that the gene of interest, in this case, a gene encoding a bacterial crystal protein or bacterial crystal protein fusion, forms the significant part of the coding region of the nucleic acid sequence, and that the nucleic acid sequence does not contain large portions of naturally-occurring coding sequences, such as large chromosomal fragments or other functional genes or operon coding regions. Of course, this refers to the nucleic acid sequence as originally isolated, and does not exclude genes, recombinant genes, synthetic linkers, or coding regions later added to the sequence by the hand of man.

In particular embodiments, the invention comprises isolated nucleic acid sequences selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:28, SEQ ID NO:29, SEQ ID NO:30, and SEQ ID NO:31. The invention also is directed to recombinant vectors incorporating nucleic acid sequences that encode a protein or fusion protein that includes within its amino acid sequence an amino acid sequence comprising SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, and SEQ ID NO:26.

The term "a sequence essentially as set forth in SEQ ID NO:2", for example, means that the sequence substantially corresponds to a portion of the sequence of SEQ ID NO:2 and has relatively few amino acids that are not identical to, or are not biologically functional equivalents of, the amino acids of any of the sequences contemplated herein. The term "biologically functional equivalent" is well understood in the art and is further defined in detail herein. Accordingly, amino acid sequences that have between about 70% and about 80%, or more preferably between about 81% and about 90%, or even more preferably between about 91% and about 99% amino acid sequence identity to each other likely are functional equivalents of each other if each amino acid sequence exhibits some measurable activity such as insecticidal activity and each amino acid sequence provides comparable measurable activity when present in equimolar or substantially identical equimolar amounts. Functional equivalence to the amino acid sequences of SEQ ID NO:2 when combined in equimolar ratios with SEQ ID NO:4, for example, will be amino acid sequences which are from about 70% to about 80% identical to, or more preferably from about 81% to about 90% identical to, or even more preferably from about 91% to about 99% identical to SEQ ID NO:2 and SEQ ID NO:4 and also exhibit substantially the same level of insecticidal activity on a weight to weight basis or a mole to mole basis.

Nucleic acid sequences can also be functionally equivalent to each other. In this case, a first nucleic acid sequence encoding a first peptide can be functionally equivalent to a second nucleic acid sequence encoding the same first peptide, primarily because of the redundancy of the genetic code. The second nucleic acid sequence can also be functionally equivalent to the first nucleic acid sequence if the peptide encoded by the second nucleic acid sequence is substantially similar to the first peptide, for example exhibiting from about 70% to about 80% identity to, or more preferably from about 81% to about 90% identity to, or even more preferably from about 91% to about 99% identity to the first peptide encoded by the first nucleic acid sequence, in particular, if the first and the second peptides exhibit substantially the same level of measurable activity on a weight to weight basis or on a mole to mole basis.

The nucleic acid sequences of the present invention encompass sequences encoding biologically-functional, equivalent peptides. Such sequences may arise as a consequence of codon degeneracy and functional equivalency that are known to occur naturally within nucleic acid sequences and the proteins thus encoded. Alternatively, functionally-equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test mutants in order to examine activity at the molecular level.

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

The nucleic acid sequences of the present invention, regardless of the length of the coding sequence itself, may be combined with other nucleic acid sequences, such as promoters, polyadenylation signals, additional restriction enzyme sites, multiple cloning sites, other coding sequences, and the like, such that their overall length may vary considerably. It is therefore contemplated that a nucleic acid sequence of almost any length may be employed, with the total length preferably being limited by the ease of preparation and use in the intended recombinant DNA protocol. For example, nucleic acid fragments may be prepared that include a short contiguous stretch encoding either of the peptide sequences disclosed in SEQ ID NO:2 or SEQ ID NO:4, or that are identical to or complementary to nucleic acid sequences which encode any of the peptides disclosed in SEQ ID NO:2 or SEQ ID NO:4, and particularly those nucleic acid is sequences disclosed in SEQ ID NO:1 or SEQ ID NO:3. For example, nucleic acid sequences consisting of from about 14 nucleotides, and up to about 10,000, or to about 5,000, or to about 3,000, or to about 2,000, or to about 1,000, or to about 500, or to about 200, or to about 100, or to about 50, and to about 14 base pairs in length (including all intermediate lengths) are also contemplated to be useful.

It will be readily understood that "intermediate lengths", in these contexts, means any length between the quoted ranges, such as 18, 19, 20, 21, 22, 23, etc.; 30, 31, 32, etc.; 50, 51, 52, 53, etc.; 100, 101, 102, 103, etc.; 150, 151, 152, 153, etc.; including all integers through the 200-500; 500-1,000; 1,000-2,000; 2,000-3,000; 3,000-5,000; and up to and including sequences of about 5200 nucleotides and the like.

It will also be understood that this invention is not limited to the particular nucleic acid sequences which encode peptides of the present invention, or which encode the amino acid sequences of, for example, SEQ ID NO:2 or SEQ ID NO:4, including those nucleic acid sequences which are particularly disclosed in SEQ ID NO:1 or SEQ ID NO:3. Recombinant vectors and isolated nucleic acid sequences may, therefore, variously include the peptide-coding regions themselves, coding regions bearing selected alterations or modifications in the basic coding region, or they may encode larger polypeptides that nevertheless include these peptide-coding regions or may encode biologically functional equivalent proteins or peptides that have variant amino acids sequences.

If desired, one may also prepare fusion proteins and peptides other than those disclosed and claimed herein, e.g., where the peptide-coding regions are aligned within the same expression unit with other proteins or peptides having desired functions, such as for purification or immunodetection purposes (e.g., proteins that may be purified by affinity chromatography and enzyme label coding regions, respectively).

Recombinant vectors form further aspects of the present invention. Particularly useful vectors are contemplated to be those vectors in which the coding portion of the nucleic acid sequence, whether encoding a full length protein or smaller peptide, is positioned under the control of a promoter. The promoter may be in the form of the promoter that is naturally associated with a gene encoding peptides of the present invention, as may be obtained by isolating the 5' non-coding sequences located upstream of the coding sequence, for example, using recombinant cloning and/or thermal amplification technology, in connection with the compositions disclosed herein.

Nucleic Acid Sequences as Hybridization Probes and Primers

In addition to their use in directing the expression of crystal fusion proteins or peptides of the present invention, the nucleic acid sequences contemplated herein also have a variety of other uses. For example, they also have utility as probes or primers in nucleic acid hybridization embodiments. As such, it is contemplated that nucleic acid sequences that comprise a sequence region that consists of at least a 14 nucleotide long contiguous sequence that has the same sequence as, or is complementary to, a 14 nucleotide long contiguous nucleic acid sequence of, for example, SEQ ID NO:1 or SEQ ID NO:3 will find particular utility. Longer contiguous identical or complementary sequences, e.g., those of about 20, 30, 40, 50, 100, 200, 500, 1000, 2000, 5000 base pairs, etc. (including all intermediate lengths and up to and including the full-length sequence of 5200 base pairs) will also be of use in certain embodiments.

The ability of such nucleic acid probes to specifically hybridize to crystal protein-encoding sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having sequence regions consisting of contiguous nucleotide stretches of 10-14, 15-20, 30, 50, or even of 100-200 nucleotides or so, identical or complementary to nucleic acid sequences of, for example, SEQ ID NO:1 or SEQ ID NO:3, are particularly contemplated as hybridization probes for use in, e.g., Southern and Northern blotting. Smaller fragments will generally find use in hybridization embodiments, wherein the length of the contiguous complementary region may be varied, such as between about 10-14 and about 100 or 200 nucleotides, but larger contiguous complementarity stretches may be used, according to the length complementary sequences one skilled in the art wishes to detect.

Of course, fragments of nucleic acids may also be obtained by other techniques such as, e.g., by mechanical shearing or by restriction enzyme digestion. Small nucleic acid sequences or fragments may be readily prepared by, for example, directly synthesizing the fragment by chemical means, as is commonly practiced using an automated oligonucleotide synthesizer. Also, fragments may be obtained by application of nucleic acid reproduction technology, such as the thermal amplification technology of U.S. Pat. Nos. 4,683, 195 and 4,683,202, by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of DNA fragments. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by about 0.02 M to about 0.15 M NaCl at temperatures of about 50° C. to about 70° C. Such selective conditions tolerate little, if any, mismatch between the probe and the template or target strand, and would be particularly suitable for isolating crystal protein-encoding DNA sequences. Detection of DNA sequences via hybridization is well-known to those of skill in the art and the teachings of U.S. Pat. Nos. 4,965,188 and 5,176,995 are exemplary of the methods of hybridization analyses. Teachings such as those found in the texts of Maloy et al., 1993; Segal 1976; Prokop, 1991; and Kuby, 1991, are particularly relevant.

Of course, for some applications, for example, where one desires to prepare mutants employing a mutant primer strand hybridized to an underlying template or where one seeks to isolate crystal protein-encoding sequences from related species, functional equivalents, or the like, less stringent hybridization conditions will typically be needed in order to allow formation of the heteroduplex. In these circumstances, one may desire to employ conditions such as about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avid/biotin, which are capable of giving a detectable signal. In preferred embodiments, one will likely desire to employ a fluorescent label such as fluorescein or related molecules, or an enzyme tag such as urease, jellyfish green fluorescent protein or variants thereof, alkaline phosphatase, or peroxidase, instead of radioactive or other environmentally undesirable reagents. In the case of enzyme tags, calorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantitated, by means of the incorporated label.

Recombinant Vectors and Crystal Protein Expression

In other embodiments, it is contemplated that certain advantages will be gained by positioning the coding DNA sequence under the control of a recombinant, or heterologous, promoter. As used herein, a recombinant or heterologous promoter is intended to refer to a promoter that is not normally associated with a DNA sequence encoding a crystal protein or peptide in its natural environment. Such promoters may include promoters normally associated with other genes, and/or promoters isolated from any bacterial, viral, eukaryotic, or plant cell. Naturally, it will be important to employ a promoter that effectively directs the expression of the is DNA sequence in the cell type, organism, or even animal, chosen for expression. Those of skill in the art of molecular biology generally know the use of promoter and cell type combinations for protein expression, for example, see Sambrook et al., 1989. The promoters employed may be constitutive, or inducible, and can be used under the appropriate conditions to direct high level expression of the introduced DNA sequence, such as is advantageous in the large-scale production of recombinant proteins or peptides. Appropriate promoter systems contemplated for use in high-level expression include, but are not limited to, the *Pichia* expression vector system (Pharmacia LKB Biotechnology).

In connection with expression embodiments to prepare recombinant proteins and peptides, it is contemplated that longer DNA sequences will most often be used, with DNA sequences encoding the entire peptide sequence being most preferred. However, it will be appreciated that the use of shorter DNA sequences to direct the expression of crystal peptides or epitopic core regions, such as may be used to generate anti-crystal protein antibodies, also falls within the scope of the invention. DNA sequences that encode peptide antigens from about 8 to about 50 amino acids in length, or more preferably, from about 8 to about 30 amino acids in length, or even more preferably, from about 8 to about 20 amino acids in length are contemplated to be particularly useful. Such peptide epitopes may be amino acid sequences which comprise contiguous amino acid sequences from, for example, SEQ ID NO:2 or SEQ ID NO:4.

Crystal Protein Transgenes and Transgenic Plants

In yet another aspect, the present invention provides methods for producing a transgenic plant which expresses a nucleic acid sequence encoding one of the novel crystal proteins of the present invention. The process of producing transgenic plants is well-known in the art. For example, the method comprises, in general, transforming a suitable host cell with a DNA sequence which contains a promoter operatively linked to a coding region that encodes, for example, a *B. thuringiensis* CryET33/CryET34 crystal fusion protein, or for example, a *B. thuringiensis* CrytIC100 or CrytIC101 crystal protein, or combinations of thereof. Such a coding region is generally operatively linked to a transcription-terminating region, whereby the promoter is capable of driving the transcription of the coding region in the cell, and hence providing the cell the ability to produce the recombinant protein in vivo. Alternatively, in instances where there is a desire to control, regulate, or decrease the amount of a particular recombinant crystal protein expressed in a particular transgenic cell, the invention also provides for the expression of crystal protein antisense mRNA. The use of antisense mRNA as a means of controlling or decreasing the amount of a given protein of interest in a cell is well-known in the art.

Further embodiments disclosed herein include expression of the proteins tIC100 and tIC101 (SEQ ID NO:2 and SEQ ID NO:4, respectively) in a plant, alone or in combination. For example, tIC100 cold be expressed in one plant from an expression cassette which is linked physically to a second cassette expressing tIC101 so that both proteins are expressed in the same plant. Each protein could be expressed in a plant from separate promoters but the coding sequences of each protein being physically linked, for example, on the same chromosome. Alternatively, each protein could be expressed in a plant from separate promoters but the coding sequences of each protein are not physically linked, for example, but the expression cassettes containing the promoter operably linked to the coding sequence are instead present in the same plant cell but on different chromosomes, so that Mendelian segregation can be achieved if desired. Alternatively, these proteins could be expressed from gene sequences transformed into the chloroplast genome, or from autonomously replicating epigenetic elements present within the chloroplast stroma. Yet another alternative embodiment comprises expression of these proteins as a fusion protein, the carboxy terminus of one of these proteins being linked either directly, by a flexible amino acid sequence linker, or by an amino acid sequence linker comprising a sequence susceptible to protease or autocatalytic cleavage upon expression or subcellular localization of the expression product fusion protein, or allowing cleavage of the linker region upon ingestion and localization of the fusion protein to the midgut of a target insect larvae, resulting in the release of the two proteins into the cellular milieu or into the midgut digestive fluids in approximately equimolar proportions and allowing the two proteins to be activated as a biologically active insecticidal crystal protein. Still as another alternative embodiment, tIC100 and tIC101 can be mixed with other related binary toxins in various compositions or proportions in order to achieve a broader host range, improved insecticidal specificity, or improved insecticidal activity. For example, tIC101 could be presented to a coleopteran insect in approximately equimolar concentrations with ET33, resulting in a surprisingly effective coleopteran insecticidal toxin. tIC100 could be presented to a coleopteran insect in approximately equimolar concentrations with ET34 also resulting in a surprisingly effective coleopteran insecticidal toxin. Alternatively, these toxin components could be presented to a susceptible coleopteran insect in the form of fusions resulting in a surprisingly effective coleopteran insecticidal toxin. In yet another embodiment, these toxins could be presented together (tIC100, tIC101, ET33, and ET34, together or in various compositions exhibiting insecticidal activity) to a coleopteran insect in a composition which facilitates insect resistance management practices. Alternatively, these toxin compositions could be provided with other coleopteran toxins such as for example Cry22, Cry3, or ET70 to provide surprisingly effective compositions for increasing insect resistance management. Additional resistance management practices contemplated herein include compositions of insecticidal proteins disclosed herein along with non-*Bacillus thuringiensis* insecticidal proteins, for example, insecticidal proteins isolatable from other species known in the art which have been shown to be insecticidal such as *Xenorhabdus* and *Photorhabdus* species of bacteria.

Another aspect of the invention comprises transgenic plants that express one or more genes or gene sequences encoding one or more of the novel polypeptide compositions disclosed herein. As used herein, the term "transgenic plant" is intended to refer to a plant that has incorporated DNA sequences, including but not limited to genes which are perhaps not normally present, DNA sequences not normally transcribed into RNA or translated into a protein ("expressed"), or any other genes or DNA sequences which one desires to introduce into the non-transformed plant, such as genes which may normally be present in the non-transformed plant but which one desires to either genetically engineer or to have altered expression.

Means for transforming a plant cell and the preparation of a transgenic cell line are well-known in the art, and are discussed herein. Vectors, plasmids, cosmids, YACs (yeast artificial chromosomes) and DNA sequences for use in transforming such cells will, of course, generally comprise either the operons, genes, or gene-derived sequences of the present invention, either native, or synthetically-derived, and particularly those encoding the disclosed crystal proteins. These DNA constructs can further include structures such as promoters, enhancers, introns, terminators, operators, polyadenylation signals, or other gene sequences which have positively- or negatively-regulating activity upon the particular genes of interest as desired. The DNA is sequence or gene may encode either a native or modified crystal protein, which will be expressed in the resultant recombinant cells, and/or which will impart an improved phenotype to the regenerated plant.

Such transgenic plants may be desirable for increasing the insect inhibitory resistance of a monocotyledonous or dicotyledonous plant, by incorporating into such a plant, a nucleic acid sequence comprising one or more of the sequences discussed herein and encoding crystal protein which is toxic to Coleopteran insects. Particularly preferred plants include corn, cotton, potato, soybean, canola, tomato, turf grasses, wheat, vegetables, ornamental plants, fruit trees, and the like.

In a related aspect, the present invention also encompasses a seed produced by the transformed plant, a progeny from such seed, and a seed produced by the progeny of the original transgenic plant, produced in accordance with the above process. Such progeny and seeds will have a crystal protein-encoding nucleic acid sequence stably incorporated into their genome, and such progeny plants will preferably inherit the traits conferred by the nucleic acid sequence in Mendelian fashion. All such transgenic plants having incorporated into their nuclear genome nucleic acid sequences comprising one or more of the sequences discussed herein and encoding one or more crystal proteins or polypeptides are aspects of this invention.

Plants comprising cells comprising chloroplasts transformed to contain nucleic acid sequences encoding the proteins of the present invention are also contemplated. Such plants would not be expected to pass these traits to their progeny plants or seeds through Mendelian fashion, but instead would pass on these traits to progeny through maternal transmission means well known in the art Site-Specific Mutagenesis.

Site-specific mutagenesis is a technique useful in the preparation of individual peptides, or biologically functional equivalent proteins or peptides, through specific mutagenesis of the underlying nucleic acid sequence. The technique further provides a ready ability to prepare and test sequence variants, for example, incorporating one or more of the foregoing considerations, by introducing one or more nucleotide sequence changes into the original nucleic acid sequence. Means for site-specific mutagenesis provides for the production of nucleic acid sequence variants through the use of specific synthetic oligonucleotide sequences which hybridize to the target nucleic acid sequence intended to be altered. Such synthetic oligonucleotides comprise the nucleic acid sequence of the desired mutation or sequence variant at the target site sequence, as well as a sufficient number of nucleotides complementary to the sequences flanking the target site sequence, said synthetic oligonucleotide acting as a primer sequence of sufficient size and sequence complexity to form a stable heteroduplex with the target nucleic acid sequence at the intended target site and generally flanking both sides of the intended target site sequence. Typically, a primer of about 17 to 25 nucleotides in length is preferred, with about 5 to 10 residues on both sides of the sequence being altered. The target site intended to be altered to form the variant sequence could incorporate either a single nucleotide, or alternatively could be two nucleotides or even more than two nucleotides each adjacent to each other or interspersed throughout the synthetic mutagenesis oligonucleotide sequence. One skilled in the art would readily recognize that a single nucleotide sequence change would require a synthetic oligonucleotide which would be considerably shorter in length than would a synthetic oligonucleotide sequence which is intended for use in incorporating two or more changes to the original nucleotide sequence, and therefore would generally, although not always, require longer sequences of complementarity to the sequences flanking the intended target site sequence(s).

Crystal Protein Screening and Detection Kits

The present invention contemplates methods and kits for screening samples suspected of containing crystal protein polypeptides or crystal protein-related polypeptides, or cells producing such polypeptides. A kit may contain one or more antibodies of the present invention, and may also contain reagent(s) for detecting an interaction between a sample and an antibody of the present invention. The provided reagent(s) can be radio-, fluorescently- or enzymatically-labeled. The kit can contain a known radio-, fluorescent-, hapten-, or enzyme-labeled agent capable of binding or interacting with a nucleic acid, protein or antibody of the present invention.

The reagent(s) of the kit can be provided as a liquid solution, attached to a solid support or as a dried powder. Preferably, when the reagent(s) are provided in a liquid solution, the liquid solution is an aqueous solution. Preferably, when the reagent(s) provided are attached to a solid support, the solid support can be chromatograph media, a test plate having a plurality of wells, or a microscope slide. When the reagent(s) provided are a dry powder, the powder can be reconstituted by the addition of a suitable solvent, that may be provided.

In still further embodiments, the present invention concerns immunodetection methods and associated kits. It is proposed that the crystal proteins or peptides of the present invention may be employed to detect antibodies having reactivity therewith, or, alternatively, antibodies prepared in accordance with the present invention, may be employed to detect crystal proteins or crystal protein-related epitope-containing peptides. In general, these methods will include first obtaining a sample suspected of containing such a protein, peptide or antibody, contacting the sample with an antibody or peptide in accordance with the present invention, as the case may be, under conditions effective to allow the formation of an immunocomplex, and then detecting the presence of the immunocomplex.

In general, the detection of immunocomplex formation is quite well known in the art and may be achieved through the application of numerous approaches. For example, the present invention contemplates the application of ELISA, RIA, immunoblot (e.g., dot blot), indirect immunofluorescence techniques and the like. Generally, immunocomplex formation will be detected through the use of a label, such as a radiolabel or an enzyme tag (such as alkaline phosphatase, horseradish peroxidase, or the like). Of course, one may find additional advantages through the use of a secondary binding ligand such as a second antibody or a biotin/avidin ligand binding arrangement, as is known in the art.

For assaying purposes, it is proposed that virtually any sample suspected of comprising either a crystal protein or peptide or a crystal protein-related peptide or antibody sought to be detected, as the case may be, may be employed. It is contemplated that such embodiments may have application in the tittering of antigen or antibody samples, in the selection of hybridomas, and the like. In related embodiments, the present invention contemplates the preparation of kits that may be employed to detect the presence of crystal proteins or related peptides and/or antibodies in a sample. Samples may include cells, cell supernatants, cell suspensions, cell extracts, enzyme fractions, protein extracts, or other cell-free compositions suspected of containing crystal proteins or peptides. Generally speaking, kits in accordance with the present invention will include a suitable crystal protein, peptide or an antibody directed against such a protein or peptide, together with an immunodetection reagent and a means for containing the antibody or antigen and reagent. The immunodetection reagent will typically comprise a label associated with the antibody or antigen, or associated with a secondary binding ligand. Exemplary ligands might include a secondary antibody directed against the first antibody or antigen or a biotin or avidin (or streptavidin) ligand having an associated label. Of course, as noted above, a number of exemplary labels are known in the art and all such labels may be employed in connection with the present invention.

The container will generally include a vial into which the antibody, antigen or detection reagent may be placed, and preferably suitably subsequently distributed into samples intended for analysis. The kits of the present invention will also typically include a means for containing the antibody, antigen, and reagent containers in close confinement for commercial sale. Such containers may include injection or blow-molded plastic containers into which the desired vials are retained.

Biological Functional Equivalents

Modification and changes may be made in the structure of the peptides of the present invention and nucleic acid sequences which encode them and still obtain a functional molecule that encodes a protein or peptide with desirable characteristics. The following is a discussion based upon changing the amino acids of a protein to create an equivalent, or even an improved, second-generation molecule. In particular embodiments of the invention, mutated or variant crystal proteins are contemplated to be useful for increasing the insect inhibitory activity of the protein, and consequently preferably increasing the insect inhibitory activity and/or expression of the recombinant transgene in a plant cell. The amino acid changes may be achieved by changing the codons of the DNA sequence, according to the codons given in Table 1.

TABLE 1

Amino Acids and Corresponding Codons

| Amino Acids | * | ** | Codons |
|---|---|---|---|
| Alanine | Ala | A | GCA GCC GCG GCU |
| Cysteine | Cys | C | UGC UGU |
| Aspartate | Asp | D | GAC GAU |
| Glutamate | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

\* indicates three letter abbreviation for the corresponding amino acid name
\*\* indicates single letter abbreviation for the corresponding amino acid name For example, certain amino acids, known as conservative amino acids, may be substituted for other amino acids in a protein structure without appreciable loss of interactive binding capacity with structures such as, for example, antigen-binding regions of antibodies or binding sites on substrate molecules. Since it is the interactive capacity and nature of a protein that defines the protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics bye and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (-0.4); threonine (-0.7); serine (-0.8); tryptophan (-0.9); tyrosine (-1.3); proline (-1.6); histidine (-3.2); glutamate (-3.5); glutamine (-3.5); aspartate (-3.5); asparagine (-3.5); lysine (-3.9); and arginine (-4.5).

It is known in the art that certain amino acids may be substituted for other amino acids having a similar hydropathic index or score and still result in a protein with similar biological activity, i.e., still obtain a biological functionally equivalent protein. In making such changes, the substitution of amino acids whose hydropathic indices are within +−0.2 are preferred, those which are within +/−0.1 are particularly preferred, and those within +/−0.05 are even more particularly preferred.

It is also understood in the art that the substitution of like amino acids can be made effectively on the basis of hydrophilicity. U.S. Pat. No. 4,554,101, incorporated herein by reference, discloses that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0.+−0.1); glutamate (+3.0.+−0.1); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within +/−0.2 are preferred, those which are within +/−0.1 are particularly preferred, and those within +/−0.05 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

Crystal Protein Insect Inhibitory Compositions and Methods of Use

The inventors contemplate that the crystal protein compositions disclosed herein will find particular utility as insect inhibitory or insecticidal compositions for topical and/or systemic application to field crops, grasses, fruits and vegetables, and ornamental plants. In a preferred embodiment, the biological insect inhibitory or insecticidal composition comprises an oil flowable suspension of bacterial cells which expresses a novel crystal protein disclosed herein. Any bacterial host cell expressing the novel nucleic acid sequences disclosed herein and producing a crystal protein is contemplated to be useful, such as *B. thuringiensis*, *B. megaterium*, *B. subtilis*, *E. coli*, or *Pseudomonas* spp.

In another embodiment, the biological insect inhibitory composition comprises a water dispersible granule. This granule comprises bacterial cells which express one or more of the novel crystal proteins disclosed herein. Bacteria such as *B. thuringiensis*, *B. megaterium*, *B. subtilis*, *E. coli*, or *Pseudomonas* spp. cells transformed with a DNA sequence disclosed herein and expressing one or more of the crystal proteins are also contemplated to be useful.

In a third embodiment, the biological insect inhibitory or insecticidal composition comprises a wettable powder, dust, pellet, or colloidal concentrate. This powder comprises bacterial cells which express one or more of the novel crystal proteins disclosed herein. Bacteria such as *B. thuringiensis*,

*B. megaterium, B. subtilis, E. coli,* or *Pseudomonas* spp. cells transformed with one or more of the nucleic acid sequences disclosed herein and expressing the crystal protein are also contemplated to be useful. Such dry forms of the insect inhibitory compositions may be formulated to dissolve immediately upon wetting, or alternatively, dissolve in a controlled-release, sustained-release, or other time-dependent manner.

In a fourth embodiment, the biological insect inhibitory or insecticidal composition is comprises an aqueous suspension of bacterial cells such as those described above which express the crystal protein. Such aqueous suspensions may be provided as a concentrated stock solution which is diluted prior to application, or alternatively, as a diluted solution ready-to-apply. For methods involving application of bacterial cells, the cellular host containing the crystal protein gene(s) may be grown in any convenient nutrient medium, where the DNA construct provides a selective advantage, providing for a selective medium so that substantially all or all of the cells retain the *B. thuringiensis* gene. These cells may then be harvested in accordance with conventional means. Alternatively, the cells can be treated prior to harvesting.

When the insect inhibitory or insecticidal compositions comprise intact *B. thuringiensis* cells expressing the protein of interest, such bacteria may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, suspensions, emulsifiable concentrates, or the like. The ingredients may include rheological agents; surfactants, emulsifiers, dispersants, or polymers.

Alternatively, the novel proteins discussed and claimed herein may be prepared by native or recombinant bacterial expression systems in vitro and isolated for subsequent field application. Such protein may be either in crude cell lysates, suspensions, colloids, etc., or alternatively may be purified, refined, buffered, and/or further processed, before formulating in an active biocidal formulation. Likewise, under certain circumstances, it may be desirable to isolate crystals and/or spores from bacterial cultures expressing the crystal protein and apply solutions, suspensions, or colloidal preparations of such crystals and/or spores as the active bioinsect inhibitory composition.

Regardless of the method of application, the amount of the active component(s) is applied at an insect inhibitory- or insecticidally-effective amount, which will vary depending on such factors as, for example, the specific coleopteran-inhibitory insects to be controlled, the specific plant or crop to be treated, the environmental conditions, and the method, rate, and quantity of application of the insect inhibitory-active composition.

The insect inhibitory compositions described may be made by formulating either the bacterial cell, crystal and/or spore suspension, or isolated protein component with the desired agriculturally-acceptable carrier. The compositions may be formulated prior to administration in an appropriate means such as lyophilized, freeze-dried, dessicated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term "agriculturally-acceptable carrier" covers all adjuvants, e.g., inert components, dispersants, surfactants, tackifiers, binders, etc. that are ordinarily used in insecticide formulation technology; these are well known to those skilled in insecticide formulation. The formulations may be mixed with one or more solid or liquid adjuvants and prepared by various means, e.g., by homogeneously mixing, blending and/or grinding the insect inhibitory or insecticidal composition with suitable adjuvants using conventional formulation techniques.

The insect inhibitory or insecticidal compositions of this invention are applied to the environment of the target coleopteran insect, typically onto the foliage of the plant or crop to be protected, by conventional methods, preferably by spraying. The strength and duration of insect inhibitory or insecticidal application will be set with regard to conditions specific to the particular pest(s), crop(s) to be treated and particular environmental conditions. The proportional ratio of active ingredient to carrier will naturally depend on the chemical nature, solubility, and stability of the insect inhibitory or insecticidal composition, as well as the particular formulation contemplated.

Other application techniques, e.g., dusting, sprinkling, soaking, soil injection, seed coating, seedling coating, spraying, aerating, misting, atomizing, and the like, are also feasible and may be required under certain circumstances such as e.g., insects that cause root or stalk infestation, or for application to delicate vegetation or ornamental plants. These application procedures are also well-known to those of skill in the art.

The insect inhibitory or insecticidal composition of the invention may be employed in the method of the invention singly or in combination with other compounds, including and not limited to other pesticides. The method of the invention may also be used in conjunction with other treatments such as surfactants, detergents, polymers or time-release formulations. The insect inhibitory or insecticidal compositions of the present invention may be formulated for either systemic or topical use.

The concentration of insect inhibitory or insecticidal composition which is used for environmental, systemic, or foliar application will vary widely depending upon the nature of the particular formulation, means of application, environmental conditions, and degree of biocidal activity. Typically, the bioinsect inhibitory or insecticidal composition will be present in the applied formulation at a concentration of at least about 1% by weight and may be up to and including about 99% by weight. Dry formulations of the compositions may be from about 1% to about 99% or more by weight of the composition, while liquid formulations may generally comprise from about 1% to about 99% or more of the active ingredient by weight. Formulations which comprise intact bacterial cells will generally contain from about $10^4$ to about $10^7$ cells/mg.

The insect inhibitory or insecticidal formulation may be administered to a particular plant or target area in one or more applications as needed, with a typical field application rate per hectare ranging on the order of from about 50 g to about 500 g of active ingredient, or of from about 500 g to about 1000 g, or of from about 1000 g to about 5000 g or more of active ingredient.

BRIEF DESCRIPTION OF THE DRAWINGS

The drawings form part of the present specification and are included to further demonstrate certain aspects of the present invention. The invention may be better understood by reference to one or more of these drawings in combination with the detailed description of specific embodiments presented herein.

Figure 1:
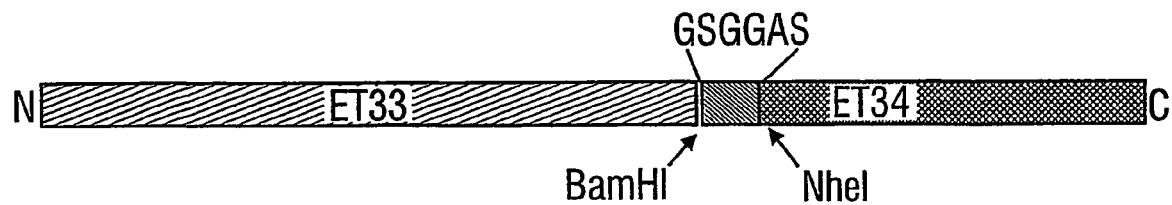
FIG. 1 is a schematic representation of a CryET33/CryET34 fusion protein or a tIC100/tIC101 fusion protein linked together in frame by a coding sequence flanked by BamHI and NheI restriction sites and encoding a peptide sequence comprising Gly-Ser-Gly-Gly-Ala-Ser (SEQ ID NO:34).

DESCRIPTION OF ILLUSTRATIVE EMBODIMENTS

Some Advantages of the Invention

CryET33 and CryET34 incombination, and tIC100 and tIC101 in combination, are both two-component insecticidal protein systems, each derived from different *Bacillus thuringiensis* strains, and requiring both of the two proteins in an approximately equimolar ratio for bioactivity. Therefore, for either system to be effective, both proteins need to be present at the same time in order to confer protection to plant against coleopteran species insect infestation, and to boll weevil in particular. Each of the proteins are expressed from different coding sequences in their respective strain of Bt, however, each set of proteins, i.e., CryET33 and CryET34 or CrytIC100 and CrytIC101, are expressed together in Bt from a polycistronic messenger RNA transcribed from a single DNA sequence in which both coding sequences are linked together in the genome. Therefore, the ability to express both proteins as a single construct in plants would eliminate several problems associated with attempting to express two separate proteins concurrently in a transgenic plant system. The major advantage of the fusion construct is that both proteins will be expressed simultaneously as they are under the control of a single promoter element. It is readily apparent to one skilled in the art that the simultaneous expression of two constructs in planta to achieve equimolar ratios of the proteins would be much more difficult than enabling the expression of one construct. A corollary to this benefit then, is that expression of both proteins in a single cassette would simplify subsequent breeding. In a subsequent breeding, the gene encoding both proteins would be transmitted to the progeny, or not at all, depending on whether the parent transmitting the gene was homozygous or heterozygous for the trait at the locus of the gene within the chromosome containing the gene. However, by expressing the proteins from a common cassette, the situation where only one gene of the pair is transmitted to subsequent generations will not occur if the genes are present on different expression cassettes and distal from each other on the same chromosome or on different chromosomes, thus reducing the complexity of the breeding of plants with the insect inhibitory protein expressed. Deletion of one gene of the pair by a crossover between elements in common within an expression cassette would render this inhibitory or insecticidal system of binary toxins derived from *Bacillus thuringiensis* ineffective. A fusion protein would be protected from such an occurrence, as both proteins would be expressed concurrently from within a single expression cassette. Expression as a fusion protein would also eliminate problems of gene silencing experienced with expression of two novel proteins under the control of similar promoter elements.

Definitions

The following words and phrases have the meanings set forth below.

Expression: The combination of intracellular processes, including transcription and translation undergone by a coding DNA molecule such as a structural gene to produce a polypeptide.

Promoter: A recognition site on a DNA sequence or group of DNA sequences that provide an expression control element for a structural gene and to which RNA polymerase specifically binds and initiates RNA synthesis (transcription) of that gene.

Regeneration: The process of growing a plant from a plant cell (e.g., plant protoplast or explant).

Structural gene: A gene that is expressed to produce a polypeptide.

Susceptible insect larva: an insect larva which, upon having orally ingested a sample of diet containing one or more of the proteins of the present invention, the diet being either artificially produced or obtained from a plant tissue artificially coated with or expressing one or more of the proteins of the present invention from a recombinant gene or genes, is growth inhibited as measured by failure to gain weight, molting cycle frequency inhibition, observed lethargic behaviour, reduction in frass production, or death in comparison to either 1) a larvae which does not exhibit any of these indications when feeding upon the same diet provided to a susceptible larvae, or 2) a larvae which is feeding upon a control diet which does not contain the one or more proteins of the present invention.

Transformation: A process of introducing an exogenous DNA sequence (e.g., a vector, a recombinant DNA molecule) into a cell or protoplast in which that exogenous DNA is incorporated into a chromosome or is capable of autonomous replication.

Transformed cell: A cell whose genetic composition, either chromosomal DNA or other naturally occurring intracellular DNA, has been altered by the introduction of an exogenous DNA molecule into the genetic composition of that cell.

Transgenic cell: Any cell derived or regenerated from a transformed cell or derived from a transgenic cell. Exemplary transgenic cells include plant calli derived from a transformed plant cell and particular cells such as leaf, root, stem, e.g., somatic cells, or reproductive (germ) cells obtained from a transgenic plant regenerated from a transformed cell.

Transgenic plant: A plant or progeny thereof derived from a transformed plant cell or protoplast, wherein the plant DNA contains an introduced exogenous DNA molecule not originally present in a native, non-transgenic plant of the same strain. The terms "transgenic plant" and "transformed plant" have sometimes been used in the art as synonymous terms to define a plant containing an exogenous and artificially introduced DNA molecule within its own naturally occurring genetic composition. However, it is thought more scientifically correct to refer to a regenerated plant or callus obtained from a transformed plant cell or protoplast as being a transgenic plant, and that usage will be followed herein.

Vector: A DNA molecule capable of replication in a host cell and/or to which another DNA sequence can be operatively linked so as to bring about replication of the attached sequence. A plasmid is an exemplary vector.

Probes and Primers

In another aspect, nucleic acid sequence information provided by the invention allows for the preparation of relatively short DNA (or RNA) sequences having the ability to specifically hybridize to nucleic acid sequences of the selected polynucleotides disclosed herein. In these aspects, nucleic acid probes of an appropriate length are prepared based on a consideration of the nucleic acid sequence encoding the selected crystal protein, e.g., a sequence such as that shown in SEQ ID NO:1 or SEQ ID NO:3. The ability of such nucleic acid probes to specifically hybridize to a crystal protein-encoding nucleic acid sequence lends to those probes particular utility in a variety of embodiments. Most importantly, the probes may be used in a variety of assays for detecting the presence of complementary sequences in a given sample suspected of containing probe-complementary sequences.

In certain embodiments, it is advantageous to use oligonucleotide primers. The sequence of such primers is designed using a polynucleotide of the present invention for use in detecting, amplifying, modifying, or mutating a defined sequence of nucleic acid encoding a crystal protein from *B. thuringiensis* using thermal amplification technology. Sequences of related crystal protein genes from other species may also be amplified by thermal amplification technology using such primers.

In accordance with the present invention, a preferred nucleic acid sequence employed for hybridization studies or assays includes sequences that are complementary to at least a 14 to 30 or so long nucleotide sequence derived from a crystal protein-encoding sequence, such as that shown in SEQ ID NO:1 or SEQ ID NO:3. A size of at least 14 nucleotides in length helps to ensure that the fragment will be of sufficient length to form a duplex molecule that is both stable and selective. Molecules having complementary sequences over stretches greater than 14 bases in length are generally preferred, though, in order to increase stability and selectivity of the hybrid, and thereby improve the quality and degree of specific hybrid molecules obtained through probe hybridization. One will generally prefer to design nucleic acid molecules having sequence-complementary stretches of 14 to 20 nucleotides, or even longer where desired. Such fragments may be readily prepared by, for example, directly synthesizing the fragment by chemical means, by application of nucleic acid reproduction technology, such as thermal amplification technology disclosed in U.S. Pat. Nos. 4,683,195, and 4,683,202, herein incorporated by reference, or by excising selected DNA fragments from recombinant plasmids containing appropriate inserts and suitable restriction sites.

Expression Vectors

The present invention contemplates expression vectors comprising a polynucleotide of the present invention. Thus, in one embodiment an expression vector is an isolated and purified DNA molecule comprising a promoter operatively linked to an coding region that encodes a polypeptide of the present invention, which coding region is operatively linked to a transcription-terminating region, whereby the promoter drives the transcription of the coding region.

As used herein, the term "operatively linked" means that a promoter is connected to an coding region in such a way that the transcription of that coding region is controlled and regulated by that promoter. Means for operatively linking a promoter to a coding region are well known in the art.

In a preferred embodiment, the recombinant expression of DNAs encoding the crystal proteins of the present invention is preferable in a *Bacillus* host cell. Preferred host cells include *B. thuringiensis, B. megaterium, B. subtilis*, and related bacilli, with *B. thuringiensis* host cells being highly preferred. Promoters that function in bacteria are well-known in the art. An exemplary and preferred promoter for the *Bacillus* crystal proteins include any of the known crystal protein gene promoters, including the cryET33 and cryET34 gene promoters. Alternatively, mutagenized or recombinant crystal protein-encoding gene promoters may be engineered by the hand of man and used to promote expression of the novel gene sequences disclosed herein.

In an alternate embodiment, the recombinant expression of DNAs encoding the crystal proteins of the present invention is performed using a transformed Gram-negative bacterium such as an *E. coli* or *Pseudomonas* spp. host cell. Promoters which function in high-level expression of target polypeptides in *E. coli* and other Gram-negative host cells are also well-known in the art.

Where an expression vector of the present invention is to be used to transform a plant, a promoter is selected that has the ability to drive expression in plants. Promoters that function in plants are also well known in the art. Useful in expressing the polypeptide in plants are promoters that are inducible, viral, synthetic, constitutive as described (Poszkowski et al., 1989; Odell et al., 1985), and temporally regulated, spatially regulated, and spatio-temporally regulated (Chau et al., 1989).

A promoter is also selected for its ability to direct the transformed plant cell's or transgenic plant's transcriptional activity to the coding region. Structural genes can be driven by a variety of promoters in plant tissues. Promoters can be near-constitutive, such as the CaMV 35S promoter, or tissue-specific or developmentally specific promoters affecting dicots or monocots.

Where the promoter is a near-constitutive promoter such as CaMV 35S, increases in polypeptide expression are found in a variety of transformed plant tissues (e.g., callus, leaf, seed and root). Alternatively, the effects of transformation can be directed to specific plant tissues by using plant integrating vectors containing a tissue-specific promoter.

An exemplary tissue-specific promoter is the lectin promoter, which is specific for seed tissue. The Lectin protein in soybean seeds is encoded by a single gene (Le1) that is only expressed during seed maturation and accounts for about 2 to about 5% of total seed mRNA. The lectin gene and seed-specific promoter have been fully characterized and used to direct seed specific expression in transgenic tobacco plants (Vodkin et al., 1983; Lindstrom et al., 1990).

An expression vector containing a coding region that encodes a polypeptide of interest is engineered to be under control of the lectin promoter and that vector is introduced into plants using, for example, a protoplast transformation method (Dhir et al., 1991). The expression of the polypeptide is directed specifically to the seeds of the transgenic plant.

A transgenic plant of the present invention produced from a plant cell transformed with a tissue specific promoter can be crossed with a second transgenic plant developed from a plant cell transformed with a different tissue specific promoter to produce a hybrid transgenic plant that shows the effects of transformation in more than one specific tissue.

Exemplary tissue-specific promoters are corn sucrose synthetase 1 (Yang et al., 1990), corn alcohol dehydrogenase 1 (Vogel et al., 1989), corn light harvesting complex (Simpson, 1986), corn heat shock protein (Odell et al., 1985), pea small subunit RuBP carboxylase (Poulsen et al., 1986; Cashmore et al., 1983), Ti plasmid mannopine synthase (Langridge et al., 1989), Ti plasmid nopaline synthase (Langridge et al., 1989), petunia chalcone isomerase (Van Tunen et al., 1988), bean glycine rich protein 1 (Keller et al., 1989), CaMV 35s transcript (Odell et al., 1985) and Potato patatin (Wenzler et al., 1989). Preferred promoters are the cauliflower mosaic virus (CaMV 35S) promoter and the S-E9 small subunit RuBP carboxylase promoter.

The choice of which expression vector and ultimately to which promoter a polypeptide coding region is operatively linked depends directly on the functional properties desired, e.g., the location and timing of protein expression, and the host cell to be transformed. These are well known limitations inherent in the art of constructing recombinant DNA molecules. However, a vector useful in practicing the present invention is capable of directing the expression of the polypeptide coding region to which it is operatively linked.

Typical vectors useful for expression of genes in higher plants are well known in the art and include vectors derived from the tumor-inducing (Ti) plasmid of *Agrobacterium tumefaciens* described (Rogers et al., 1987). However, several other plant integrating vector systems are known to function in plants including pCaMVCN transfer control vector described (Fromm et al., 1985). Plasmid pCaMVCN (available from Pharmacia, Piscataway, N.J.) includes the cauliflower mosaic virus CaMV 35S promoter.

In preferred embodiments, the vector used to express the polypeptide includes a selection marker that is effective in a plant cell, preferably a drug resistance selection marker. One preferred drug resistance marker is the gene whose expression results in kanamycin resistance; i.e., the chimeric gene containing the nopaline synthase promoter, Tn5 neomycin phosphotransferase II (nptII) and nopaline synthase 3' non-translated region described (Rogers et al., 1988).

RNA polymerase transcribes a coding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA).

Means for preparing expression vectors are well known in the art. Expression (transformation vectors) used to transform plants and methods of making those vectors are described in U.S. Pat. Nos. 4,971,908, 4,940,835, 4,769,061 and 4,757,011, the disclosures of which are incorporated herein by reference. Those vectors can be modified to include a coding sequence in accordance with the present invention.

A variety of methods has been developed to operatively link DNA to vectors via complementary cohesive termini or blunt ends. For instance, complementary homopolymer tracts can be added to the DNA sequence to be inserted and to the vector DNA. The vector and DNA sequence are then joined by hydrogen bonding between the complementary homopolymeric tails to form recombinant DNA molecules.

A coding region that encodes a polypeptide which confers insect inhibitory activity to a cell transformed to express the polypeptide is preferably a sequence encoding a tIC100 and/or tIC101 polypeptide, or a CryET33/CryET34 fusion peptide, a CryET34/CryET33 fusion peptide, a tIC100/tIC101 fusion peptide, a tIC101/tIC100 fusion peptide, a CryET33/tIC101 fusion peptide, or a tIC100/CryET34 fusion peptide, each of these or combinations thereof being further defined as *B. thuringiensis* insecticidal crystal fusion proteins. For example, in preferred embodiments, such a coding region has the nucleic acid sequence of SEQ ID NO:11, SEQ ID NO:13, SEQ ID NO:15, or SEQ ID NO:17 to encode a CryET33/CryET34 fusion, or a functional equivalent of those sequences. Also, co-expression of coding sequences for either CryET33 or tIC100 along with either CryET34 or tIC101 are shown herein to confer insect inhibitory activity to a plant or host cell.

Characteristics of the Novel Crystal Proteins

The present invention provides novel polypeptides that define a whole or a portion of tIC100, tIC101, CryET33/CryET34 fusions, tIC100/tIC101 fusions, CryET33/tIC101 fusions, and tIC100/CryET34 fusions whereby the fusion proteins contain various linkers disclosed and claimed herein. Various calculated physical characteristics of tIC100, tIC101, CryET33/CryET34 fusions containing various linkers, and tIC100/tIC101 fusions containing various linkers are listed below. The calculated physical characteristics of tIC100/CryET34 and CryET33/tIC101 fusions are not listed; however, such characteristics could be easily derived using known methods by persons skilled in the art.

tIC100 tIC100 is a protein as set forth in SEQ ID NO:2 derived from a cryptic *B. thuringiensis* DNA sequence. The cryptic tIC100 coding sequence as set forth in SEQ ID NO:1 is a part of an operon containing the tIC101 coding sequence, and is adjacent to and upstream of the coding sequence for tIC101. The cryptic sequence upstream of tIC101 contains the complete coding sequence for tIC100 except that a single guanosine residue at position 84 of the native cryptic tIC100 coding sequence as set forth in SEQ ID NO:27 causes the tIC100 coding sequence to be out of frame. The frameshift was eliminated, as described in Example 6 herein, by removing the single guanosine residue at position 84 to create the novel tIC100 coding sequence as set forth in SEQ ID NO:1, encoding the tIC100 protein as set forth in the translation in SEQ ID NO:1 and in the peptide sequence as set forth in SEQ ID NO:2, and as shown herein below.

```
Met Gly Ile Ile Asn Ile Gln Asp Glu Ile Asn Asp Tyr Met Lys Gly
1               5                   10                  15

Met Tyr Gly Ala Thr Ser Val Lys Ser Thr Tyr Asp Pro Ser Phe Lys
                20                  25                  30

Val Phe Asn Glu Ser Val Thr Pro Gln Tyr Asp Val Ile Pro Thr Glu
            35                  40                  45

Pro Val Asn Asn His Ile Thr Thr Lys Val Ile Asp Asn Pro Gly Thr
            50                  55                  60
```

-continued

```
Ser Glu Val Thr Ser Thr Val Thr Phe Thr Trp Thr Glu Thr Asp Thr
 65              70              75              80

Val Thr Ser Ala Val Thr Lys Gly Tyr Lys Val Gly Gly Ser Val Ser
             85              90              95

Ser Lys Ala Thr Phe Lys Phe Ala Phe Val Thr Ser Asp Val Thr Val
            100             105             110

Thr Val Ser Ala Glu Tyr Asn Tyr Ser Thr Thr Glu Thr Thr Thr Lys
        115             120             125

Thr Asp Thr Arg Thr Trp Thr Asp Ser Thr Thr Val Lys Ala Pro Pro
    130             135             140

Arg Thr Asn Val Glu Val Ala Tyr Ile Ile Gln Thr Gly Asn Tyr Asn
145             150             155             160

Val Pro Val Asn Val Glu Ser Asp Met Thr Gly Thr Leu Phe Cys Arg
            165             170             175

Gly Tyr Arg Asp Gly Ala Leu Ile Ala Ala Ala Tyr Val Ser Ile Thr
        180             185             190

Asp Leu Ala Asp Tyr Asn Pro Asn Leu Gly Leu Thr Asn Glu Gly Asn
        195             200             205

Gly Val Ala His Phe Lys Gly Glu Gly Tyr Ile Glu Gly Ala Gln Gly
    210             215             220

Leu Arg Ser Tyr Ile Gln Val Thr Glu Tyr Pro Val Asp Asp Asn Gly
225             230             235             240

Arg His Ser Ile Pro Lys Thr Tyr Ile Ile Lys Gly Ser Leu Ala Pro
            245             250             255

Asn Val Thr Leu Ile Asn Asp Arg Lys Glu Gly Arg
            260             265
```

The resulting protein is calculated to comprise the following composition, including the amino acid sequence residues, number of each amino acid residue, and mole percent of each combination of residues of a particular species as set forth in Table 2.

Molecular weight=29239. Residues=268

Isoelectric point=4.79

TABLE 2

Amino Acid Composition of tIC100

| Residue Type | Number of Residues | Mole Percent | In tIC100 Protein |
|---|---|---|---|
| A = Ala | 15 | 5.597 | |
| B = Asx | 0 | 0.000 | |
| C = Cys | 1 | 0.373 | |
| D = Asp | 16 | 5.970 | |
| E = Glu | 14 | 5.224 | |
| F = Phe | 8 | 2.985 | |
| G = Gly | 21 | 7.836 | |
| H = His | 3 | 1.119 | |
| I = Ile | 17 | 6.343 | |
| K = Lys | 14 | 5.224 | |
| L = Leu | 8 | 2.985 | |
| M = Met | 4 | 1.493 | |
| N = Asn | 18 | 6.716 | |
| P = Pro | 12 | 4.478 | |
| Q = Gln | 5 | 1.866 | |
| R = Arg | 8 | 2.985 | |
| S = Ser | 19 | 7.090 | |
| T = Thr | 40 | 14.925 | |
| V = Val | 27 | 10.075 | |
| W = Trp | 2 | 0.746 | |
| Y = Tyr | 16 | 5.970 | |

TABLE 2-continued

Amino Acid Composition of tIC100

| Residue Type | Number of Residues | Mole Percent | In tIC100 Protein |
|---|---|---|---|
| Z = Glx | 0 | 0.000 | |
| A + G | 36 | 13.433 | Non-polar |
| S + T | 59 | 22.015 | Polar |
| D + E | 30 | 11.194 | Acidic |
| D + E + N + Q | 53 | 19.776 | |
| H + K + R | 25 | 9.328 | Basic |
| D + E + H + K + R | 55 | 20.522 | |
| I + L + M + V | 56 | 20.896 | Hydrophobic non-aromatic |
| F + W + Y | 26 | 9.701 | Aromatic | tIC101

The following amino acid sequence, numbered for convenience, represents an example of a CrytIC101 insecticidal protein. The amino acid sequence is represented at SEQ ID NO:4. One nucleotide sequence which encodes the tIC101 amino acid sequence is set forth at SEQ ID NO:3, which indicates the particular codons observed in the native B.t. coding sequence.

```
Met Thr Val Tyr Asn Val Thr Phe Thr Ile Lys Phe Tyr Asn Glu Gly
1               5                   10                  15
Glu Trp Gly Gly Pro Glu Pro Tyr Gly Lys Ile Tyr Ala Tyr Leu Gln
            20              25                  30
Asn Pro Asp His Asn Phe Glu Ile Trp Ser Gln Asp Asn Trp Gly Lys
        35                  40                  45
Asp Thr Pro Glu Lys Ser Ser His Thr Gln Thr Ile Lys Ile Ser Ser
    50                  55                  60
Pro Thr Gly Gly Pro Ile Asn Gln Met Cys Phe Tyr Gly Asp Val Lys
65              70                  75                      80
Glu Tyr Asp Val Gly Asn Ala Asp Asp Val Leu Ala Tyr Pro Ser Gln
            85                  90                  95
Lys Val Cys Ser Thr Pro Gly Thr Thr Ile Arg Leu Asn Gly Asp Glu
            100             105                 110
Lys Gly Ser Tyr Ile Gln Ile Arg Tyr Ser Leu Ala Pro Ala
            115             120                 125
```

The resulting protein is calculated to comprise the following composition, including the amino acid sequence residues, number of each amino acid residue, and mole percent of each combination of residues of a particular species as set forth in Table 3.

Molecular weight=14159. Residues=126

Isoelectric point=4.70

TABLE 3

Amino Acid Composition of tIC101

| Residue Type | Number of Residues | Mole Percent | In tIC101 Protein |
|---|---|---|---|
| A = Ala | 5 | 3.968 | |
| B = Asx | 0 | 0.000 | |
| C = Cys | 2 | 1.587 | |
| D = Asp | 8 | 6.349 | |
| E = Glu | 7 | 5.556 | |
| F = Phe | 4 | 3.175 | |
| G = Gly | 12 | 9.524 | |
| H = His | 2 | 1.587 | |
| I = Ile | 9 | 7.143 | |
| K = Lys | 8 | 6.349 | |
| L = Leu | 4 | 3.175 | |
| M = Met | 2 | 1.587 | |
| N = Asn | 8 | 6.349 | |
| P = Pro | 9 | 7.143 | |
| Q = Gln | 6 | 4.762 | |
| R = Arg | 2 | 1.587 | |
| S = Ser | 9 | 7.143 | |

TABLE 3-continued

Amino Acid Composition of tIC101

| Residue Type | Number of Residues | Mole Percent | In tIC101 Protein |
|---|---|---|---|
| T = Thr | 10 | 7.937 | |
| V = Val | 6 | 4.762 | |
| W = Trp | 3 | 2.381 | |
| Y = Tyr | 10 | 7.937 | |
| Z = Glx | 0 | 0.000 | |
| A + G | 17 | 13.492 | Non-polar |
| S + T | 19 | 5.079 | Polar |
| D + E | 15 | 11.905 | Acidic |
| D + E + N + Q | 29 | 23.016 | |
| H + K + R | 12 | 9.524 | Basic |
| D + E + H + K + R | 27 | 21.429 | |
| I + L + M + V | 21 | 16.667 | Hydrophobic non-aromatic |
| F + W + Y | 17 | 13.492 | Aromatic | tIC100/tIC101 Fusion with BamHI/NheI (GSGGAS) (SEQ ID NO:34) Linker

The following amino acid sequence, numbered for convenience, represents an example of a CrytIC100/CrytIC101 insecticidal protein fusion between CrytIC100 and CrytIC101, CrytIC100 being positioned at the amino terminus of the fusion, and containing a Gly-Ser-Gly-Gly-Ala-Ser (GSGGAS) (SEQ ID NO:34) amino acid sequence linker between the two protein sequences. The underlined amino acids at residues numbered from position 269 through position 274 indicate the linker sequence in this novel insecticidal fusion protein.

```
Met Gly Ile Ile Asn Ile Gln Asp Glu Ile Asn Asp Tyr Met Lys Gly  (SEQ ID NO: 8)
1               5                   10                  15

Met Tyr Gly Ala Thr Ser Val Lys Ser Thr Tyr Asp Pro Ser Phe Lys
            20                  25                  30
```

-continued

```
Val Phe Asn Glu Ser Val Thr Pro Gln Tyr Asp Val Ile Pro Thr Glu
         35                  40                  45

Pro Val Asn Asn His Ile Thr Thr Lys Val Ile Asp Asn Pro Gly Thr
 50                  55                  60

Ser Glu Val Thr Ser Thr Val Thr Phe Thr Trp Thr Glu Thr Asp Thr
 65                  70                  75                  80

Val Thr Ser Ala Val Thr Lys Gly Tyr Lys Val Gly Ser Val Ser
                 85                  90                  95

Ser Lys Ala Thr Phe Lys Phe Ala Phe Val Thr Ser Asp Val Thr Val
                100                 105                 110

Thr Val Ser Ala Glu Tyr Asn Tyr Ser Thr Thr Glu Thr Thr Thr Lys
                115                 120                 125

Thr Asp Thr Arg Thr Trp Thr Asp Ser Thr Thr Val Lys Ala Pro Pro
    130                 135                 140

Arg Thr Asn Val Glu Val Ala Tyr Ile Ile Gln Thr Gly Asn Tyr Asn
145                 150                 155                 160

Val Pro Val Asn Val Glu Ser Asp Met Thr Gly Thr Leu Phe Cys Arg
                165                 170                 175

Gly Tyr Arg Asp Gly Ala Leu Ile Ala Ala Tyr Val Ser Ile Thr
                180                 185                 190

Asp Leu Ala Asp Tyr Asn Pro Asn Leu Gly Leu Thr Asn Glu Gly Asn
        195                 200                 205

Gly Val Ala His Phe Lys Gly Glu Gly Tyr Ile Glu Gly Ala Gln Gly
210                 215                 220

Leu Arg Ser Tyr Ile Gln Val Thr Glu Tyr Pro Val Asp Asp Asn Gly
225                 230                 235                 240

Arg His Ser Ile Pro Lys Thr Tyr Ile Ile Lys Gly Ser Leu Ala Pro
                245                 250                 255

Asn Val Thr Leu Ile Asn Asp Arg Lys Glu Gly Arg Gly Ser Gly Gly
                260                 265                 270

Ala Ser Met Thr Val Tyr Asn Val Thr Phe Thr Ile Lys Phe Tyr Asn
        275                 280                 285

Glu Gly Glu Trp Gly Gly Pro Glu Pro Tyr Gly Lys Ile Tyr Ala Tyr
290                 295                 300

Leu Gln Asn Pro Asp His Asn Phe Glu Ile Trp Ser Gln Asp Asn Trp
305                 310                 315                 320

Gly Lys Asp Thr Pro Glu Lys Ser Ser His Thr Gln Thr Ile Lys Ile
                325                 330                 335

Ser Ser Pro Thr Gly Gly Pro Ile Asn Gln Met Cys Phe Tyr Gly Asp
                340                 345                 350

Val Lys Glu Tyr Asp Val Gly Asn Ala Asp Asp Val Leu Ala Tyr Pro
                355                 360                 365

Ser Gln Lys Val Cys Ser Thr Pro Gly Thr Thr Ile Arg Leu Asn Gly
        370                 375                 380

Asp Glu Lys Gly Ser Tyr Ile Gln Ile Arg Tyr Ser Leu Ala Pro Ala
385                 390                 395                 400
```

The resulting protein is calculated to comprise the following protein composition, including the amino acid sequence residues, number of each amino acid residue, and mole percent of each combination of residues of a particular species as set forth in Table 4.

Molecular weight=43796. Residues=400

Isoelectric point=4.75

TABLE 4

Amino Acid Composition of tIC100/tIC101 Fusion [BamHI/NheI (GSGGAS) (SEQ ID NO: 34) Linker]

| Residue Type | Number of Residues | Mole Percent | In tIC100/101 Protein |
|---|---|---|---|
| A = Ala | 21 | 5.250 | |
| B = Asx | 0 | 0.000 | |
| C = Cys | 3 | 0.750 | |
| D = Asp | 24 | 6.000 | |
| E = Glu | 21 | 5.250 | |
| F = Phe | 12 | 3.000 | |
| G = Gly | 36 | 9.000 | |
| H = His | 5 | 1.250 | |
| I = Ile | 26 | 6.500 | |
| K = Lys | 22 | 5.500 | |
| L = Leu | 12 | 3.000 | |
| M = Met | 6 | 1.500 | |
| N = Asn | 26 | 6.500 | |
| P = Pro | 21 | 5.250 | |
| Q = Gln | 11 | 2.750 | |
| R = Arg | 10 | 2.500 | |
| S = Ser | 30 | 7.500 | |
| T = Thr | 50 | 12.500 | |
| V = Val | 33 | 8.250 | |
| W = Trp | 5 | 1.250 | |
| Y = Tyr | 26 | 6.500 | |
| Z = Glx | 0 | 0.000 | |
| A + G | 57 | 14.250 | Non-polar |
| S + T | 80 | 20.000 | Polar |
| D + E | 45 | 11.250 | Acidic |
| D + E + N + Q | 82 | 20.500 | |

TABLE 4-continued

Amino Acid Composition of tIC100/tIC101 Fusion [BamHI/NheI (GSGGAS) (SEQ ID NO: 34) Linker]

| Residue Type | Number of Residues | Mole Percent | In tIC100/101 Protein |
|---|---|---|---|
| H + K + R | 37 | 9.250 | Basic |
| D + E + H + K + R | 82 | 20.500 | |
| I + L + M + V | 77 | 19.250 | Hydrophobic non-aromatic |
| F + W + Y | 43 | 10.750 | Aromatic |

An insecticidal fusion protein similar to the tIC100/tIC101 fusion described in above and in Table 4 was constructed, but the DNA sequence representing the open reading frame encoding tIC101 peptide was positioned at the 5' end of the cassette so that the tIC101 peptide would be positioned at the amino terminal position of the fusion protein, while the DNA sequence representing the open reading frame encoding the tIC100 peptide was positioned toward the 3' end of the cassette so that the tIC100 peptide would be positioned at the carboxy terminal position of the fusion protein. The two proteins were also linked in frame by a sequence encoding a Gly-Ser-Gly-Gly-Ala-Ser (GSGGAS) (SEQ ID NO:34) linker peptide as described above. The resulting amino acid sequence of the fusion peptide, tIC101/tIC100, was identical in amino acid composition analysis to the tIC100/tIC101 fusion peptide described in Table 4, and exhibiting a molecular weight of 43796 Da, comprising 400 amino acid residues, and exhibiting a calculated isoelectric point of 4.75. This fusion peptide was also shown to demonstrate an effective coleopteran insect inhibitory bioactivity, in particular in cotton boll weevil bioassay. The amino acid sequence of the tIC101/tIC100 fusion peptide linked in frame by a GSGGAS (SEQ ID NO:34) linker is shown below, and the underlined residues at amino acid sequence positions 127-132 represent the GSGGAS (SEQ ID NO:34) linker:

```
Met Thr Val Tyr Asn Val Thr Phe Thr Ile Lys Phe Tyr Asn Glu Gly   (SEQ ID NO: 33)
1               5                   10                  15

Glu Trp Gly Gly Pro Glu Pro Tyr Gly Lys Ile Tyr Ala Tyr Leu Gln
            20                  25                  30

Asn Pro Asp His Asn Phe Glu Ile Trp Ser Gln Asp Asn Trp Gly Lys
        35                  40                  45

Asp Thr Pro Glu Lys Ser Ser His Thr Gln Thr Ile Lys Ile Ser Ser
    50                  55                  60

Pro Thr Gly Gly Pro Ile Asn Gln Met Cys Phe Tyr Gly Asp Val Lys
65                  70                  75                  80

Glu Tyr Asp Val Gly Asn Ala Asp Asp Val Leu Ala Tyr Pro Ser Gln
                85                  90                  95

Lys Val Cys Ser Thr Pro Gly Thr Thr Ile Arg Leu Asn Gly Asp Glu
            100                 105                 110

Lys Gly Ser Tyr Ile Gln Ile Arg Tyr Ser Leu Ala Pro Ala Gly Ser
        115                 120                 125

Gly Gly Ala Ser Met Gly Ile Ile Asn Ile Gln Asp Glu Ile Asn Asp
    130                 135                 140

Tyr Met Lys Gly Met Tyr Gly Ala Thr Ser Val Lys Ser Thr Tyr Asp
145                 150                 155                 160

Pro Ser Phe Lys Val Phe Asn Glu Ser Val Thr Pro Gln Tyr Asp Val
                165                 170                 175
```

-continued

```
Ile Pro Thr Glu Pro Val Asn Asn His Ile Thr Thr Lys Val Ile Asp
        180                 185                 190

Asn Pro Gly Thr Ser Glu Val Thr Ser Thr Val Thr Phe Thr Trp Thr
        195                 200                 205

Glu Thr Asp Thr Val Thr Ser Ala Val Thr Lys Gly Tyr Lys Val Gly
        210                 215                 220

Gly Ser Val Ser Ser Lys Ala Thr Phe Lys Phe Ala Phe Val Thr Ser
225                 230                 235                 240

Asp Val Thr Val Thr Val Ser Ala Glu Tyr Asn Tyr Ser Thr Thr Glu
                245                 250                 255

Thr Thr Thr Lys Thr Asp Thr Arg Thr Trp Thr Asp Ser Thr Thr Val
            260                 265                 270

Lys Ala Pro Pro Arg Thr Asn Val Glu Val Ala Tyr Ile Ile Gln Thr
        275                 280                 285

Gly Asn Tyr Asn Val Pro Val Asn Val Glu Ser Asp Met Thr Gly Thr
        290                 295                 300

Leu Phe Cys Arg Gly Tyr Arg Asp Gly Ala Leu Ile Ala Ala Ala Tyr
305                 310                 315                 320

Val Ser Ile Thr Asp Leu Ala Asp Tyr Asn Pro Asn Leu Gly Leu Thr
                325                 330                 335

Asn Glu Gly Asn Gly Val Ala His Phe Lys Gly Glu Gly Tyr Ile Glu
                340                 345                 350

Gly Ala Gln Gly Leu Arg Ser Tyr Ile Gln Val Thr Glu Tyr Pro Val
                355                 360                 365

Asp Asp Asn Gly Arg His Ser Ile Pro Lys Thr Tyr Ile Ile Lys Gly
        370                 375                 380

Ser Leu Ala Pro Asn Val Thr Leu Ile Asn Asp Arg Lys Glu Gly Arg
385                 390                 395                 400
``` tIC101/tIC100 Fusion with Gly-Gly Linker

The following amino acid sequence, numbered for convenience, represents an example of a CrytIC101/CrytIC100 insecticidal protein fusion between CrytIC101 and CrytIC100, CrytIC101 being positioned at the amino terminus of the fusion, and containing a Gly-Gly (GG) dipeptide linker between the two protein sequences. The underlined amino acids at residues numbered from position 127 through position 128 indicate the linker sequence in this novel insecticidal fusion protein.

```
Met Thr Val Tyr Asn Val Thr Phe Thr Ile Lys Phe Tyr Asn Glu Gly   (SEQ ID NO: 6)
1               5                   10                  15

Glu Trp Gly Gly Pro Glu Pro Tyr Gly Lys Ile Tyr Ala Tyr Leu Gln
                20                  25                  30

Asn Pro Asp His Asn Phe Glu Ile Trp Ser Gln Asp Asn Trp Gly Lys
            35                  40                  45

Asp Thr Pro Glu Lys Ser Ser His Thr Gln Thr Ile Lys Ile Ser Ser
        50                  55                  60

Pro Thr Gly Gly Pro Ile Asn Gln Met Cys Phe Tyr Gly Asp Val Lys
65                  70                  75                  80

Glu Tyr Asp Val Gly Asn Ala Asp Val Leu Ala Tyr Pro Ser Gln
                    85                  90                  95

Lys Val Cys Ser Thr Pro Gly Thr Thr Ile Arg Leu Asn Gly Asp Glu
                100                 105                 110

Lys Gly Ser Tyr Ile Gln Ile Arg Tyr Ser Leu Ala Pro Ala Gly Gly
            115                 120                 125

Met Gly Ile Ile Asn Ile Gln Asp Glu Ile Asn Asp Tyr Met Lys Gly
        130                 135                 140
```

-continued

```
Met Tyr Gly Ala Thr Ser Val Lys Ser Thr Tyr Asp Pro Ser Phe Lys
145                 150                 155                 160

Val Phe Asn Glu Ser Val Thr Pro Gln Tyr Asp Val Ile Pro Thr Glu
                165                 170                 175

Pro Val Asn Asn His Ile Thr Thr Lys Val Ile Asp Asn Pro Gly Thr
                180                 185                 190

Ser Glu Val Thr Ser Thr Val Thr Phe Thr Trp Thr Glu Thr Asp Thr
                195                 200                 205

Val Thr Ser Ala Val Thr Lys Gly Tyr Lys Val Gly Gly Ser Val Ser
        210                 215                 220

Ser Lys Ala Thr Phe Lys Phe Ala Phe Val Thr Ser Asp Val Thr Val
225                 230                 235                 240

Thr Val Ser Ala Glu Tyr Asn Tyr Ser Thr Thr Glu Thr Thr Thr Lys
                245                 250                 255

Thr Asp Thr Arg Thr Trp Thr Asp Ser Thr Thr Val Lys Ala Pro Pro
                260                 265                 270

Arg Thr Asn Val Glu Val Ala Tyr Ile Ile Gln Thr Gly Asn Tyr Asn
            275                 280                 285

Val Pro Val Asn Val Glu Ser Asp Met Thr Gly Thr Leu Phe Cys Arg
            290                 295                 300

Gly Tyr Arg Asp Gly Ala Leu Ile Ala Ala Ala Tyr Val Ser Ile Thr
305                 310                 315                 320

Asp Leu Ala Asp Tyr Asn Pro Asn Leu Gly Leu Thr Asn Glu Gly Asn
                325                 330                 335

Gly Val Ala His Phe Lys Gly Glu Gly Tyr Ile Glu Gly Ala Gln Gly
                340                 345                 350

Leu Arg Ser Tyr Ile Gln Val Thr Glu Tyr Pro Val Asp Asp Asn Gly
                355                 360                 365

Arg His Ser Ile Pro Lys Thr Tyr Ile Ile Lys Gly Ser Leu Ala Pro
            370                 375                 380

Asn Val Thr Leu Ile Asn Asp Arg Lys Glu Gly Arg
385                 390                 395
```

The resulting protein is calculated to comprise the following composition, including the amino acid sequence residues, number of each amino acid residue, and mole percent of each combination of residues of a particular species as set forth in Table 5.

Molecular weight=43494. Residues=396

Isoelectric point=4.75

TABLE 5

Amino Acid Composition of tIC100/101 Fusion [Gly-Gly Linker]

| Residue Type | Number of Residues | Mole Percent | In tIC100 Protein |
|---|---|---|---|
| A = Ala | 20 | 5.051 | |
| B = Asx | 0 | 0.000 | |
| C = Cys | 3 | 0.758 | |
| D = Asp | 24 | 6.061 | |
| E = Glu | 21 | 5.303 | |
| F = Phe | 12 | 3.030 | |
| G = Gly | 35 | 8.838 | |
| H = His | 5 | 1.263 | |
| I = Ile | 26 | 6.566 | |
| K = Lys | 22 | 5.556 | |
| L = Leu | 12 | 3.030 | |

TABLE 5-continued

Amino Acid Composition of tIC100/101 Fusion [Gly-Gly Linker]

| Residue Type | Number of Residues | Mole Percent | In tIC100 Protein |
|---|---|---|---|
| M = Met | 6 | 1.515 | |
| N = Asn | 26 | 6.566 | |
| P = Pro | 21 | 5.303 | |
| Q = Gln | 11 | 2.778 | |
| R = Arg | 10 | 2.525 | |
| S = Ser | 28 | 7.071 | |
| T = Thr | 50 | 12.626 | |
| V = Val | 33 | 8.333 | |
| W = Trp | 5 | 1.263 | |
| Y = Tyr | 26 | 6.566 | |
| Z = Glx | 0 | 0.000 | |
| A + G | 55 | 13.889 | Non-polar |
| S + T | 78 | 19.697 | Polar |
| D + E | 45 | 11.364 | Acidic |
| D + E + N + Q | 82 | 0.707 | |
| H + K + R | 37 | 9.343 | Basic |
| D + E + H + K + R | 82 | 20.707 | |
| I + L + M + V | 77 | 19.444 | Hydrophobic non-aromatic |
| F + W + Y | 43 | 10.859 | Aromatic |

CryET33/CryET34 Fusion with BamHI/NheI (GSGGAS) (SEQ ID NO:34) Linker

The following amino acid sequence, numbered for convenience, represents an example of a CryET33/CryET34 insecticidal protein fusion between CryET33 and CryET34 and containing a Gly-Ser-Gly-Gly-Ala-Ser (GSGGAS) (SEQ ID NO:34) amino acid sequence linker between the two protein sequences. The underlined amino acids at residues numbered from position 268 through position 273 indicate the linker sequence in this novel insecticidal fusion protein.

```
Met Gly Ile Ile Asn Ile Gln Asp Glu Ile Asn Asn Tyr Met Lys Glu  (SEQ ID NO: 14)
1               5                   10                  15

Val Tyr Gly Ala Thr Thr Val Lys Ser Thr Tyr Asp Pro Ser Phe Lys
            20                  25                  30

Val Phe Asn Glu Ser Val Thr Pro Gln Phe Thr Glu Ile Pro Thr Glu
        35                  40                  45

Pro Val Asn Asn Gln Leu Thr Thr Lys Arg Val Asp Asn Thr Gly Ser
    50                  55                  60

Tyr Pro Val Glu Ser Thr Val Ser Phe Thr Trp Thr Glu Thr His Thr
65                  70                  75                  80

Glu Thr Ser Ala Val Thr Glu Gly Val Lys Ala Gly Thr Ser Ile Ser
                85                  90                  95

Thr Lys Gln Ser Phe Lys Phe Gly Phe Val Asn Ser Asp Val Thr Leu
            100                 105                 110

Thr Val Ser Ala Glu Tyr Asn Tyr Ser Thr Thr Asn Thr Thr Thr Thr
        115                 120                 125

Thr Glu Thr His Thr Trp Ser Asp Ser Thr Lys Val Thr Ile Pro Pro
    130                 135                 140

Lys Thr Tyr Val Glu Ala Ala Tyr Ile Ile Gln Asn Gly Thr Tyr Asn
145                 150                 155                 160

Val Pro Val Asn Val Glu Cys Asp Met Ser Gly Thr Leu Phe Cys Arg
                165                 170                 175

Gly Tyr Arg Asp Gly Ala Leu Ile Ala Ala Val Tyr Val Ser Val Ala
            180                 185                 190

Asp Leu Ala Asp Tyr Asn Pro Asn Leu Asn Leu Thr Asn Lys Gly Asp
        195                 200                 205

Gly Ile Ala His Phe Lys Gly Ser Gly Phe Ile Glu Gly Ala Gln Gly
    210                 215                 220

Leu Arg Ser Ile Ile Gln Val Thr Glu Tyr Pro Leu Asp Asp Asn Lys
225                 230                 235                 240

Gly Arg Ser Thr Pro Ile Thr Tyr Leu Ile Asn Gly Ser Leu Ala Pro
                245                 250                 255

Asn Val Thr Leu Lys Asn Ser Asn Ile Lys Phe Gly Ser Gly Gly Ala
            260                 265                 270

Ser Met Thr Val Tyr Asn Ala Thr Phe Thr Ile Asn Phe Tyr Asn Glu
        275                 280                 285

Gly Glu Trp Gly Gly Pro Glu Pro Tyr Gly Tyr Ile Lys Ala Tyr Leu
    290                 295                 300

Thr Asn Pro Asp His Asp Phe Glu Ile Trp Lys Gln Asp Asp Trp Gly
305                 310                 315                 320

Lys Ser Thr Pro Glu Arg Ser Thr Tyr Thr Gln Thr Ile Lys Ile Ser
                325                 330                 335

Ser Asp Thr Gly Ser Pro Ile Asn Gln Met Cys Phe Tyr Gly Asp Val
            340                 345                 350

Lys Glu Tyr Asp Val Gly Asn Ala Asp Asp Ile Leu Ala Tyr Pro Ser
        355                 360                 365
```

```
Gln Lys Val Cys Ser Thr Pro Gly Val Thr Val Arg Leu Asp Gly Asp
    370                 375                 380

Glu Lys Gly Ser Tyr Val Thr Ile Lys Tyr Ser Leu Thr Pro Ala
385                 390                 395
```

The resulting protein is calculated to comprise the following composition, including the amino acid sequence residues, number of each amino acid residue, and mole percent of each combination of residues of a particular species as set forth in Table 6.

Molecular weight=43792. Residues=399

Isoelectric point=4.53

TABLE 6

Amino Acid Composition of CryET33/CryET34 Fusion [BamHI/NheI (GSGGAS) (SEQ ID NO: 34) Linker

| Residue Type | Number of Residues | Mole Percent In CryET33/34 Protein |
|---|---|---|
| A = Ala | 20 | 5.013 |
| B = Asx | 0 | 0.000 |
| C = Cys | 4 | 1.003 |
| D = Asp | 23 | 5.764 |
| E = Glu | 22 | 5.514 |
| F = Phe | 15 | 3.759 |
| G = Gly | 32 | 8.020 |
| H = His | 4 | 1.003 |
| I = Ile | 25 | 6.266 |
| K = Lys | 22 | 5.514 |
| L = Leu | 16 | 4.010 |
| M = Met | 5 | 1.253 |
| N = Asn | 28 | 7.018 |
| P = Pro | 20 | 5.013 |
| Q = Gln | 11 | 2.757 |
| R = Arg | 7 | 1.754 |
| S = Ser | 33 | 8.271 |
| T = Thr | 52 | 13.033 |

TABLE 6-continued

Amino Acid Composition of CryET33/CryET34 Fusion [BamHI/NheI (GSGGAS) (SEQ ID NO: 34) Linker

| Residue Type | Number of Residues | Mole Percent | In CryET33/34 Protein |
|---|---|---|---|
| V = Val | 30 | 7.519 | |
| W = Trp | 5 | 1.253 | |
| Y = Tyr | 25 | 6.266 | |
| Z = Glx | 0 | 0.000 | |
| A + G | 52 | 13.033 | Non-polar |
| S + T | 85 | 21.303 | Polar |
| D + E | 45 | 11.278 | Acidic |
| D + E + N + Q | 84 | 21.053 | |
| H + K + R | 33 | 8.271 | Basic |
| D + E + H + K + R | 78 | 19.549 | |
| I + L + M + V | 76 | 19.048 | Hydrophobic non-aromatic |
| F + W + Y | 45 | 11.278 | Aromatic |

CryET33/CryET34 Fusion with (GGGS)₃ (SEQ ID NO:35) Linker

The following amino acid sequence, numbered for convenience, represents an example of a CryET33/CryET34 insecticidal protein fusion between CryET33 and CryET34 and containing a Gly-Ser-Gly-Gly-Gly-Ser-Gly-Gly-Gly-Ser-Gly-Gly-Gly-Ser-Ala-Ser (GGGS)₃ (SEQ ID NO: 35) amino acid sequence linker between the two protein sequences. The underlined amino acids at residues numbered from position 268 through position 283 indicate the linker sequence in this novel insecticidal fusion protein.

```
Met Gly Ile Ile Asn Ile Gln Asp Glu Ile Asn Asn Tyr Met Lys Glu   (SEQ ID NO: 12)
1               5                   10                  15

Val Tyr Gly Ala Thr Thr Val Lys Ser Thr Tyr Asp Pro Ser Phe Lys
                20                  25                  30

Val Phe Asn Glu Ser Val Thr Pro Gln Phe Thr Glu Ile Pro Thr Glu
                35                  40                  45

Pro Val Asn Asn Gln Leu Thr Thr Lys Arg Val Asp Asn Thr Gly Ser
50                      55                  60

Tyr Pro Val Glu Ser Thr Val Ser Phe Thr Trp Thr Glu Thr His Thr
65                  70                  75                  80

Glu Thr Ser Ala Val Thr Glu Gly Val Lys Ala Gly Thr Ser Ile Ser
                85                  90                  95

Thr Lys Gln Ser Phe Lys Phe Gly Phe Val Asn Ser Asp Val Thr Leu
                100                 105                 110

Thr Val Ser Ala Glu Tyr Asn Tyr Ser Thr Thr Asn Thr Thr Thr Thr
                115                 120                 125

Thr Glu Thr His Thr Trp Ser Asp Ser Thr Lys Val Thr Ile Pro Pro
                130                 135                 140

Lys Thr Tyr Val Glu Ala Ala Tyr Ile Ile Gln Asn Gly Thr Tyr Asn
145                 150                 155                 160
```

```
                                    -continued
Val Pro Val Asn Val Glu Cys Asp Met Ser Gly Thr Leu Phe Cys Arg
            165                 170                 175

Gly Tyr Arg Asp Gly Ala Leu Ile Ala Ala Val Tyr Val Ser Val Ala
            180                 185                 190

Asp Leu Ala Asp Tyr Asn Pro Asn Leu Asn Leu Thr Asn Lys Gly Asp
            195                 200                 205

Gly Ile Ala His Phe Lys Gly Ser Gly Phe Ile Glu Gly Ala Gln Gly
            210                 215                 220

Leu Arg Ser Val Ile Gln Val Thr Glu Tyr Pro Leu Asp Asp Asn Lys
225                 230                 235                 240

Gly Arg Ser Thr Pro Ile Thr Tyr Leu Ile Asn Gly Ser Leu Ala Pro
            245                 250                 255

Asn Val Thr Leu Lys Asn Ser Asn Ile Lys Phe Gly Ser Gly Gly Gly
            260                 265                 270

Ser Gly Gly Gly Ser Gly Gly Ser Ala Ser Met Thr Val Tyr Asn
            275                 280                 285

Ala Thr Phe Thr Ile Asn Phe Tyr Asn Glu Gly Glu Trp Gly Gly Pro
            290                 295                 300

Glu Pro Tyr Gly Tyr Ile Lys Ala Tyr Leu Thr Asn Pro Asp His Asp
305                 310                 315                 320

Phe Glu Ile Trp Lys Gln Asp Asp Trp Gly Lys Ser Thr Pro Glu Arg
                325                 330                 335

Ser Thr Tyr Thr Gln Thr Ile Lys Ile Ser Ser Asp Thr Gly Ser Pro
            340                 345                 350

Ile Asn Gln Met Cys Phe Tyr Gly Asp Val Lys Glu Tyr Asp Val Gly
            355                 360                 365

Asn Ala Asp Asp Ile Leu Ala Tyr Pro Ser Gln Lys Val Cys Ser Thr
370                 375                 380

Pro Gly Val Thr Val Arg Leu Asp Gly Asp Glu Lys Gly Ser Tyr Val
385                 390                 395                 400

Thr Ile Lys Tyr Ser Leu Thr Pro Ala
            405
```

The resulting protein is calculated to comprise the following composition, including the amino acid sequence residues, number of each amino acid residue, and mole percent of each combination of residues of a particular species as set forth in Table 7.

Molecular weight=44453. Residues=409

Isoelectric point=4.53

TABLE 7

Amino Acid Composition of CryET33/CryET34 [(GGGS)$_3$ (SEQ ID NO: 35) Linker]

| Residue Type | Number of Residues | Mole Percent | In CryET33/34 Protein |
|---|---|---|---|
| A = ALA | 20 | 4.890 | |
| B = Asx | 0 | 0.000 | |
| C = Cys | 4 | 0.978 | |
| D = Asp | 23 | 5.623 | |
| E = Glu | 22 | 5.379 | |
| F = Phe | 15 | 3.667 | |
| G = Gly | 39 | 9.535 | |
| H = His | 4 | 0.978 | |
| I = Ile | 25 | 6.112 | |
| K = Lys | 22 | 5.379 | |
| L = Leu | 16 | 3.912 | |

TABLE 7-continued

Amino Acid Composition of CryET33/CryET34 [(GGGS)$_3$ (SEQ ID NO: 35) Linker]

| Residue Type | Number of Residues | Mole Percent | In CryET33/34 Protein |
|---|---|---|---|
| M = Met | 5 | 1.222 | |
| N = Asn | 28 | 6.846 | |
| P = Pro | 20 | 4.890 | |
| Q = Gln | 11 | 2.689 | |
| R = Arg | 7 | 1.711 | |
| S = Ser | 36 | 8.802 | |
| T = Thr | 52 | 12.714 | |
| V = Val | 30 | 7.335 | |
| W = Trp | 5 | 1.222 | |
| Y = Tyr | 25 | 6.112 | |
| Z = Glx | 0 | 0.000 | |
| A + G | 59 | 14.425 | Non-polar |
| S + T | 88 | 21.516 | Polar |
| D + E | 45 | 11.002 | Acidic |
| D + E + N + Q | 84 | 20.538 | |
| H + K + R | 33 | 8.068 | Basic |
| D + E + H + K + R | 78 | 19.071 | |
| I + L + M + V | 76 | 18.582 | Hydrophobic non-aromatic |
| F + W + Y | 45 | 11.002 | Aromatic |

CryET33/CryET34 Fusion with Lysine Oxidase (PALLKEAPRAEEELPP) (SEQ ID NO:36) Linker The following amino acid sequence, numbered for convenience, represents an example of a CryET33/CryET34 insecticidal protein fusion between CryET33 and CryET34 and containing a lysine oxidase amino acid sequence linker between the two protein sequences. The underlined amino acids at residues numbered from position 268 through position 287 indicate the lysine oxidase linker sequence in this novel insecticidal fusion protein.

```
Met Gly Ile Ile Asn Ile Gln Asp Glu Ile Asn Asn Tyr Met Lys Glu    (SEQ ID N

```
Val Cys Ser Thr Pro Gly Val Thr Val Arg Leu Asp Gly Asp Glu Lys
385                 390                 395                 400

Gly Ser Tyr Val Thr Ile Lys Tyr Ser Leu Thr Pro Ala
                405             410
```

The resulting protein is calculated to comprise the following composition, including the amino acid sequence residues, number of each amino acid residue, and mole percent of each combination of residues of a particular species as set forth in Table 8.

Molecular weight=45420. Residues=413

Isoelectric point=4.51

TABLE 8

Amino Acid Composition CryET33/ET34 Fusion [lysine oxidase (PALLKEAPRAEEELPP) (SEQ ID NO: 36) linker]

| Residue Type | Number of Residues | Mole Percent | In CryET33/34 Protein |
|---|---|---|---|
| A = Ala | 23 | 5.569 | |
| B = Asx | 0 | 0.000 | |
| C = Cys | 4 | 0.969 | |
| D = Asp | 23 | 5.569 | |
| E = Glu | 26 | 6.295 | |
| F = Phe | 15 | 3.632 | |
| G = Gly | 30 | 7.264 | |
| H = His | 4 | 0.969 | |
| I = Ile | 25 | 6.053 | |
| K = Lys | 23 | 5.569 | |
| L = Leu | 19 | 4.600 | |
| M = Met | 5 | 1.211 | |
| N = Asn | 28 | 6.780 | |
| P = Pro | 24 | 5.811 | |
| Q = Gln | 11 | 2.663 | |
| R = Arg | 8 | 1.937 | |
| S = Ser | 33 | 7.990 | |
| T = Thr | 52 | 12.591 | |
| V = Val | 30 | 7.264 | |
| W = Trp | 5 | 1.211 | |
| Y = Tyr | 25 | 6.053 | |
| Z = Glx | 0 | 0.000 | |
| A + G | 53 | 12.833 | Non-polar |
| S + T | 85 | 20.581 | Polar |
| D + E | 49 | 11.864 | Acidic |
| D + E + N + Q | 88 | 21.308 | |
| H + K + R | 35 | 8.475 | Basic |
| D + E + H + K + R | 84 | 20.339 | |
| I + L + M + V | 79 | 19.128 | Hydrophobic non-aromatic |
| F + W + Y | 45 | 10.896 | Aromatic |

Nomenclature of the Novel Proteins

The inventors have arbitrarily assigned the designations tIC100 and tIC101 to the novel proteins, and tIC100 and tIC101 to the novel nucleic acid sequences encoding the respective polypeptides. Formal assignment of gene and protein designations based on the revised nomenclature of crystal protein endotoxins may be assigned by a committee on the nomenclature of *B. thuringiensis*, formed to systematically classify *B. thuringiensis* crystal proteins. The inventors contemplate that the official nomenclature assigned to these sequences will supercede the arbitrarily assigned designations of the present invention.

Transformed Host Cells and Transgenic Plants

Methods and compositions for transforming a bacterium, a yeast cell, a plant cell, or an entire plant with one or more expression vectors comprising a crystal protein-encoding gene sequence are further aspects of this disclosure. A transgenic bacterium, yeast cell, plant cell or plant derived from such a transformation process or the progeny and seeds from such a transgenic plant are also further embodiments of the invention.

Means for transforming bacteria and yeast cells are well known in the art. Typically, means of transformation are similar to those well known means used to transform other bacteria or yeast such as *E. coli* or *Saccharomyces cerevisiae*. Methods for DNA transformation of plant cells include *Agrobacterium*-mediated plant transformation, protoplast transformation, gene transfer into pollen, injection into reproductive organs, injection into immature embryos and particle bombardment. Each of these methods has distinct advantages and disadvantages. Thus, one particular method of introducing genes into a particular plant strain may not necessarily be the most effective for another plant strain, but it is well known which methods are useful for a particular plant strain.

There are many methods for introducing transforming DNA sequences into cells, but not all are suitable for delivering DNA to plant cells. Suitable methods are believed to include virtually any method by which DNA can be introduced into a cell, such as by *Agrobacterium* infection, direct delivery of DNA such as, for example, by PEG-mediated transformation of protoplasts (Omirulleh et al., 1993), by desiccation/inhibition-mediated DNA uptake, by electroporation, by agitation with silicon carbide fibers, by acceleration of DNA coated particles, etc. In certain embodiments, acceleration methods are preferred and include, for example, microprojectile bombardment and the like.

Technology for introduction of DNA into cells is well-known to those of skill in the art. Four general methods for delivering a gene into cells have been described: (1) chemical methods (Graham and van der Eb, 1973; Zatloukal et al., 1992); (2) physical methods such as microinjection (Capecehi, 1980), electroporation (Wong and Neumann, 1982; Fromm et al., 1985; U.S. Pat. No. 5,384,253) and the gene gun (Johnston and Tang, 1994; Fynan et al., 1993); (3) viral vectors (Clapp, 1993; Lu et al., 1993; Eglitis and Anderson, 1988a; 1988b); and (4) receptor-mediated mechanisms (Curiel et al., 1991; 1992; Wagner et al., 1992).

Electroporation

The application of brief, high-voltage electric pulses to a variety of animal and plant cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of clones genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

The introduction of DNA by means of electroporation is well-known to those of skill in the art. In this method, certain cell wall-degrading enzymes, such as pectin degrading enzymes, are employed to render the target recipient cells more susceptible to transformation by electroporation than untreated cells. Alternatively, recipient cells are made more susceptible to transformation, by mechanical wounding. To effect transformation by electroporation one may employ either friable tissues such as a suspension culture of cells, or embryogenic callus, or alternatively, one may transform immature embryos or other organized tissues directly. One would partially degrade the cell walls of the chosen cells by exposing them to pectin-degrading enzymes (pectolyases) or mechanically wounding in a controlled manner. Such cells would then be recipient to DNA transfer by electroporation, which may be carried out at this stage, and transformed cells then identified by a suitable selection or screening protocol dependent on the nature of the newly incorporated DNA.

Microprojectile Bombardment

A further advantageous method for delivering transforming DNA sequences to plant cells is microprojectile bombardment. In this method, particles may be coated with nucleic acids and delivered into cells by a propelling force. Exemplary particles include those comprised of tungsten, gold, platinum, and the like.

An advantage of microprojectile bombardment, in addition to it being an effective means of reproducibly stably transforming monocots, is that neither the isolation of protoplasts (Cristou et al., 1988) nor the susceptibility to *Agrobacterium* infection is required. An illustrative embodiment of a method for delivering DNA into maize cells by acceleration is a Biolistics Particle Delivery System, which can be used to propel particles coated with DNA or cells through a screen, such as a stainless steel or Nytex screen, onto a filter surface covered with corn cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing damage inflicted on the recipient cells by projectiles that are too large.

For the bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus which express the exogenous gene product 48 hours post-bombardment often range from 1 to 10 and average 1 to 3.

In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of immature embryos.

Accordingly, it is contemplated that one may wish to adjust various of the bombardment parameters in small scale studies to fully optimize the conditions. One may particularly wish to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

*Agrobacterium*-Mediated Transfer

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described (Fraley et al., 1985; Rogers et al., 1987). Further, the integration of the Ti-DNA is a relatively precise process resulting in few rearrangements. The region of DNA to be transferred is defined by the border sequences, and intervening DNA is usually inserted into the plant genome as described (Spielmann et al., 1986; Jorgensen et al., 1987).

Modern *Agrobacterium* transformation vectors are capable of replication in *E. coli* as well as *Agrobacterium*, allowing for convenient manipulations as described (Klee et al., 1985). Moreover, recent technological advances in vectors for *Agrobacterium*-mediated gene transfer have improved the arrangement of genes and restriction sites in the vectors to facilitate construction of vectors capable of expressing various polypeptide coding genes. The vectors described (Rogers et al., 1987), have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

*Agrobacterium*-mediated transformation of leaf disks and other tissues such as cotyledons and hypocotyls appears to be limited to plants that *Agrobacterium* naturally infects. *Agrobacterium*-mediated transformation is most efficient in dicotyledonous plants. Few monocots appear to be natural hosts for *Agrobacterium*, although transgenic plants have been produced in asparagus using *Agrobacterium* vectors as described (Bytebier et al., 1987). Therefore, commercially important cereal grains such as rice, corn, and wheat must usually be transformed using alternative methods. However, as mentioned above, the transformation of asparagus using *Agrobacterium* can also be achieved (see, for example, Bytebier et al., 1987). Recently, Jinjiang et al. (U.S. Pat. No. 6,037,522; 2000) disclosed a method for efficient *Agrobacterium* mediated transformation of monocots.

A transgenic plant regenerated from *Agrobacterium* mediated transformation methods typically contains a single simple insert on one chromosome. Such transgenic plants can be referred to as being heterozygous for the added insert, and for coding sequences contained within the insert. However, inasmuch as use of the word "heterozygous" usually implies the presence of a complementary sequence at the same locus of the second chromosome of a pair of chromosomes, and there is no such sequence in a plant containing a single simple insert, it is believed that a more accurate name for such a plant is an independent segregant, because the added, exogenous single simple insert segregates independently during mitosis and meiosis.

More preferred is a transgenic plant that is homozygous for the added structural coding sequence; i.e., a transgenic plant that contains two or more coding sequences artificially introduced using transgenic methods, for example by *Agrobacterium* mediated transformation, one coding sequence at the same locus on each chromosome of a chromosome pair. A homozygous transgenic plant can be obtained by sexually mating (selfing) an independent segregant transgenic plant that contains a single artificially introduced coding sequence, germinating some of the seed produced and analyzing the resulting plants produced for enhanced carboxylase activity relative to a control (native, non-transgenic) or an independent segregant transgenic plant.

It is to be understood that two different transgenic plants can also be mated to produce offspring that contain two independently segregating added, exogenous coding sequences. Selfing of appropriate progeny can produce plants that are homozygous for both artificially introduced simple insert sequences that encode a polypeptides of interest. Backcrossing to a parental plant and out-crossing with a non-transgenic plant are also contemplated.

Other Transformation Methods

Transformation of plant protoplasts can be achieved using methods based on calcium phosphate precipitation, polyethylene glycol treatment, electroporation, and combinations of these treatments (see, e.g., Potrykus et al., 1985; Lorz et al., 1985; Fromm et al., 1986; Uchimiya et al., 1986; Callis et al., 1987; Marcotte et al., 1988).

Application of these systems to different plant strains depends upon the ability to regenerate that particular plant strain from protoplasts. Illustrative methods for the regeneration of cereals from protoplasts are described (Fujimura et al., 1985; Toriyama et al., 1986; Yamada et al., 1986; Abdullah et al., 1986).

To transform plant strains that cannot be successfully regenerated from protoplasts, other ways to introduce DNA into intact cells or tissues can be utilized. For example, regeneration of cereals from immature embryos or explants can be effected as described (Vasil, 1988). In addition, "particle gun" or high-velocity microprojectile technology can be utilized. (Vasil, 1992).

Using that latter technology, DNA is carried through the cell wall and into the cytoplasm on the surface of small metal particles as described (Klein et al., 1987; Klein et al., 1988; McCabe et al., 1988). The metal particles penetrate through several layers of cells and thus allow the transformation of cells within tissue explants.

Methods for Producing Insect-Resistant Transgenic Plants

By transforming a suitable host cell, such as a plant cell, for example with a sequence encoding a CryET33/CryET34 fusion peptide or a tIC100 and/or tIC101 peptide(s), the expression of the encoded crystal fusion protein (i.e., a bacterial crystal protein or polypeptide having coleopteran-inhibitory activity) can result in the formation of insect-resistant plants.

By way of example, one may utilize an expression vector containing a coding region for a *B. thuringiensis* crystal protein and an appropriate selectable marker to transform a suspension of embryonic plant cells, such as wheat or corn cells using a method such as particle bombardment (Maddock et al., 1991; Vasil et al., 1992) to deliver the DNA coated on microprojectiles into the recipient cells. Transgenic plants are then regenerated from transformed embryonic calli that express the insect inhibitory proteins.

The formation of transgenic plants may also be accomplished using other methods of cell transformation which are known in the art such as *Agrobacterium*-mediated DNA transfer (Fraley et al., 1983; Jinjiang et al., 2000). Alternatively, DNA can be introduced into plants by direct DNA transfer into pollen (Zhou et al., 1983; Hess, 1987; Luo et al., 1988), by injection of the DNA into reproductive organs of a plant (Pena et al., 1987), or by direct injection of DNA into the cells of immature embryos followed by the rehydration of desiccated embryos (Neuhaus et al., 1987; Benbrook et al., 1986).

The regeneration, development, and cultivation of plants from single plant protoplast transformants or from various transformed explants is well known in the art (Weissbach and Weissbach, 1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a polypeptide of interest introduced by *Agrobacterium* from leaf explants can be achieved by methods well known in the art such as described (Horsch et al., 1985). In this procedure, transformants are cultured in the presence of a selection agent and in a medium that induces the regeneration of shoots in the plant strain being transformed as described (Fraley et al., 1983).

This procedure typically produces shoots within two to four months and those shoots are then transferred to an appropriate root-inducing medium containing the selective agent and an antibiotic to prevent bacterial growth. Shoots that rooted in the presence of the selective agent to form plantlets are then transplanted to soil or other media to allow the production of roots. These procedures vary depending upon the particular plant strain employed, such variations being well known in the art.

Preferably, the regenerated plants are self-pollinated to provide homozygous transgenic plants, as discussed before. Otherwise, pollen obtained from the regenerated plants is crossed to seed-grown plants of agronomically important, preferably inbred lines. Conversely, pollen from plants of those important lines is used to pollinate regenerated plants. A transgenic plant of the present invention containing a desired polypeptide is cultivated using methods well known to one skilled in the art.

A transgenic plant of this invention thus has an increased amount of a coding region (e.g., a cry gene) that encodes the Cry polypeptide of interest. A preferred transgenic plant is an independent segregant and can transmit that gene and its activity to its progeny. A more preferred transgenic plant is homozygous for that gene, and transmits that gene to all of its offspring on sexual mating. Seed from a transgenic plant may be grown in the field or greenhouse, and resulting sexually mature transgenic plants are self-pollinated to generate true breeding plants. The progeny from these plants become true breeding lines that are evaluated for, by way of example, increased insect inhibitory capacity against coleopteran insects, preferably in the field, under a range of environmental conditions. The inventors contemplate that the present invention will find particular utility in the creation of transgenic plants of commercial interest including various cotton, potato, soybean, canola, tomato, turf grasses, wheat, corn, rice, barley, oats, a variety of ornamental plants and vegetables, as well as a number of nut- and fruit-bearing trees and plants.

ILLUSTRATIVE EMBODIMENTS

This application discloses novel insecticidal proteins isolatable from *Bacillus thuringiensis* strains of bacterium, and in particular, insecticidal proteins exhibiting Coleopteran insecticidal activity. For the purposes of this disclosure, the phrase "insect inhibitory" should be correlated with the word "insecticidal", and these words and phrases are meant to be used interchangeably herein throughout. A composition comprising one or more of the peptides disclosed herein is considered to be insecticidal, and the term insecticidal, and by analogy "insect inhibitory", is intended to be defined as a protein which, upon ingestion into the digestive system of a target insect, causes morbidity and mortality, in that the target insect, having consumed a quantity of the protein is discouraged from eating further, and preferably the target insect's growth is stunted or reduced, and more preferably the target insect is subjected to drying, desiccation, and death upon eating an amount of a substance containing the insecticidal protein in an amount sufficient to cause growth inhibition, feeding inhibition, rejection of a substance containing the protein as a food source, and preferably death.

An exemplary insecticidal composition comprises a sample which contains, in approximately equimolar concentrations, both of the proteins herein defined as CrytIC100 and CrytIC101, alternatively known as tIC100 and tIC101. These proteins have been identified as being expressible from a nucleotide sequence obtained from *Bacillus thuringiensis* strain EG9328. In the course of identifying *Bacillus thuringiensis* strains which exhibit Coleopteran activity, sequences complementary to the binary toxin composition CryET33 and CryET34 were used as probes and primers for hybridizing to and/or amplifying sequences from B.t. strains exhibiting Coleopteran insecticidal activity. As a result of this hybridization and thermal amplification analysis, several strains were identified as containing DNA sequences which contain sequences exhibiting substantial homology to cryET33 and cryET34 DNA sequences and which provided a template for the thermal amplification reaction which produced one or more bands separable upon agarose gel electrophoresis and ethidium bromide staining similar in size to the operon sequence encoding the CryET33 and CryET34 proteins. It was suspected that these bands all encoded the ET33 and ET34 proteins or homologs thereof. It was surprising that one particular clone isolated from this amplification analysis failed to produce any crystal morphology when transformed into an acrystailiferous strain of B.t. Furthermore, DNA sequence analysis of this particular clone resulted in the identification of a sequence which may have, in evolutionary terms, previously encoded at least two proteins similar but not identical to CryET33 and CryET34. This sequence, and the cryptic operon contained within the sequence, isolated from B.t. strain EG9328, is set forth herein in SEQ ID NO:27. While it is impossible to predict whether throughout evolutionary time there was one or more bases added to the sequence to disrupt the coding sequence of CrytIC100, or whether there were one or more bases that were removed from the sequence to disrupt the coding sequence of CrytIC100, or even whether there was ever a CrytIC100 protein ever produced by a *Bacillus thuringiensis* in nature, the fact remains that removing one of the cytosine residues from nucleotide position 84 through 88 within the cryptic sequence as set forth in SEQ ID NO:27 causes the reading frame from nucleotide position 1 through nucleotide position 804 to shift such that a single open reading frame is created which allows this "corrected" sequence to encode the peptide herein described as tIC100. When expressed along with tIC101, or when tIC100 and tIC101 are present in a sample in approximately equimolar ratios, the combination of the two proteins results in an insecticidal composition, in particular when provided in an orally acceptable diet to a Coleopteran target insect. In particular, the Coleopteran target insect most prevalently affected by the tIC100 and tIC101 composition is a boll weevil insect, which is prevalently found as a pest among cotton crops in the new world, i.e., in North America, Mexico, Central and South America, and Australia. It was also found by the inventors herein that fusions between these two proteins exhibited insecticidal activity when tested against the boll weevil, and that it was irrelevant whether the protein fusion contained CrytIC100 or CrytIC101 at the amino terminus of the fusion protein. It was also determined that it was irrelevant as to which proteolytically susceptible amino acid sequence linker was present and in frame between the two CrytIC proteins, so long as the linker sequence was capable of being cleaved when the fusion protein was ingested in an orally acceptable medium by the boll weevil.

The orally acceptable insect diet or orally administrable diet into which the insecticidal proteins of the present invention are to be incorporated are well known in the art as described herein. These can be any composition which can be orally ingested by the target insect pest taking the form for example, when the proteins or fusions of the present invention are expressed from within a host cell such as a plant, fungal, or bacterial cell, consisting of a cell extract, a cell suspension, a cell homogenate, a cell lysate, a cell supernatant, a cell filtrate, or a cell pellet. In addition, the composition containing the insecticidal protein(s) of the present invention can be formulated into a powder, a dust, a pellet, a granule, a spray, an emulsion, a colloid, or a solution, any of which can be topically applied to a substrate which is or can become an orally ingestible, orally acceptable, or an orally administrable diet for a target insect pest. The formulation can be prepared in a number of ways well known in the art, including but not to be limited to dessication, lyophilization, homogenization, extraction, filtration, centrifugation, sedimentation, or concentration. In any such orally acceptable, orally administrable, or orally ingestible diet intended for consumption by a target insect pest, the protein of the present invention should at least be present in a concentration from about 0.001% of the total weight of the composition to about 99% of the weight of the composition.

In view of the nature of the target pest shown herein to be susceptible to the compositions disclosed herein, it is intended that nucleotide sequences be synthesized for expression of the proteinaceous agents of the present invention in plant cells, and in particular in cotton plant cells. It is well known that *Bacillus thuringiensis* DNA sequences encoding insecticidal proteins are not preferred for expression of the proteins encoded thereby in plants. Instead, it has been demonstrated time and again that the preferred DNA sequences for expression in plants should be artificially synthesized in order to maximize the levels of expression of the insecticidal proteins in plants. Therefore, it has previously been demonstrated that multiple DNA sequences, because of the redundancy of the genetic code, can encode the same or a substantially identical protein encoded by the native DNA sequence, i.e. "native" intended to mean "derived as found in nature, or as found in the genome of *Bacillus thuringiensis*, or in this case, because the coding sequence derived from a plasmid naturally occurring within a particular strain of *Bacillus thuringiensis*". Therefore, the prior art teachings indicating which codons to use when preparing a particular nucleotide sequence for expression of a Bt toxin in plants have been extensively referred to and those disclosures, well known in the art, are intended to be within the scope of this invention.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Construction of CryET33/CryET34 Insect Inhibitory Fusion Protein

This example illustrates the construction of a DNA sequence encoding a CryET33 and CryET34 insect inhibitory fusion protein.

CryET33 and CryET34 peptides and nucleic acid sequences encoding these novel peptides have been disclosed previously, at least in U.S. Pat. No. 6,063,756. In order to determine whether a CryET33/CryET34 fusion can be expressed as a single protein and retain bioactivity against boll weevil, a CryET33/CryET34 fusion was constructed based on the wild-type *Bacillus thuringiensis* sequences encoding the CryET33 and CryET34 peptides. An expression construct in pMON47407, a *Bacillus thuringiensis* universal expression vector, was constructed in which the CryET33 coding sequence was downstream of and adjacent to a *Bacillus thuringiensis* sporulation specific promoter at the 5'-end of the construct, and the CryET34 coding sequence was positioned downstream of and adjacent to the CryET33 coding sequence at the 3'-end of the cassette, mimicking the natural orientation within the native B.t. cryET33 and cryET34 operon. A BamHI/NheI linker sequence encoding the amino acid sequence represented by Gly-Ser-Gly-Gly-Ala-Ser (GSGGAS) (SEQ ID NO:34) was introduced in frame between the CryET33 and CryET34 coding sequences to allow for protein flexibility as well as providing a convenient restriction site sequence for introducing other linkers if necessary (see FIG. 1). The sequence encoding the CryET33/CryET34 fusion was constructed using overlapping thermal amplification mutagenesis, and incorporated an SpeI site at the 5'-end and an XhoI site at the 3'-end of the cassette coding sequence. The thermal amplification product was cloned into a pPCR-Script™ vector, and the sequence of the fusion was verified by double-stranded sequencing. The SpeI/XhoI-fragment containing the CryET33/CryET34 fusion peptide coding sequence was cloned into an SpeI/XhoI-digested universal B.t. expression shuttle vector pMON47407 indicated above, creating plasmid pMON38644 for expression of the CryET33/CryET34 fusion protein in B.t. strain EG10650, which is a B.t. strain which is deficient for the production of any insecticidal crystal proteins. The ligation mixture from which pMON38644 was derived was transformed directly into the B.t. expression strain EG10650, and colonies suspected of containing the expected plasmid were chosen for further analysis after selection on appropriate media.

One colony producing a protein of the expected size was selected for further analysis. Plasmid DNA from the transformant was isolated and characterized by restriction enzyme analysis. The EG10650 strain containing the plasmid designated as pMON38644 (strain sIC2000) formed crystal structures upon sporulation. Spores containing these crystal structures were pelleted, washed and subjected to reducing SDS-PAGE analysis, which revealed the presence of a protein of the expected size (43.8 kDa) which exhibited little if any signs of degradation. The CryET33/CryET34 fusion protein crystals were submitted to qualitative bioassay against boll weevil upon solubilization into 10 mM $NaHCO_3$, pH 10.0. Both soluble and insoluble fractions demonstrated bioactivity against boll weevil in a qualitative diet overlay bioassay.

Example 2

Construction of a CryET34/CryET33 Fusion in Orientation Opposite to the Native Operon with Insect Inhibitory Activity This example illustrates the construction of a DNA sequence encoding a CryET34 and CryET33 insect inhibitory fusion protein, and illustrates that the Colepteran inhibitory activity of a fusion protein between CryET33 and CryET34 is independent of the orientation of the two proteins within the fusion.

Figure 2:
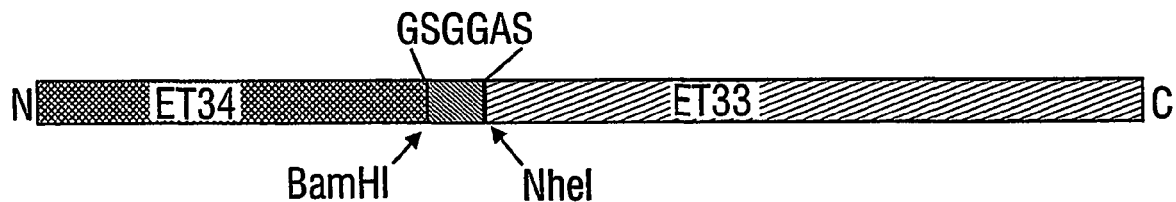
FIG. 2 is a schematic representation of a CryET34/CryET33 or a tIC101/tIC100 fusion protein linked together in frame by a coding sequence flanked by BamHI and NheI restriction sites and encoding a peptide sequence comprising Gly-Ser-Gly-Gly-Ala-Ser (SEQ ID NO:34).

A CryET34/CryET33 fusion protein coding sequence was constructed by synthesizing a nucleic acid sequence having the CryET34 coding sequence located at the 5'-end, and the CryET33 sequence located at the 3'-end. A BamHI/NheI linker coding for GSGGAS was also introduced between the two coding sequences. The sequence encoding the CryET34/CryET33 fusion protein was constructed as in example 1 above (see FIG. 2). The thermal amplification product sequence was cloned into a pPCR-Script™ vector as in example 1, and the sequence was verified by double-stranded sequencing. The SpeI/XhoI-fragment containing the CryET34/CryET33 fusion peptide coding sequence was cloned into an SpeI/XhoI-digested universal Bt. expression vector pMON47407 resulting in the formation of plasmid pMON38646 which is useful for expression of the CryET34/CryET33 fusion protein in the B.t. crystal minus strain EG10650. The pMON38646 ligation mixture was transformed directly into EG10650, and colonies suspected of containing the expected plasmid were chosen for further analysis after selection on the appropriate media. One colony containing a plasmid exhibiting the appropriate characteristics was designated as strain sIC2001.

Growth of strain sIC2001 containing pMON38646 (cryET34/cryET33 fusion) revealed formation of crystal structures upon sporulation. Spores were pelleted, washed and subjected to reducing SDS-PAGE analysis, which revealed the presence of a protein of the expected size (43.8 kDa).

Example 3

Development of ELISA Assay for CryET33/CryET34 Fusion Proteins

This example illustrates the development of an ELISA assay for use in detecting and measuring the amount of a CryET33 and CryET34 fusion protein in a sample.

Figure 3:
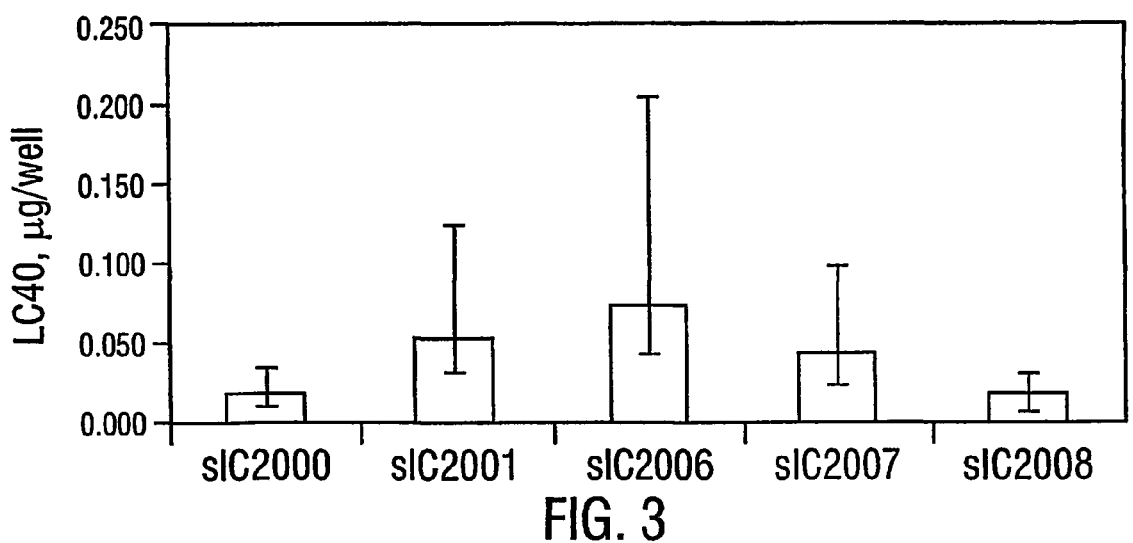
FIG. 3 illustrates the results of a boll-weevil diet-overlay bioassay using a lepidopteran diet containing 0.1% stigmastanol for particular CryET33/CryET34 (sIC200 and sIC2001) and tIC100/tIC101 (sIC2006, sIC2007, and sIC2008) fusions.

An enzyme-linked immuno-sorbent assay was developed to evaluate the expression of CryET33/CryET34 or CryET34/CryET33 fusion proteins in a sample or in an in planta sample. Polyclonal IgG, which had been raised against a combination of both CryET33 and CryET34 proteins, was purified from rabbit serum using Protein A affinity chromatography, and was used as the capture or primary (1°) antibody (Ab). A secondary (2°) antibody capable of binding the 1° antibody was conjugated to an alkaline phosphatase enzyme. A B.t.-expressed CryET33/CryET34 fusion protein was used as standard reference material. A series of 96-well immunoassay plates were loaded using the CryET33/CryET34 fusion protein standard and different combinations of 1° and 2° Ab dilutions. A typical CryET33/CryET34 standard curve is illustrated in FIG. 3. The appropriate dilutions were determined to be 1:500 for 1° Ab and 1:200 for 2° Ab. The assay was tested qualitatively using tobacco plants expressing CryET33/CryET34 fusion protein and the results were confirmed by western blot. These tobacco plants were then analyzed quantitatively and the results were found to be reproducible upon repeating the assay (Table 9). The assay has been used to evaluate expression in tobacco leaf, cotton callus, cotton leaf and cotton square.

TABLE 9

Reproducibility of the CryET33/CryET34 fusion protein ELISA.

| Plant # | Construct | 1-12-2000, ppm | 1-19-2000, ppm |
|---|---|---|---|
| 1705-1 | 51713 | 0.39 | 0.39 |
| 1705-2 | 51713 | 0.23 | 0.18 |
| 1705-3 | 51713 | 0.23 | 0.23 |
| 1705-4 | 51713 | 0.15 | 0.15 |
| 1705-5 | 51713 | 0.46 | 0.42 |
| 1740-1 | 51719 | 1.27 | 1.32 |
| 1740-2 | 51719 | 1.03 | 1.02 |
| 1740-3 | 51719 | 3.15 | 3.21 |
| 1740-4 | 51719 | 1.15 | 1.16 |
| 1740-5 | 51719 | 0.96 | 0.96 |
| 1740-6 | 51719 | 1.29 | 1.35 |
| 1740-7 | 51719 | 1.82 | 1.86 |
| 1740-8 | 51719 | 2.73 | 2.63 |
| 1740-9 | 51719 | 1.64 | 1.60 |
| 1740-10 | 51719 | 1.75 | 1.82 |

Example 4

Expression and Bioactivity of CryET33/CryET34 Fusion Protein in Cotton Callus Tissue In order to quickly evaluate the in planta performance of the CryET33/CryET34 and CryET34/CryET33 fusion proteins, several constructs were made and expressed in cotton callus. In order to address possible folding or stability problems in plants, several parameters were varied. For example, two different linkers were incorporated between the BamHI and NheI restriction sites:

1) $(GGGS)_3$ (SEQ ID NO:35) linker to allow for flexibility at the junction point;

2) Lysine oxidase cleavage site linker which is known to be cleaved in plants. This would allow the two proteins to fold correctly in case the covalent linkage between the C-terminus of one protein and the N-terminus of the other causes steric perturbance.

A chloroplast targeting sequence was also used, as well as various promoters. The constructs submitted for *Agrobacterium*-mediated transformation of cotton callus tissue are listed below in Table 10 (all constructs contained an NPTII selectable marker).

TABLE 10

Plant Transformation Plasmids Containing Various CryET33 and CryET34 Translational Fusions

| | Expression Cassette Description | | | | |
|---|---|---|---|---|---|
| pMON # | Promoter- | ORF1- | Linker- | ORF2- | terminator |
| 51713 | AtEF1a | ET33 | BamHI-NheI | ET34 | E9 |
| 51719 | e35S | ET33 | BamHI-NheI | ET34 | E9 |
| 51739 | e35S | ET33 | $(GGGS)_3$ | ET34 | E9 |
| 51740 | e35S | ET33 | LO | ET34 | E9 |
| 51758 | AtEF1a | ET34 | BamHI-NheI | ET33 | E9 |

Transformed cotton callus tissue was lyophilized and subjected to western blotting. Blots were probed with anti-CryET33/CryET34 antibodies. The results demonstrate that CryET33/CryET34 fusion proteins, with either BamHI/NheI (pMON51713 and 51719), $(GGGS)_3$ (SEQ ID NO:35) (pMON51739) or lysine oxidase (pMON51740) linkers, are expressed in transformed cotton callus as judged by Western blot, and produce the protein band of expected size (about 44 kDa). In this example, the best expressor was tissue transformed with plasmid pMON51719. Very little degradation of the fusion protein to protein fragments corresponding in size to the individual CryET33 (29 kDa) and CryET34 (14 kDa) proteins was observed, indicating the stability of the fusions in cotton callus tissue. A CryET34/CryET33 fusion, constructed in the double border plant transformation plasmid pMON51758, however, did not express any protein detectable by Western blot in cotton callus tissue. The reason for the failure of this construct to express the fusion protein in planta was not readily identifiable. It is believed however, because a CryET34/ET33 fusion produced insecticidal protein of the expected size when expressed from a cassette introduced into EG10650, that successful expression of CryET34/CryET33 fusion protein in cotton callus tissue could easily be achieved without undue experimentation.

The expression levels for CryET33/CryET34 fusion proteins in lyophilized cotton callus tissue as determined by ELISA are summarized in Table 11.

TABLE 11

Expression levels of CryET33/CryET34 fusions in lyophilized cotton callus.

| pMON number | Date of collection | Protein | ET33/34 fusion, mg/g tissue |
|---|---|---|---|
| 51713 | Aug. 12, 1999 | ET33/34 fusion | 7.17 |
| 51713 | Sep. 14, 1999 | ET33/34 fusion | 7.66 |
| 51713 | Oct. 12, 1999 | ET33/34 fusion | 7.95 |
| 51713 | Feb. 11, 2000 | ET33/34 fusion | 5.34 |
| 51713 | Mar. 03, 2000 | ET33/34 fusion | 5.02 |
| 51719 | Jul. 22, 1999 | ET33/34 fusion | 14.01 |
| 51719 | Sep. 23, 1999 | ET33/34 fusion | 15.46 |
| 51719 | Feb. 11, 2000 | ET33/34 fusion | 13.14 |
| 51719 | Mar. 03, 2000 | ET33/34 fusion | 14.53 |
| 51739 | Nov. 16, 1999 | ET33/34 fusion | 18.68 |
| 51739 | Jan. 12, 2000 | ET33/34 fusion | 14.40 |
| 51739 | Feb. 11, 2000 | ET33/34 fusion | 6.15 |
| 51739 | Mar. 03, 2000 | ET33/34 fusion | 5.62 |
| 51740 | Nov. 16, 1999 | ET33/34 fusion | 7.31 |
| 51740 | Jan. 12, 2000 | ET33/34 fusion | 6.51 |
| 51740 | Feb. 11, 2000 | ET33/34 fusion | 2.64 |
| 51740 | Mar. 03, 2000 | ET33/34 fusion | 2.38 |

TABLE 11-continued

Expression levels of CryET33/CryET34 fusions
in lyophilized cotton callus.

| pMON number | Date of collection | Protein | ET33/34 fusion, mg/g tissue |
|---|---|---|---|
| 51758 | Feb. 11, 2000 | ET34/33 fusion | 0.00 |
| 51758 | Mar. 03, 2000 | ET34/33 fusion | 0.00 |

As indicated from the data in Table 11, the highest expression of a CryET33/CryET34 fusion protein was consistently achieved when using pMON51719. This result is consistent with western blotting data.

In order to determine the bioactivity of the lyophilized callus tissues, the transformed callus tissues were tested in a boll weevil diet-overlay bioassay. The results of three independent bioassays, and the expression levels for the lyophilized cotton callus tissues expressing CryET33/CryET34 fusion protein, are shown in Tables 12-14. As indicated from the data in Tables 12-14, callus tissue transformed with plasmid pMON51739 or plasmid pMON51719 consistently demonstrated significant boll weevil activity. In addition, the results shown in Tables 12-14 demonstrate that the transformed tissues exhibiting the greatest boll weevil activity correlated well with elevated expression levels as measured by ELISA, so that expression levels of the fusion proteins could be used to screen for transformation events exhibiting commercial levels of fusion protein expression and coleopteran insect inhibitory bioactivity.

TABLE 12

Boll Weevil Bioactivity of Lyophilized Cotton Callus Tissues
Transformed to Express CryET33/CryET34Fusion Protein

| pMON-date of collection | % Mortality | ELISA, ppm |
|---|---|---|
| 39778* | 0.00 | 0 |
| 51713-Aug. 12, 1999 | 0.00 | 7.17 |
| 51713-Sep. 14, 1999 | 6.25 | 7.66 |
| 51713-Oct. 12, 1999 | 6.67 | 7.95 |
| 51719-Jan. 12, 2000 | 16.67 | 14.01 |
| 51739-Nov. 16, 1999 | 35.29 | 18.68 |
| 51739-Jan. 12, 2000 | 25.00 | 14.4 |
| 51740-Nov. 16, 1999 | 5.88 | 7.31 |
| 51740-Jan. 12, 2000 | 6.25 | 6.51 |

*negative or non-transformed control

TABLE 13

Boll Weevil Bioactivity of Lyophilized Callus Tissues
Transformed to Express CryET33/CryET34

| pMON-date of collection | % Mortality | ELISA, ppm |
|---|---|---|
| 39778* | 0.00 | 0.00 |
| 51713-Feb. 11, 2000 | 0.00 | 5.34 |
| 51713-Mar. 23, 2000 | 0.00 | 5.02 |
| 51719-Feb. 11, 2000 | 31.25 | 13.14 |
| 51719-Mar. 23, 2000 | 40.00 | 14.53 |
| 51739-Feb. 11, 2000 | 6.67 | 6.15 |
| 51739-Mar. 23, 2000 | 0.00 | 5.62 |
| 51740-Feb. 11, 2000 | 0.00 | 2.64 |
| 51740-Mar. 23, 2000 | 6.25 | 2.38 |
| 51758-Feb. 11, 2000 | 0.00 | 0.00 |
| 51758-Mar. 23, 2000 | 6.67 | 0.00 |

*negative control

TABLE 14

Boll Weevil Bioactivity of Lyophilized Callus Tissues
Transformed to Express CryET33/CryET34

| pMON-date of collection | % Mortality | ELISA, ppm |
|---|---|---|
| 39778* | 0.00 | 0 |
| 51713-Aug. 12, 1999 | 6.67 | 5.91 |
| 51713-Sep. 14, 1999 | 7.14 | 7.01 |
| 51713-Oct. 12, 1999 | 0.00 | 7.26 |
| 51713-Mar. 03, 2000 | 0.00 | 5.02 |
| 51719-Jul. 22, 1999 | 25.00 | 10.96 |
| 51719-Sep. 23, 1999 | 26.67 | 11.72 |
| 51719-Mar. 03, 2000 | 31.25 | 14.53 |
| 51739-Nov. 16, 1999 | 28.57 | 19.47 |
| 51739-Feb. 11, 2000 | 0.00 | 6.15 |
| 51739-Mar. 03, 2000 | 0.00 | 5.62 |
| 51740-Nov. 16, 1999 | 14.29 | 9.93 |
| 51740-Jan. 12, 2000 | 6.25 | 4.84 |
| 51740-Mar. 03, 2000 | 0.00 | 2.38 |
| 51758-Mar. 03, 2000 | 0.00 | 0 |

*negative control

Example 5

Bioactivity of CryET33/CryET34 Fusion Protein Expressed in Cotton Plants

In order to evaluate expression and bioactivity of CryET33/CryET34 fusion protein in a target plant, pMON51713 and pMON51719 were submitted for cotton transformation and plant regeneration (all constructs contained a NPTII selectable marker).

The expression levels were determined for $R_0$ plants by ELISA in fresh cotton leaf tissue, and then in fresh cotton squares. Several plants were determined to express levels of CryET33/CryET34 fusion protein above $LC_{50}$ values for CryET33/CryET34 fusion protein (1-5 ppm). These results are presented in Table 15.

TABLE 15

Expression of CryET33/CryET34 fusion protein in fresh cotton tissue*

| Plant (pMON-plant number) | ELISA value in leaf tissue, ppm | ELISA value in square tissue, ppm |
|---|---|---|
| 51713-S011036 | 3.40 | 2.27 |
| 51719-S011132 | 8.22 | 19.59 |
| 51719-S011154 | 5.52 | 1.39 |
| 51719-S011207 | 4.93 | 1.53 |
| 51719-S011339 | 8.94 | ND |
| 51719-S011470 | 7.90 | ND |
| 51719-S011482 | 6.43 | ND |
| 51719-S011480 | 6.13 | ND |
| 51719-S011481 | 5.44 | ND |
| 51719-S011664 | 8.22 | ND |
| 51719-S011875 | 13.97 | ND |
| 51719-S012091 | 6.28 | ND |
| 51719-S012253 | 6.53 | ND |

*(cotton leaf and cotton square tissues were sampled)

Bioactivity of cotton squares expressing CryET33/CryET34 fusion protein against boll weevil for several available plants was tested using lyophilized tissue in diet-overlay bioassay is (3% callus tissue in Agar). The results for plant S011132 are presented in Table 16, which demonstrates that plant S011132 (pMON51719, ET33/ET34 fusion with BamHI/NheI linker driven by e35S promoter) exhibits commercial levels of activity against boll weevil. The results further suggest the CryET33/CryET34 fusion proteins can be highly efficacious in cotton squares which are the primary targets of boll weevil infestation.

TABLE 16

CryET33/CryET34 Fusion Protein Bioactivity Against Boll Weevil

| Sample | Mortality, % | Stunting, % |
|---|---|---|
| C312 | 7.7 | 0 |
| 51719-S011132 | 60 | 80.7 |
| ET33/ET34 PPM | 25 | 78.9 |

Lyophilized cotton square tissue from plant S0111132 transformed with pMON51719 and demonstrated to be expressing 15.8 mg CryET33/34 fusion per mg of lyophilized tissue.
C312- Coker 312 background control.
B.t.-purified CryET33/CryET34 fusion protein (at 4 ppm) was mixed with Coker 312 lyophilized cotton callus as a positive control.

Eleven six-week-old R1 plants selected after *Agrobacterium* mediated transformation with the plasmid pMON51719, i.e., containing an insecticidal fusion of CryET33 and CryET34 linked in frame by a GSGGAS (SEQ ID NO:34) linker, were transferred to a growth chamber in which temperature and humidity conditions were precisely controlled. The plants exhibited a random range of expression levels. Two plants were observed to express no detectable insecticidal protein, and one plant was a expressed very low levels of the fusion protein. Four plants Coker C312 non-transgenic plants were used as negative controls. All plants were infested with adults boll weevils on a weekly basis for four weeks. Flaring squares from each plant were collected in individual plastic containers, and dissected after a period of three weeks in order to enumerate the number of larval and adult weevils. In all, each plant was sampled individually five times. Leaf and square tissue samples were obtained at the outset of the experiment and fusion protein levels were determined by ELISA.

The results demonstrated in vivo activity of an ET33/ET34 fusion protein containing a GSGGAS (SEQ ID NO:34) linker against cotton boll weevils. The ELISA data collected from protein fractions from leaf and square tissue samples from each plant tested correlated well with the observed bioactivity of the plants exhibiting the highest ELISA values. Boll retention also correlated well with the observed expression profiles, in that the plants exhibiting the greatest level of fusion protein expression as judged by ELISA were the plants least susceptible to boll drop upon weevil infestation. In this example, in order to mimic or exceed a field level high pressure infestation, the plants were subjected to four independent infestations of adult weevils. This artificial infestation level was much greater than the infestation that would typically be observed under wild infestation conditions.

One undesirable consequence of the expression of this particular ET33/34 fusion in this plant line was an aberrant plant phenotype. The cotton plants expressing the greatest levels of the ET33/ET34 fusion exhibited an obvious uncharacteristic phenotype. Plants exhibiting a lower level of expression had less severe symptoms, however, all plants derived from this transformation event exhibited some level of the observed symptoms. The principal morphological change observed in these plants was a swelling of the stems. In the most extreme cases there was a shorting of the internode distance resulting in slightly shorter stature. There did not seem to be any major impact on plant fertility. The observed phenotype could be specific to this particular transformation event and is likely attributable to the site of insertion of the cassette expressing the transgene.

Example 6

Fusion of tIC100/tIC101 Insect Inhibitory Proteins

The binary insecticidal toxin identified herein and designated as open reading frames producing the proteins tIC100 and tIC101, is derived from *Bacillus thuringiensis* strain EG9328. The native *Bacillus thuringiensis* DNA sequence contained a frame-shift in the coding sequence for the tIC100 protein. This frame-shift was altered by site-directed mutagenesis to produce the coding sequence as set forth in SEQ ID NO:1, which resulted in the generation of an operon which, when expressed in *Bacillus thuringiensis* strain EG10650 from plasmid pIC10000 (strain sIC1000), encodes a Coleopteran-inhibitory product comprising two proteins—tIC100 (29 kDa) and tIC101 (14 kDa).

Therefore, tIC100 is a protein derived from a cryptic *B. thuringiensis* DNA sequence. The cryptic tIC100 coding sequence is a part of an operon containing the tIC101 coding sequence, and is adjacent to and upstream of the coding sequence for tIC101. The cryptic sequence upstream of tIC101 contains the complete coding sequence for tIC100 except that a single guanosine residue at position 84 of the native cryptic tIC100 coding sequence as set forth in SEQ ID NO:27 causes the tIC100 coding sequence to be out of frame. The frameshift was eliminated by removing the single guanosine residue at position 84 to create the novel tIC100 coding sequence as set forth in SEQ ID NO:1. Overlapping thermal amplification mutagenesis was employed to repair the tIC100 reading frame. Four oligonucleotides were synthesized to complete the reconstruction of a functional coding sequence for tIC100. Two reverse complementary primers, SEQ ID NO:28 and SEQ ID NO:29, were synthesized which spanned the target site sequence, i.e., the guanosine residue to be removed from the cryptic B.t. sequence. Two additional primers were synthesized to take advantage of sequences downstream within the cryptic tIC100 coding sequence and upstream of the proposed promoter sequence for the operon. SEQ ID NO:30 is complementary to nucleotide positions 625-639 in tIC100 as shown in SEQ ID NO:1, and was used with SEQ ID NO:28 in a thermal amplification reaction with the cryptic tIC100 as a template to produce a first product which contains the corrected sequence from just upstream of the frameshift correction point or target site sequence to just downstream of a unique PstI site in the tIC100 coding sequence, located at nucleotide positions 247-252 of SEQ ID NO:1. The other oligonucleotide primer, SEQ ID NO:29, was used along with SEQ ID NO:31 in a thermal amplification reaction using the cryptic tIC100 sequence as a template to produce a second product which also contains the corrected sequence at one end and an EcoRI restriction site at the distal end of the product. The two amplification products were then mixed into a third thermal amplification reaction along with primers corresponding to SEQ ID NO:30 and SEQ ID NO:31, denatured and then allowed to anneal, a portion of the annealed products representing one strand of the first product annealed at one end to the complementary end of one strand of the other amplification product. The overlap/annealed sequence from both products represents the reverse complementary sequences of SEQ ID NO:28 and SEQ ID NO:29. Elongation of those sequences in the thermal amplification reaction produced a sequence which was then amplified by the oligos represented by SEQ ID NO:30 and SEQ ID NO:31 to produce a third product, which was purified, digested with PstI and EcoRI and inserted into the native cryptic sequence in place of the native frame-shifted sequence to produce the novel functional sequence encoding the tIC100 and tIC101 coleopteran inhibitory binary toxin peptides.

The amino acid sequence of the tIC100 and tIC101 binary peptide toxin is similar to the amino acid sequence of the CryET33 and CryET34 binary peptide toxin. CryET33 is a comparative counterpart to CrytIC100, and CryET34 is a comparative counterpart to CrytIC101. The amino acid sequence of tIC100 was 74% identical to the amino acid sequence of CryET33, and the amino acid sequence of tIC101 was about 82.5% identical to the amino acid sequence of CryET34. It was postulated that tIC100 and tIC101 may share common structural and functional properties with CryET33 and CryET34 because of the similarity between the amino acid sequences of these proteins and that these proteins would have similar bioactivity. In fact, insect inhibitory assays using tIC100 and tIC101 herein and completed as described in Examples 9 and 10 of U.S. Pat. No. 6,063,756 demonstrated insect inhibitory activity.

In view of the insect inhibitory activity exhibited by the binary toxin protein CrytIC100 and CrytIC101, and the similarities between the CryET33/CryET34 binary toxin protein, it was further postulated that a fusion protein could be constructed in a manner similar to those described in Examples 1 and 2 above. Several fusions were designed and constructed. Two of these fusions were designed similarly to the CryET33/CryET34 fusions. That is, the tIC100 and tIC101 proteins were fused in both orientations (i.e., tIC100-tIC101 and tIC101-tIC100) and separated by a short hydrophilic linker (Gly-Ser-Gly-Gly-Ala-Ser) (SEQ ID NO:34). The nucleic acid sequence encoding the linker is embraced by unique BamHI and NheI endonuclease restriction sites. Two other fusions were designed with a short Gly-Gly linker since this configuration more closely resembles the distance between the tIC100 and tIC101 sequences in the native B.t. operon.

These nucleotide sequences encoding the tIC100/tIC101 fusions were made by overlapping thermal amplification mutagenesis, cloned into the B.t expression vector pMON47407 and expressed in B.t. strain EG10650. Strain numbers have been assigned to these expression strains as indicated in Table 17.

TABLE 17

B.t. strains Containing Plasmids Encoding ET33/ET34 and tIC100/tIC101 Fusions

| Strain number | pMON # | Description of Fusion Expression Cassette |
|---|---|---|
| sIC2000 | 38644 | ET33-GSGGAS-ET34 (SEQ ID NO: 14) |
| sIC2001 | 38646 | ET34-GSGGAS-ET33 (SEQ ID NO: 20) |
| sIC2002 | 38651 | ET33-GSPALLKEAPRAEEELPPAS-ET34 (SEQ ID NO: 18) |
| sIC2003 | 38652 | ET33-(GGGS)$_3$-ET34 (SEQ ID NO: 12) |
| sIC2006 | 38653 | tIC100-GSGGAS-tIC101 (SEQ ID NO: 8) |
| sIC2007 | 38654 | tIC100-GG-tIC101 (SEQ ID NO: 10) |
| sIC2008 | 38655 | tIC101-GG-tIC100 (SEQ ID NO: 6) |
| sIC2010 | 38657 | tIC101-GSGGAS-tIC100 (SEQ ID NO: 33) |

The tIC100/tIC101 fusions were expressed and identified within the spores-crystal fraction of sporulated B.t. expression strains. SDS-PAGE analysis revealed the presence of the band of expected size (44 kDa), which is not present in the host strain (EG10650) alone.

The spores-crystal fraction suspensions of tIC100/tIC101 fusions were quantitated using spot densitometry and submitted for a diet-overlay bioassay against boll weevil in parallel with CryET33/CryET34 fusions. These results are shown in FIG. 3. FIG. 3 demonstrates that the tIC100/tIC101 fusions (sIC2006, sIC2007 and sIC2008) are approximately as active as the CryET33/CryET34 fusions (sIC2000 and sIC2001).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions, methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. Accordingly, the exclusive rights sought to be patented are as described in the claims below.

REFERENCES CITED

| U.S. Pat. No. 4,766,203 | August, 1988 | Krieg et al. | 530/370. |
|---|---|---|---|
| U.S. Pat. No. 4,771,131 | September, 1988 | Hernstadt et al. | 536/27. |
| U.S. Pat. No. 4,797,279 | January, 1989 | Karamata et al. | 424/93. |
| U.S. Pat. No. 4,910,016 | March, 1990 | Gaertner et al. | 424/93. |
| U.S. Pat. No. 4,966,765 | October, 1990 | Payne et al. | 424/93. |
| U.S. Pat. No. 4,996,155 | February, 1991 | Sick et al. | 435/252. |
| U.S. Pat. No. 4,999,192 | March, 1991 | Payne et al. | 424/93. |
| U.S. Pat. No. 5,006,336 | April, 1991 | Payne | 424/93. |
| U.S. Pat. No. 5,024,837 | June, 1991 | Donovan et al. | 424/93. |
| U.S. Pat. No. 5,071,654 | December, 1991 | English | 424/405. |
| U.S. Pat. No. 5,143,905 | September, 1992 | Sivasubramanian et al. | 514/21. |
| U.S. Pat. No. 5,173,409 | December, 1992 | Englsih | 435/71. |
| U.S. Pat. No. 5,187,091 | February, 1993 | Donovan et al. | 435/240. |
| U.S. Pat. No. 5,264,364 | November, 1993 | Donovan et al. | 435/252. |
| U.S. Pat. No. 5,286,486 | February, 1994 | Payne et al. | 424/93. |
| U.S. Pat. No. 5,338,544 | August, 1994 | Donovan | 424/93. |
| U.S. Pat. No. 5,356,623 | October, 1994 | von Tersch et al. | 424/93. |
| U.S. Pat. No. 5,378,625 | January, 1995 | Donovan et al. | 435/252. |
| U.S. Pat. No. 5,382,429 | January, 1995 | Donovan et al. | 424/94. |
| U.S. Pat. No. 5,384,253 | January, 1995 | Krzyzek et al. | 435/172. |
| U.S. Pat. No. 5,441,884 | August, 1995 | Baum | 435/252. |
| U.S. Pat. No. 6,063,756 | May, 2000 | Donovan et al. | 514/2. |
| U.S. Pat. No. 6,083,499 | July, 2000 | Narva et al. | 424/93. |
| U.S. Pat. No. 6,037,522 | March, 2000 | Jinjiang et al. | 800/287. |

FOREIGN PATENT DOCUMENTS

| 0318143 A2 | October, 1988 | EP. |
|---|---|---|
| 0324254 A1 | December, 1988 | EP. |
| 0382990 A1 | February, 1989 | EP. |
| WO89/07605 | August, 1989 | WO. |
| WO90/13651 | November, 1990 | WO. |
| WO91/07481 | May, 1991 | WO. |
| WO91/14778 | October, 1991 | WO. |
| WO92/13954 | August, 1992 | WO. |
| WO94/13785 | June, 1994 | WO. |
| WO94/16079 | July, 1994 | WO. |
| WO95/02693 | January, 1995 | WO. |

-continued

| | | |
|---|---|---|
| WO95/06730 | March, 1995 | WO |
| WO95/30752 | November, 1995 | WO |
| WO95/30753 | November, 1995 | WO |
| WO95/35378 | December, 1995 | WO |
| WO00/066742 | November, 2000 | WO |
| WO01/14417(A2) | March, 2001 | WO |

OTHER REFERENCES

Cidaria et al., "A novel strain of *Bacillus thuringiensis* (NCIMB 40152) active against coleopteran insects," FEMS Microbiology Letters, 81:129-134, 1991.

Cody et al., "Purification and Crystallization of Insecticidal δ-Endotoxin CyrIIIB2 From *Bacillus thuringiensis*," Proteins: Structure, Function and Genetics, 14:324, 1992.

Donovan et al., "Characterization of two genes encoding *Bacillus thuringiensis* insecticidal crystal proteins toxic to coleopteran species," Applied and Environmental Microbiology, 58(12):3921-3927, 1992.

Donovan et al., "Isolation and characterizations of EG2158, a new strain of *Bacillus thuringiensis* toxic to coleopteran larvae, and nucleotide sequence of the toxin gene," Mol Gen Genet, 214:365-372, 1988.

Lambert et al., "A *Bacillus thuringiensis* insecticidal crystal protein with a high activity against members of the family noctuidae," Applied and Environmental Microbiology, 62(1):80-86, 1996.

Lambert et al., "Novel *Bacillus thuringiensis* insecticidal crystal protein with a silent activity against coleopteran larvae," Applied and Environmental Microbiology, 58(8): 2536-2542, 1992.

Lambert et al., "Nucleotide sequence of gene cryIIID encoding a novel coleopteran-active crystal protein from strain BTI109P of *Bacillus thuringiensis* subsp. *kurstaki*," Gene, 110:131-132, 1992.

Sick et al., "Nucleotide sequence of a coleopteran-active toxin gene from a new isolate of *Bacillus thuringiensis* subsp. *tolworthi*," Nucleic Acids Research, 18(5):1305, 1989.

Von Tersch et al., "Membrane-Permeabilizing Activities of *Bacillus thuringiensis* Coleopteran-Active Toxin CryIIIB2 and CryIIIB2 Domain I Peptide," Applied and Environmental Microbiology, 60(10):3711-3717, 1994.

Cooper, Biotechnology and the Law. Deerfield: CBC. vol. 1, pp. 5B-41 through 5B-43, 1992.

Ely, "The engineering of plants to express *Bacillus thuringiensis* δ-endotoxins," In: *Bacillus thuringiensis*, An Environmental Biopesticide: Theory and Practice, Entwistle, et al., Eds., Chichester, Wiley & Sons, pp. 105-124, 1993.

International Search Report dated Feb. 20, 1998 (PCT/US97/17600) (MECO:203P).

Johnson et al., "Insecticidal activity of EG4961, a novel strain of *Bacillus thuringiensis* toxic to larvae and adults of Southern Corn Rootworm (Coleoptera: Chrysomelidae) and Colorado Potato Beetle (Coleoptera: Chrysomelidae)," J. Economic Entomol., 86(2):330-333, 1993.

SEQUENCE LISTING

<160> NUMBER OF SEQ ID NOS: 36

<210> SEQ ID NO 1
<211> LENGTH: 804
<212> TYPE: DNA
<213> ORGANISM: Bacillus thuringiensis
<220> FEATURE:
<221> NAME/KEY: CDS
<222> LOCATION: (1)..(804)
<223> OTHER INFORMATION: tIC100 coding sequence

<400> SEQUENCE: 1

```
atg gga att atc aac att caa gac gaa att aat gac tac atg aaa ggt      48
Met Gly Ile Ile Asn Ile Gln Asp Glu Ile Asn Asp Tyr Met Lys Gly
1               5                   10                  15 atg tat ggt gca aca tct gtt aaa agc act tat gac ccc tca ttc aaa      96
Met Tyr Gly Ala Thr Ser Val Lys Ser Thr Tyr Asp Pro Ser Phe Lys
                20                  25                  30 gta ttt aac gaa tct gtg aca cct caa tat gat gtg att cca aca gaa     144
Val Phe Asn Glu Ser Val Thr Pro Gln Tyr Asp Val Ile Pro Thr Glu
            35                  40                  45 cct gta aat aat cat att act act aaa gta ata gat aat cca ggg act     192
Pro Val Asn Asn His Ile Thr Thr Lys Val Ile Asp Asn Pro Gly Thr
        50                  55                  60 tca gaa gta acc agt aca gta acg ttc aca tgg acg gaa acc gac act     240
Ser Glu Val Thr Ser Thr Val Thr Phe Thr Trp Thr Glu Thr Asp Thr
65                  70                  75                  80 gta acc tct gca gtg act aaa ggg tat aaa gtc ggt ggt tca gta agc     288
Val Thr Ser Ala Val Thr Lys Gly Tyr Lys Val Gly Gly Ser Val Ser
                85                  90                  95
```

| | | | | | | | | | | | | |
|---|---|---|---|---|---|---|---|---|---|---|---|---|
| tca | aaa | gca | act | ttt | aaa | ttt | gct | ttt | gtt | act | tct | gat | gtt | act | gta | 336 |
| Ser | Lys | Ala | Thr | Phe | Lys | Phe | Ala | Phe | Val | Thr | Ser | Asp | Val | Thr | Val | |
| | | | 100 | | | | | 105 | | | | | 110 | | | |

```
tca aaa gca act ttt aaa ttt gct ttt gtt act tct gat gtt act gta       336
Ser Lys Ala Thr Phe Lys Phe Ala Phe Val Thr Ser Asp Val Thr Val
            100                 105                 110 act gta tca gca gaa tat aat tat agt aca aca gaa aca aca aca aaa       384
Thr Val Ser Ala Glu Tyr Asn Tyr Ser Thr Thr Glu Thr Thr Thr Lys
            115                 120                 125 aca gat aca cgc aca tgg acg gat tcg acg aca gta aaa gcc cct cca       432
Thr Asp Thr Arg Thr Trp Thr Asp Ser Thr Thr Val Lys Ala Pro Pro
    130                 135                 140 aga act aat gta gaa gtt gca tat att atc caa act gga aat tat aac       480
Arg Thr Asn Val Glu Val Ala Tyr Ile Ile Gln Thr Gly Asn Tyr Asn
145                 150                 155                 160 gtt ccg gtt aat gta gag tct gat atg act gga acg cta ttt tgc aga       528
Val Pro Val Asn Val Glu Ser Asp Met Thr Gly Thr Leu Phe Cys Arg
            165                 170                 175 ggg tat aga gat ggt gca cta att gca gcg gct tat gtt tct ata aca       576
Gly Tyr Arg Asp Gly Ala Leu Ile Ala Ala Ala Tyr Val Ser Ile Thr
            180                 185                 190 gat tta gca gat tac aat cct aat ttg ggt ctt aca aat gaa ggg aat       624
Asp Leu Ala Asp Tyr Asn Pro Asn Leu Gly Leu Thr Asn Glu Gly Asn
    195                 200                 205 ggg gtt gct cat ttt aaa ggt gaa ggt tat ata gag ggt gcg caa ggc       672
Gly Val Ala His Phe Lys Gly Glu Gly Tyr Ile Glu Gly Ala Gln Gly
210                 215                 220 tta aga agc tac att caa gtt aca gaa tat cca gtg gat gat aat ggc       720
Leu Arg Ser Tyr Ile Gln Val Thr Glu Tyr Pro Val Asp Asp Asn Gly
225                 230                 235                 240 aga cat tcg ata cca aaa act tat ata att aaa ggt tca tta gca ccc       768
Arg His Ser Ile Pro Lys Thr Tyr Ile Ile Lys Gly Ser Leu Ala Pro
            245                 250                 255 aat gtt act tta ata aat gat aga aag gaa ggt aga                       804
Asn Val Thr Leu Ile Asn Asp Arg Lys Glu Gly Arg
            260                 265
```

<210> SEQ ID NO 2
<211> LENGTH: 268
<212> TYPE: PRT
<213> ORGANISM: Bacillus thuringiensis

<400> SEQUENCE: 2

```
Met Gly Ile Ile Asn Ile Gln Asp Glu Ile Asn Asp Tyr Met Lys Gly
1               5                   10                  15

Met Tyr Gly Ala Thr Ser Val Lys Ser Thr Tyr Asp Pro Ser Phe Lys
            20                  25                  30

Val Phe Asn Glu Ser Val Thr Pro Gln Tyr Asp Val Ile Pro Thr Glu
        35                  40                  45

Pro Val Asn Asn His Ile Thr Lys Val Ile Asp Asn Pro Gly Thr
    50                  55                  60

Ser Glu Val Thr Ser Thr Val Thr Phe Thr Trp Glu Thr Asp Thr
65                  70                  75                  80

Val Thr Ser Ala Val Thr Lys Gly Tyr Lys Val Gly Gly Ser Val Ser
                85                  90                  95

Ser Lys Ala Thr Phe Lys Phe Ala Phe Val Thr Ser Asp Val Thr Val
            100                 105                 110

Thr Val Ser Ala Glu Tyr Asn Tyr Ser Thr Glu Thr Thr Thr Lys
        115                 120                 125

Thr Asp Thr Arg Thr Trp Thr Asp Ser Thr Thr Val Lys Ala Pro Pro
    130                 135                 140
```

```
Arg Thr Asn Val Glu Val Ala Tyr Ile Ile Gln Thr Gly Asn Tyr Asn
145                 150                 155                 160

Val Pro Val Asn Val Glu Ser Asp Met Thr Gly Thr Leu Phe Cys Arg
                165                 170                 175

Gly Tyr Arg Asp Gly Ala Leu Ile Ala Ala Tyr Val Ser Ile Thr
            180                 185                 190

Asp Leu Ala Asp Tyr Asn Pro Asn Leu Gly Leu Thr Asn Glu Gly Asn
                195                 200                 205

Gly Val Ala His Phe Lys Gly Glu Gly Tyr Ile Glu Gly Ala Gln Gly
            210                 215                 220

Leu Arg Ser Tyr Ile Gln Val Thr Glu Tyr Pro Val Asp Asp Asn Gly
225                 230                 235                 240

Arg His Ser Ile Pro Lys Thr Tyr Ile Lys Gly Ser Leu Ala Pro
                245                 250                 255

Asn Val Thr Leu Ile Asn Asp Arg Lys Glu Gly Arg
            260                 265

<210> SEQ ID NO 3
<211> LENGTH: 378
<212> TYPE: DNA
<213> ORGANISM: Bacillus thuringiensis
<220> FEATURE:
<221> NAME/KEY: CDS
<222> LOCATION: (1)..(378)
<223> OTHER INFORMATION: tIC101

<400> SEQUENCE: 3 atg aca gta tat aac gta act ttt acc att aaa ttc tat aat gaa ggt      48
Met Thr Val Tyr Asn Val Thr Phe Thr Ile Lys Phe Tyr Asn Glu Gly
1               5                   10                  15 gaa tgg ggg ggg cca gaa cct tac ggt aag ata tat gca tac ctt caa      96
Glu Trp Gly Gly Pro Glu Pro Tyr Gly Lys Ile Tyr Ala Tyr Leu Gln
                20                  25                  30 aat cca gat cat aat ttc gaa att tgg tca caa gat aat tgg ggg aag     144
Asn Pro Asp His Asn Phe Glu Ile Trp Ser Gln Asp Asn Trp Gly Lys
            35                  40                  45 gat acg cct gag aaa agt tct cac act caa aca att aaa ata agt agc     192
Asp Thr Pro Glu Lys Ser Ser His Thr Gln Thr Ile Lys Ile Ser Ser
50                  55                  60 cca aca ggg ggg cct ata aac caa atg tgt ttt tat ggt gat gta aaa     240
Pro Thr Gly Gly Pro Ile Asn Gln Met Cys Phe Tyr Gly Asp Val Lys
65                  70                  75                  80 gaa tac gac gta gga aat gca gat gat gtt ctc gcc tat cca agt caa     288
Glu Tyr Asp Val Gly Asn Ala Asp Asp Val Leu Ala Tyr Pro Ser Gln
                85                  90                  95 aaa gta tgc agt acg cct ggc aca aca ata agg ctt aac gga gat gag     336
Lys Val Cys Ser Thr Pro Gly Thr Thr Ile Arg Leu Asn Gly Asp Glu
            100                 105                 110 aaa ggt tct tat ata cag att aga tat tcc ttg gcc cca gct             378
Lys Gly Ser Tyr Ile Gln Ile Arg Tyr Ser Leu Ala Pro Ala
        115                 120                 125

<210> SEQ ID NO 4
<211> LENGTH: 126
<212> TYPE: PRT
<213> ORGANISM: Bacillus thuringiensis

<400> SEQUENCE: 4

Met Thr Val Tyr Asn Val Thr Phe Thr Ile Lys Phe Tyr Asn Glu Gly
1               5                   10                  15
```

```
Glu Trp Gly Gly Pro Glu Pro Tyr Gly Lys Ile Tyr Ala Tyr Leu Gln
         20                  25                  30

Asn Pro Asp His Asn Phe Glu Ile Trp Ser Gln Asp Asn Trp Gly Lys
         35                  40                  45

Asp Thr Pro Glu Lys Ser Ser His Thr Gln Thr Ile Lys Ile Ser Ser
         50                  55                  60

Pro Thr Gly Gly Pro Ile Asn Gln Met Cys Phe Tyr Gly Asp Val Lys
65                  70                  75                  80

Glu Tyr Asp Val Gly Asn Ala Asp Asp Val Leu Ala Tyr Pro Ser Gln
                 85                  90                  95

Lys Val Cys Ser Thr Pro Gly Thr Thr Ile Arg Leu Asn Gly Asp Glu
            100                 105                 110

Lys Gly Ser Tyr Ile Gln Ile Arg Tyr Ser Leu Ala Pro Ala
            115                 120                 125

<210> SEQ ID NO 5
<211> LENGTH: 1188
<212> TYPE: DNA
<213> ORGANISM: Artificial sequence
<220> FEATURE:
<223> OTHER INFORMATION: Recombinant fusion protein
<220> FEATURE:
<221> NAME/KEY: CDS
<222> LOCATION: (1)..(1188)
<223> OTHER INFORMATION: tIC101-GG-tIC100 fusion

<400> SEQUENCE: 5 atg aca gta tat aac gta act ttt acc att aaa ttc tat aat gaa ggt      48
Met Thr Val Tyr Asn Val Thr Phe Thr Ile Lys Phe Tyr Asn Glu Gly
1               5                   10                  15 gaa tgg ggg ggg cca gaa cct tac ggt aag ata tat gca tat ctt caa      96
Glu Trp Gly Gly Pro Glu Pro Tyr Gly Lys Ile Tyr Ala Tyr Leu Gln
             20                  25                  30 aat cca gat cat aat ttc gaa att tgg tca caa gat aat tgg ggg aag     144
Asn Pro Asp His Asn Phe Glu Ile Trp Ser Gln Asp Asn Trp Gly Lys
             35                  40                  45 gat acg cct gag aaa agt tct cac act caa aca att aaa ata agt agc     192
Asp Thr Pro Glu Lys Ser Ser His Thr Gln Thr Ile Lys Ile Ser Ser
             50                  55                  60 cca aca ggg ggg cct ata aac caa atg tgt ttt tat ggt gat gta aaa     240
Pro Thr Gly Gly Pro Ile Asn Gln Met Cys Phe Tyr Gly Asp Val Lys
65                  70                  75                  80 gaa tac gac gta gga aat gca gat gat gtt ctc gcc tat cca agt caa     288
Glu Tyr Asp Val Gly Asn Ala Asp Asp Val Leu Ala Tyr Pro Ser Gln
                 85                  90                  95 aaa gta tgc agt acg cct ggc aca aca ata agg ctt aac gga gat gag     336
Lys Val Cys Ser Thr Pro Gly Thr Thr Ile Arg Leu Asn Gly Asp Glu
            100                 105                 110 aaa ggt tct tat ata cag att aga tat tcc ttg gcc cca gct ggt gga     384
Lys Gly Ser Tyr Ile Gln Ile Arg Tyr Ser Leu Ala Pro Ala Gly Gly
            115                 120                 125 atg gga att atc aac att caa gac gaa att aat gac tac atg aaa ggt     432
Met Gly Ile Ile Asn Ile Gln Asp Glu Ile Asn Asp Tyr Met Lys Gly
        130                 135                 140 atg tat ggt gca aca tct gtt aaa agc act tat gac ccc tca ttc aaa     480
Met Tyr Gly Ala Thr Ser Val Lys Ser Thr Tyr Asp Pro Ser Phe Lys
145                 150                 155                 160 gta ttt aac gaa tct gtg aca cct caa tat gat gtg att cca aca gaa     528
Val Phe Asn Glu Ser Val Thr Pro Gln Tyr Asp Val Ile Pro Thr Glu
                165                 170                 175
```

| | | |
|---|---|---|
| cct gta aat aat cat att act act aaa gta ata gat aat cca ggg act<br>Pro Val Asn Asn His Ile Thr Thr Lys Val Ile Asp Asn Pro Gly Thr<br>        180                   185                190 | 576 | |
| tca gaa gta acc agt aca gta acg ttc aca tgg acg gaa acc gac act<br>Ser Glu Val Thr Ser Thr Val Thr Phe Thr Trp Thr Glu Thr Asp Thr<br> 195                 200                205 | 624 | |
| gta acc tct gca gtg act aaa ggg tat aaa gtc ggt ggt tca gta agc<br>Val Thr Ser Ala Val Thr Lys Gly Tyr Lys Val Gly Gly Ser Val Ser<br>210                 215                220 | 672 | |
| tca aaa gca act ttt aaa ttt gct ttt gtt act tct gat gtt act gta<br>Ser Lys Ala Thr Phe Lys Phe Ala Phe Val Thr Ser Asp Val Thr Val<br>225               230              235              240 | 720 | |
| act gta tca gca gaa tat aat tat agt aca aca gaa aca aca aca aaa<br>Thr Val Ser Ala Glu Tyr Asn Tyr Ser Thr Thr Glu Thr Thr Thr Lys<br>               245              250              255 | 768 | |
| aca gat aca cgc aca tgg acg gat tcg acg aca gta aaa gcc cct cca<br>Thr Asp Thr Arg Thr Trp Thr Asp Ser Thr Thr Val Lys Ala Pro Pro<br>            260                265              270 | 816 | |
| aga act aat gta gaa gtt gca tat att atc caa act gga aat tat aac<br>Arg Thr Asn Val Glu Val Ala Tyr Ile Ile Gln Thr Gly Asn Tyr Asn<br>        275                280              285 | 864 | |
| gtt ccg gtt aat gta gag tct gat atg act gga acg cta ttt tgc aga<br>Val Pro Val Asn Val Glu Ser Asp Met Thr Gly Thr Leu Phe Cys Arg<br>290               295              300 | 912 | |
| ggg tat aga gat ggt gca cta att gca gcg gct tat gtt tct ata aca<br>Gly Tyr Arg Asp Gly Ala Leu Ile Ala Ala Ala Tyr Val Ser Ile Thr<br>305               310              315              320 | 960 | |
| gat tta gca gat tac aat cct aat ttg ggt ctt aca aat gaa ggg aat<br>Asp Leu Ala Asp Tyr Asn Pro Asn Leu Gly Leu Thr Asn Glu Gly Asn<br>               325              330              335 | 1008 | |
| ggg gtt gct cat ttt aaa ggt gaa ggt tat ata gag ggt gcg caa ggc<br>Gly Val Ala His Phe Lys Gly Glu Gly Tyr Ile Glu Gly Ala Gln Gly<br>            340                345              350 | 1056 | |
| tta aga agc tac att caa gtt aca gaa tat cca gtg gat gat aat ggc<br>Leu Arg Ser Tyr Ile Gln Val Thr Glu Tyr Pro Val Asp Asp Asn Gly<br>        355                360              365 | 1104 | |
| aga cat tcg ata cca aaa act tat ata att aaa ggt tca tta gca ccc<br>Arg His Ser Ile Pro Lys Thr Tyr Ile Ile Lys Gly Ser Leu Ala Pro<br>370               375              380 | 1152 | |
| aat gtt act tta ata aat gat aga aag gaa ggt aga<br>Asn Val Thr Leu Ile Asn Asp Arg Lys Glu Gly Arg<br>385               390              395 | 1188 | |

<210> SEQ ID NO 6
<211> LENGTH: 396
<212> TYPE: PRT
<213> ORGANISM: Artificial sequence
<220> FEATURE:
<223> OTHER INFORMATION: Synthetic Construct

<400> SEQUENCE: 6

Met Thr Val Tyr Asn Val Thr Phe Thr Ile Lys Phe Tyr Asn Glu Gly
1               5                   10                  15

Glu Trp Gly Gly Pro Glu Pro Tyr Gly Lys Ile Tyr Ala Tyr Leu Gln
                20                  25                  30

Asn Pro Asp His Asn Phe Glu Ile Trp Ser Gln Asp Asn Trp Gly Lys
            35                  40                  45

Asp Thr Pro Glu Lys Ser Ser His Thr Gln Thr Ile Lys Ile Ser Ser
        50                  55                  60

```
Pro Thr Gly Gly Pro Ile Asn Gln Met Cys Phe Tyr Gly Asp Val Lys
 65                  70                  75                  80

Glu Tyr Asp Val Gly Asn Ala Asp Val Leu Ala Tyr Pro Ser Gln
             85                  90                  95

Lys Val Cys Ser Thr Pro Gly Thr Thr Ile Arg Leu Asn Gly Asp Glu
            100                 105                 110

Lys Gly Ser Tyr Ile Gln Ile Arg Tyr Ser Leu Ala Pro Ala Gly Gly
            115                 120                 125

Met Gly Ile Ile Asn Ile Gln Asp Glu Ile Asn Asp Tyr Met Lys Gly
            130                 135                 140

Met Tyr Gly Ala Thr Ser Val Lys Ser Thr Tyr Asp Pro Ser Phe Lys
145                 150                 155                 160

Val Phe Asn Glu Ser Val Thr Pro Gln Tyr Asp Val Ile Pro Thr Glu
                165                 170                 175

Pro Val Asn Asn His Ile Thr Thr Lys Val Ile Asp Asn Pro Gly Thr
            180                 185                 190

Ser Glu Val Thr Ser Thr Val Thr Phe Thr Trp Thr Glu Thr Asp Thr
            195                 200                 205

Val Thr Ser Ala Val Thr Lys Gly Tyr Lys Val Gly Gly Ser Val Ser
210                 215                 220

Ser Lys Ala Thr Phe Lys Phe Ala Phe Val Thr Ser Asp Val Thr Val
225                 230                 235                 240

Thr Val Ser Ala Glu Tyr Asn Tyr Ser Thr Thr Glu Thr Thr Thr Lys
                245                 250                 255

Thr Asp Thr Arg Thr Trp Thr Asp Ser Thr Thr Val Lys Ala Pro Pro
            260                 265                 270

Arg Thr Asn Val Glu Val Ala Tyr Ile Ile Gln Thr Gly Asn Tyr Asn
            275                 280                 285

Val Pro Val Asn Val Glu Ser Asp Met Thr Gly Thr Leu Phe Cys Arg
            290                 295                 300

Gly Tyr Arg Asp Gly Ala Leu Ile Ala Ala Ala Tyr Val Ser Ile Thr
305                 310                 315                 320

Asp Leu Ala Asp Tyr Asn Pro Asn Leu Gly Leu Thr Asn Glu Gly Asn
                325                 330                 335

Gly Val Ala His Phe Lys Gly Glu Gly Tyr Ile Glu Gly Ala Gln Gly
            340                 345                 350

Leu Arg Ser Tyr Ile Gln Val Thr Glu Tyr Pro Val Asp Asp Asn Gly
            355                 360                 365

Arg His Ser Ile Pro Lys Thr Tyr Ile Ile Lys Gly Ser Leu Ala Pro
            370                 375                 380

Asn Val Thr Leu Ile Asn Asp Arg Lys Glu Gly Arg
385                 390                 395

<210> SEQ ID NO 7
<211> LENGTH: 1200
<212> TYPE: DNA
<213> ORGANISM: Artificial sequence
<220> FEATURE:
<223> OTHER INFORMATION: Recombinant fusion protein
<220> FEATURE:
<221> NAME/KEY: CDS
<222> LOCATION: (1)..(1200)
<223> OTHER INFORMATION: tIC100-GSGGAS-tIC101

<400> SEQUENCE: 7 atg gga att atc aac att caa gac gaa att aat gac tac atg aaa ggt    48
Met Gly Ile Ile Asn Ile Gln Asp Glu Ile Asn Asp Tyr Met Lys Gly
```

```
atg tat ggt gca aca tct gtt aaa agc act tat gac ccc tca ttc aaa     96
Met Tyr Gly Ala Thr Ser Val Lys Ser Thr Tyr Asp Pro Ser Phe Lys
            20                  25                  30 gta ttt aac gaa tct gtg aca cct caa tat gat gtg att cca aca gaa    144
Val Phe Asn Glu Ser Val Thr Pro Gln Tyr Asp Val Ile Pro Thr Glu
        35                  40                  45 cct gta aat aat cat att act act aaa gta ata gat aat cca ggg act    192
Pro Val Asn Asn His Ile Thr Thr Lys Val Ile Asp Asn Pro Gly Thr
    50                  55                  60 tca gaa gta acc agt aca gta acg ttc aca tgg acg gaa acc gac act    240
Ser Glu Val Thr Ser Thr Val Thr Phe Thr Trp Thr Glu Thr Asp Thr
65                  70                  75                  80 gta acc tct gca gtg act aaa ggg tat aaa gtc ggt ggt tca gta agc    288
Val Thr Ser Ala Val Thr Lys Gly Tyr Lys Val Gly Gly Ser Val Ser
            85                  90                  95 tca aaa gca act ttt aaa ttt gct ttt gtt act tct gat gtt act gta    336
Ser Lys Ala Thr Phe Lys Phe Ala Phe Val Thr Ser Asp Val Thr Val
            100                 105                 110 act gta tca gca gaa tat aat tat agt aca aca gaa aca aca aca aaa    384
Thr Val Ser Ala Glu Tyr Asn Tyr Ser Thr Thr Glu Thr Thr Thr Lys
        115                 120                 125 aca gat aca cgc aca tgg acg gat tcg acg aca gta aaa gcc cct cca    432
Thr Asp Thr Arg Thr Trp Thr Asp Ser Thr Thr Val Lys Ala Pro Pro
    130                 135                 140 aga act aat gta gaa gtt gca tat att atc caa act gga aat tat aac    480
Arg Thr Asn Val Glu Val Ala Tyr Ile Ile Gln Thr Gly Asn Tyr Asn
145                 150                 155                 160 gtt ccg gtt aat gta gag tct gat atg act gga acg cta ttt tgc aga    528
Val Pro Val Asn Val Glu Ser Asp Met Thr Gly Thr Leu Phe Cys Arg
            165                 170                 175 ggg tat aga gat ggt gca cta att gca gcg gct tat gtt tct ata aca    576
Gly Tyr Arg Asp Gly Ala Leu Ile Ala Ala Ala Tyr Val Ser Ile Thr
            180                 185                 190 gat tta gca gat tac aat cct aat ttg ggt ctt aca aat gaa ggg aat    624
Asp Leu Ala Asp Tyr Asn Pro Asn Leu Gly Leu Thr Asn Glu Gly Asn
        195                 200                 205 ggg gtt gct cat ttt aaa ggt gaa ggt tat ata gag ggt gcg caa ggc    672
Gly Val Ala His Phe Lys Gly Glu Gly Tyr Ile Glu Gly Ala Gln Gly
    210                 215                 220 tta aga agc tac att caa gtt aca gaa tat cca gtg gat gat aat ggc    720
Leu Arg Ser Tyr Ile Gln Val Thr Glu Tyr Pro Val Asp Asp Asn Gly
225                 230                 235                 240 aga cat tcg ata cca aaa act tat ata att aaa ggt tca tta gca ccc    768
Arg His Ser Ile Pro Lys Thr Tyr Ile Ile Lys Gly Ser Leu Ala Pro
            245                 250                 255 aat gtt act tta ata aat gat aga aag gaa ggt aga gga tcc ggt gga    816
Asn Val Thr Leu Ile Asn Asp Arg Lys Glu Gly Arg Gly Ser Gly Gly
            260                 265                 270 gct agc atg aca gta tat aac gta act ttt acc att aaa ttc tat aat    864
Ala Ser Met Thr Val Tyr Asn Val Thr Phe Thr Ile Lys Phe Tyr Asn
        275                 280                 285 gaa ggt gaa tgg ggg gga cca gaa cct tac ggt aag ata tat gca tat    912
Glu Gly Glu Trp Gly Gly Pro Glu Pro Tyr Gly Lys Ile Tyr Ala Tyr
    290                 295                 300 ctt caa aat cca gat cat aat ttc gaa att tgg tca caa gat aat tgg    960
Leu Gln Asn Pro Asp His Asn Phe Glu Ile Trp Ser Gln Asp Asn Trp
305                 310                 315                 320 ggg aag gat acg cct gag aaa agt tct cac act caa aca att aaa ata   1008
```

```
Gly Lys Asp Thr Pro Glu Lys Ser Ser His Thr Gln Thr Ile Lys Ile
                325                 330                 335 agt agc cca aca ggg ggg cct ata aac caa atg tgt ttt tat ggt gat      1056
Ser Ser Pro Thr Gly Gly Pro Ile Asn Gln Met Cys Phe Tyr Gly Asp
            340                 345                 350 gta aaa gaa tac gac gta gga aat gca gat gat gtt ctc gcc tat cca      1104
Val Lys Glu Tyr Asp Val Gly Asn Ala Asp Asp Val Leu Ala Tyr Pro
        355                 360                 365 agt caa aaa gta tgc agt acg cct ggc aca aca ata agg ctt aac gga      1152
Ser Gln Lys Val Cys Ser Thr Pro Gly Thr Thr Ile Arg Leu Asn Gly
    370                 375                 380 gat gag aaa ggt tct tat ata cag att aga tat tcc ttg gcc cca gct      1200
Asp Glu Lys Gly Ser Tyr Ile Gln Ile Arg Tyr Ser Leu Ala Pro Ala
385                 390                 395                 400

<210> SEQ ID NO 8
<211> LENGTH: 400
<212> TYPE: PRT
<213> ORGANISM: Artificial sequence
<220> FEATURE:
<223> OTHER INFORMATION: Synthetic Construct

<400> SEQUENCE: 8

Met Gly Ile Ile Asn Ile Gln Asp Glu Ile Asn Asp Tyr Met Lys Gly
1               5                   10                  15

Met Tyr Gly Ala Thr Ser Val Lys Ser Thr Tyr Asp Pro Ser Phe Lys
            20                  25                  30

Val Phe Asn Glu Ser Val Thr Pro Gln Tyr Asp Val Ile Pro Thr Glu
        35                  40                  45

Pro Val Asn Asn His Ile Thr Thr Lys Val Ile Asp Asn Pro Gly Thr
    50                  55                  60

Ser Glu Val Thr Ser Thr Val Thr Phe Thr Trp Thr Glu Thr Asp Thr
65                  70                  75                  80

Val Thr Ser Ala Val Thr Lys Gly Tyr Lys Val Gly Ser Val Ser
                85                  90                  95

Ser Lys Ala Thr Phe Lys Phe Ala Phe Val Thr Ser Asp Val Thr Val
            100                 105                 110

Thr Val Ser Ala Glu Tyr Asn Tyr Ser Thr Thr Glu Thr Thr Thr Lys
        115                 120                 125

Thr Asp Thr Arg Thr Trp Thr Asp Ser Thr Thr Val Lys Ala Pro Pro
    130                 135                 140

Arg Thr Asn Val Glu Val Ala Tyr Ile Ile Gln Thr Gly Asn Tyr Asn
145                 150                 155                 160

Val Pro Val Asn Val Glu Ser Asp Met Thr Gly Thr Leu Phe Cys Arg
                165                 170                 175

Gly Tyr Arg Asp Gly Ala Leu Ile Ala Ala Tyr Val Ser Ile Thr
            180                 185                 190

Asp Leu Ala Asp Tyr Asn Pro Asn Leu Gly Leu Thr Asn Glu Gly Asn
        195                 200                 205

Gly Val Ala His Phe Lys Gly Glu Gly Tyr Ile Glu Gly Ala Gln Gly
    210                 215                 220

Leu Arg Ser Tyr Ile Gln Val Thr Glu Tyr Pro Val Asp Asn Gly
225                 230                 235                 240

Arg His Ser Ile Pro Lys Thr Tyr Ile Ile Lys Gly Ser Leu Ala Pro
                245                 250                 255

Asn Val Thr Leu Ile Asn Asp Arg Lys Glu Gly Arg Gly Ser Gly Gly
            260                 265                 270
```

```
Ala Ser Met Thr Val Tyr Asn Val Thr Phe Thr Ile Lys Phe Tyr Asn
        275                 280                 285

Glu Gly Glu Trp Gly Gly Pro Glu Pro Tyr Gly Lys Ile Tyr Ala Tyr
    290                 295                 300

Leu Gln Asn Pro Asp His Asn Phe Glu Ile Trp Ser Gln Asp Asn Trp
305                 310                 315                 320

Gly Lys Asp Thr Pro Glu Lys Ser Ser His Thr Gln Thr Ile Lys Ile
                325                 330                 335

Ser Ser Pro Thr Gly Gly Pro Ile Asn Gln Met Cys Phe Tyr Gly Asp
            340                 345                 350

Val Lys Glu Tyr Asp Val Gly Asn Ala Asp Asp Val Leu Ala Tyr Pro
        355                 360                 365

Ser Gln Lys Val Cys Ser Thr Pro Gly Thr Thr Ile Arg Leu Asn Gly
    370                 375                 380

Asp Glu Lys Gly Ser Tyr Ile Gln Ile Arg Tyr Ser Leu Ala Pro Ala
385                 390                 395                 400

<210> SEQ ID NO 9
<211> LENGTH: 1188
<212> TYPE: DNA
<213> ORGANISM: Artificial sequence
<220> FEATURE:
<223> OTHER INFORMATION: Recombinant fusion protein
<220> FEATURE:
<221> NAME/KEY: CDS
<222> LOCATION: (1)..(1188)
<223> OTHER INFORMATION: tIC100-GG-tIC101

<400> SEQUENCE: 9 atg gga att atc aac att caa gac gaa att aat gac tac atg aaa ggt      48
Met Gly Ile Ile Asn Ile Gln Asp Glu Ile Asn Asp Tyr Met Lys Gly
1               5                   10                  15 atg tat ggt gca aca tct gtt aaa agc act tat gac ccc tca ttc aaa      96
Met Tyr Gly Ala Thr Ser Val Lys Ser Thr Tyr Asp Pro Ser Phe Lys
                20                  25                  30 gta ttt aac gaa tct gtg aca cct caa tat gat gtg att cca aca gaa     144
Val Phe Asn Glu Ser Val Thr Pro Gln Tyr Asp Val Ile Pro Thr Glu
            35                  40                  45 cct gta aat aat cat att act act aaa gta ata gat aat cca ggg act     192
Pro Val Asn Asn His Ile Thr Thr Lys Val Ile Asp Asn Pro Gly Thr
        50                  55                  60 tca gaa gta acc agt aca gta acg ttc aca tgg acg gaa acc gac act     240
Ser Glu Val Thr Ser Thr Val Thr Phe Thr Trp Thr Glu Thr Asp Thr
65                  70                  75                  80 gta acc tct gca gtg act aaa ggg tat aaa gtc ggt ggt tca gta agc     288
Val Thr Ser Ala Val Thr Lys Gly Tyr Lys Val Gly Gly Ser Val Ser
                85                  90                  95 tca aaa gca act ttt aaa ttt gct ttt gtt act tct gat gtt act gta     336
Ser Lys Ala Thr Phe Lys Phe Ala Phe Val Thr Ser Asp Val Thr Val
                100                 105                 110 act gta tca gca gaa tat aat tat agt aca aca gaa aca aca aca aaa     384
Thr Val Ser Ala Glu Tyr Asn Tyr Ser Thr Thr Glu Thr Thr Thr Lys
            115                 120                 125 aca gat aca cgc aca tgg acg gat tcg acg aca gta aaa gcc cct cca     432
Thr Asp Thr Arg Thr Trp Thr Asp Ser Thr Thr Val Lys Ala Pro Pro
        130                 135                 140 aga act aat gta gaa gtt gca tat att atc caa act gga aat tat aac     480
Arg Thr Asn Val Glu Val Ala Tyr Ile Ile Gln Thr Gly Asn Tyr Asn
145                 150                 155                 160
```

| | | |
|---|---|---|
| gtt ccg gtt aat gta gag tct gat atg act gga acg cta ttt tgc aga<br>Val Pro Val Asn Val Glu Ser Asp Met Thr Gly Thr Leu Phe Cys Arg<br>              165                        170                      175 | 528 |
| ggg tat aga gat ggt gca cta att gca gcg gct tat gtt tct ata aca<br>Gly Tyr Arg Asp Gly Ala Leu Ile Ala Ala Ala Tyr Val Ser Ile Thr<br>        180                          185                      190 | 576 |
| gat tta gca gat tac aat cct aat ttg ggt ctt aca aat gaa ggg aat<br>Asp Leu Ala Asp Tyr Asn Pro Asn Leu Gly Leu Thr Asn Glu Gly Asn<br>            195                      200                    205 | 624 |
| ggg gtt gct cat ttt aaa ggt gaa ggt tat ata gag ggt gcg caa ggc<br>Gly Val Ala His Phe Lys Gly Glu Gly Tyr Ile Glu Gly Ala Gln Gly<br>210                        215                      220 | 672 |
| tta aga agc tac att caa gtt aca gaa tat cca gtg gat gat aat ggc<br>Leu Arg Ser Tyr Ile Gln Val Thr Glu Tyr Pro Val Asp Asp Asn Gly<br>225                        230                      235                240 | 720 |
| aga cat tcg ata cca aaa act tat ata att aaa ggt tca tta gca ccc<br>Arg His Ser Ile Pro Lys Thr Tyr Ile Ile Lys Gly Ser Leu Ala Pro<br>                      245                      250                    255 | 768 |
| aat gtt act tta ata aat gat aga aag gaa ggt aga ggt gga atg aca<br>Asn Val Thr Leu Ile Asn Asp Arg Lys Glu Gly Arg Gly Gly Met Thr<br>        260                          265                      270 | 816 |
| gta tat aac gta act ttt acc att aaa ttc tat aat gaa ggt gaa tgg<br>Val Tyr Asn Val Thr Phe Thr Ile Lys Phe Tyr Asn Glu Gly Glu Trp<br>            275                      280                    285 | 864 |
| ggg ggg cca gaa cct tac ggt aag ata tat gca tat ctt caa aat cca<br>Gly Gly Pro Glu Pro Tyr Gly Lys Ile Tyr Ala Tyr Leu Gln Asn Pro<br>290                        295                      300 | 912 |
| gat cat aat ttc gaa att tgg tca caa gat aat tgg ggg aag gat acg<br>Asp His Asn Phe Glu Ile Trp Ser Gln Asp Asn Trp Gly Lys Asp Thr<br>305                  310                      315                320 | 960 |
| cct gag aaa agt tct cac act caa aca att aaa ata agt agc cca aca<br>Pro Glu Lys Ser Ser His Thr Gln Thr Ile Lys Ile Ser Ser Pro Thr<br>                      325                      330                    335 | 1008 |
| ggg ggg cct ata aac caa atg tgt ttt tat ggt gat gta aaa gaa tac<br>Gly Gly Pro Ile Asn Gln Met Cys Phe Tyr Gly Asp Val Lys Glu Tyr<br>        340                          345                      350 | 1056 |
| gac gta gga aat gca gat gat gtt ctc gcc tat cca agt caa aaa gta<br>Asp Val Gly Asn Ala Asp Asp Val Leu Ala Tyr Pro Ser Gln Lys Val<br>            355                      360                    365 | 1104 |
| tgc agt acg cct ggc aca aca ata agg ctt aac gga gat gag aaa ggt<br>Cys Ser Thr Pro Gly Thr Thr Ile Arg Leu Asn Gly Asp Glu Lys Gly<br>        370                          375                      380 | 1152 |
| tct tat ata cag att aga tat tcc ttg gcc cca gct<br>Ser Tyr Ile Gln Ile Arg Tyr Ser Leu Ala Pro Ala<br>385                        390                      395 | 1188 |

<210> SEQ ID NO 10
<211> LENGTH: 396
<212> TYPE: PRT
<213> ORGANISM: Artificial sequence
<220> FEATURE:
<223> OTHER INFORMATION: Synthetic Construct

<400> SEQUENCE: 10

Met Gly Ile Ile Asn Ile Gln Asp Glu Ile Asn Asp Tyr Met Lys Gly
1                  5                      10                      15

Met Tyr Gly Ala Thr Ser Val Lys Ser Thr Tyr Asp Pro Ser Phe Lys
                20                      25                      30

Val Phe Asn Glu Ser Val Thr Pro Gln Tyr Asp Val Ile Pro Thr Glu
                  35                        40                      45

Pro Val Asn Asn His Ile Thr Thr Lys Val Ile Asp Asn Pro Gly Thr
    50                  55                  60

Ser Glu Val Thr Ser Thr Val Thr Phe Thr Trp Thr Glu Thr Asp Thr
65                  70                  75                  80

Val Thr Ser Ala Val Thr Lys Gly Tyr Lys Val Gly Gly Ser Val Ser
                85                  90                  95

Ser Lys Ala Thr Phe Lys Phe Ala Phe Val Thr Ser Asp Val Thr Val
            100                 105                 110

Thr Val Ser Ala Glu Tyr Asn Tyr Ser Thr Thr Glu Thr Thr Thr Lys
        115                 120                 125

Thr Asp Thr Arg Thr Trp Thr Asp Ser Thr Thr Val Lys Ala Pro Pro
    130                 135                 140

Arg Thr Asn Val Glu Val Ala Tyr Ile Ile Gln Thr Gly Asn Tyr Asn
145                 150                 155                 160

Val Pro Val Asn Val Glu Ser Asp Met Thr Gly Thr Leu Phe Cys Arg
                165                 170                 175

Gly Tyr Arg Asp Gly Ala Leu Ile Ala Ala Ala Tyr Val Ser Ile Thr
            180                 185                 190

Asp Leu Ala Asp Tyr Asn Pro Asn Leu Gly Leu Thr Asn Glu Gly Asn
        195                 200                 205

Gly Val Ala His Phe Lys Gly Glu Gly Tyr Ile Glu Gly Ala Gln Gly
    210                 215                 220

Leu Arg Ser Tyr Ile Gln Val Thr Glu Tyr Pro Val Asp Asp Asn Gly
225                 230                 235                 240

Arg His Ser Ile Pro Lys Thr Tyr Ile Ile Lys Gly Ser Leu Ala Pro
                245                 250                 255

Asn Val Thr Leu Ile Asn Asp Arg Lys Glu Gly Arg Gly Gly Met Thr
            260                 265                 270

Val Tyr Asn Val Thr Phe Thr Ile Lys Phe Tyr Asn Glu Gly Glu Trp
        275                 280                 285

Gly Gly Pro Glu Pro Tyr Gly Lys Ile Tyr Ala Tyr Leu Gln Asn Pro
    290                 295                 300

Asp His Asn Phe Glu Ile Trp Ser Gln Asp Asn Trp Gly Lys Asp Thr
305                 310                 315                 320

Pro Glu Lys Ser Ser His Thr Gln Thr Ile Lys Ile Ser Ser Pro Thr
                325                 330                 335

Gly Gly Pro Ile Asn Gln Met Cys Phe Tyr Gly Asp Val Lys Glu Tyr
            340                 345                 350

Asp Val Gly Asn Ala Asp Asp Val Leu Ala Tyr Pro Ser Gln Lys Val
        355                 360                 365

Cys Ser Thr Pro Gly Thr Thr Ile Arg Leu Asn Gly Asp Glu Lys Gly
    370                 375                 380

Ser Tyr Ile Gln Ile Arg Tyr Ser Leu Ala Pro Ala
385                 390                 395

<210> SEQ ID NO 11
<211> LENGTH: 1227
<212> TYPE: DNA
<213> ORGANISM: Artificial sequence
<220> FEATURE:
<223> OTHER INFORMATION: Recombinant fusion protein
<220> FEATURE:
<221> NAME/KEY: CDS
<222> LOCATION: (1)..(1227)
<223> OTHER INFORMATION: ET33-(GGGS)3-ET

<400> SEQUENCE: 11

-continued

```
atg ggt atc atc aac att caa gat gag att aac aat tac atg aag gaa      48
Met Gly Ile Ile Asn Ile Gln Asp Glu Ile Asn Asn Tyr Met Lys Glu
 1               5                  10                  15 gtt tac ggt gct act act gtt aag tct act tac gat cct tct ttc aag      96
Val Tyr Gly Ala Thr Thr Val Lys Ser Thr Tyr Asp Pro Ser Phe Lys
             20                  25                  30 gtt ttc aat gaa tct gtt act cct caa ttc act gaa att cct act gaa     144
Val Phe Asn Glu Ser Val Thr Pro Gln Phe Thr Glu Ile Pro Thr Glu
         35                  40                  45 cct gtc aac aac cag ctt act act aag agg gtc gac aat act ggt tct     192
Pro Val Asn Asn Gln Leu Thr Thr Lys Arg Val Asp Asn Thr Gly Ser
     50                  55                  60 tac cct gtt gaa tct act gtt tct ttc act tgg act gaa act cat act     240
Tyr Pro Val Glu Ser Thr Val Ser Phe Thr Trp Thr Glu Thr His Thr
 65                  70                  75                  80 gaa act tct gct gtt act gaa ggt gtt aag gct ggt act tct att tct     288
Glu Thr Ser Ala Val Thr Glu Gly Val Lys Ala Gly Thr Ser Ile Ser
                 85                  90                  95 act aag caa tct ttc aag ttc ggt ttc gtg aac tct gat gtt act ctt     336
Thr Lys Gln Ser Phe Lys Phe Gly Phe Val Asn Ser Asp Val Thr Leu
            100                 105                 110 act gtt tct gct gag tac aac tac tct act act aac act act act act     384
Thr Val Ser Ala Glu Tyr Asn Tyr Ser Thr Thr Asn Thr Thr Thr Thr
        115                 120                 125 act gaa act cat act tgg tct gat tct act aag gtt act att cct cct     432
Thr Glu Thr His Thr Trp Ser Asp Ser Thr Lys Val Thr Ile Pro Pro
    130                 135                 140 aag act tac gtt gaa gct gct tac atc atc cag aat ggt act tac aat     480
Lys Thr Tyr Val Glu Ala Ala Tyr Ile Ile Gln Asn Gly Thr Tyr Asn
145                 150                 155                 160 gtt cct gtt aat gtt gaa tgc gat atg tct ggt act ctg ttc tgt cga     528
Val Pro Val Asn Val Glu Cys Asp Met Ser Gly Thr Leu Phe Cys Arg
                165                 170                 175 ggt tat cgt gat ggt gct ctt att gct gct gtt tac gtt tct gtt gct     576
Gly Tyr Arg Asp Gly Ala Leu Ile Ala Ala Val Tyr Val Ser Val Ala
            180                 185                 190 gat ctt gct gat tac aat cct aat ctt aat ctt act aat aag ggt gat     624
Asp Leu Ala Asp Tyr Asn Pro Asn Leu Asn Leu Thr Asn Lys Gly Asp
        195                 200                 205 ggt att gct cat ttc aag ggt tct gga ttc att gaa ggt gct caa ggt     672
Gly Ile Ala His Phe Lys Gly Ser Gly Phe Ile Glu Gly Ala Gln Gly
    210                 215                 220 ctt aga tct gtg atc caa gtt act gaa tac cct ctt gat gat aat aag     720
Leu Arg Ser Val Ile Gln Val Thr Glu Tyr Pro Leu Asp Asp Asn Lys
225                 230                 235                 240 ggt agg tct act cct att acg tac ctt atc aac ggt tct ctt gct cct     768
Gly Arg Ser Thr Pro Ile Thr Tyr Leu Ile Asn Gly Ser Leu Ala Pro
                245                 250                 255 aat gtt act ctt aag aat tct aat att aag ttc gga tcc ggt gga ggt     816
Asn Val Thr Leu Lys Asn Ser Asn Ile Lys Phe Gly Ser Gly Gly Gly
            260                 265                 270 tcc ggt gga ggt tcc ggt gga ggt tcc gct agc atg act gtg tac aat     864
Ser Gly Gly Gly Ser Gly Gly Gly Ser Ala Ser Met Thr Val Tyr Asn
        275                 280                 285 gct act ttc act atc aac ttt tac aat gaa ggt gaa tgg ggt ggt cct     912
Ala Thr Phe Thr Ile Asn Phe Tyr Asn Glu Gly Glu Trp Gly Gly Pro
    290                 295                 300 gaa cct tac ggt tac atc aag gca tac ctt act aat cct gat cat gat     960
Glu Pro Tyr Gly Tyr Ile Lys Ala Tyr Leu Thr Asn Pro Asp His Asp
```

-continued

```
                    305                 310                 315                 320
ttc gag att tgg aag caa gat gat tgg ggt aag tct act cct gag agg       1008
Phe Glu Ile Trp Lys Gln Asp Asp Trp Gly Lys Ser Thr Pro Glu Arg
                325                 330                 335 tct act tac act caa act att aag ata tct tct gat act ggt tct cct       1056
Ser Thr Tyr Thr Gln Thr Ile Lys Ile Ser Ser Asp Thr Gly Ser Pro
            340                 345                 350 atc aac cag atg tgc ttc tac ggt gac gtc aag gaa tac gat gtc ggc       1104
Ile Asn Gln Met Cys Phe Tyr Gly Asp Val Lys Glu Tyr Asp Val Gly
        355                 360                 365 aac gct gat gat att ctt gct tac cct tct caa aag gtt tgc tct act       1152
Asn Ala Asp Asp Ile Leu Ala Tyr Pro Ser Gln Lys Val Cys Ser Thr
    370                 375                 380 cct ggt gtt act gtt agg ctt gat ggt gat gag aag ggt tct tac gtt       1200
Pro Gly Val Thr Val Arg Leu Asp Gly Asp Glu Lys Gly Ser Tyr Val
385                 390                 395                 400 act att aag tac tct ctt act cct gct                                    1227
Thr Ile Lys Tyr Ser Leu Thr Pro Ala
                405
```

<210> SEQ ID NO 12
<211> LENGTH: 409
<212> TYPE: PRT
<213> ORGANISM: Artificial sequence
<220> FEATURE:
<223> OTHER INFORMATION: Synthetic Construct

<400> SEQUENCE: 12

```
Met Gly Ile Ile Asn Ile Gln Asp Glu Ile Asn Asn Tyr Met Lys Glu
1               5                   10                  15

Val Tyr Gly Ala Thr Thr Val Lys Ser Thr Tyr Asp Pro Ser Phe Lys
            20                  25                  30

Val Phe Asn Glu Ser Val Thr Pro Gln Phe Thr Glu Ile Pro Thr Glu
        35                  40                  45

Pro Val Asn Asn Gln Leu Thr Thr Lys Arg Val Asp Asn Thr Gly Ser
    50                  55                  60

Tyr Pro Val Glu Ser Thr Val Ser Phe Thr Trp Thr Glu Thr His Thr
65                  70                  75                  80

Glu Thr Ser Ala Val Thr Glu Gly Val Lys Ala Gly Thr Ser Ile Ser
                85                  90                  95

Thr Lys Gln Ser Phe Lys Phe Gly Phe Val Asn Ser Asp Val Thr Leu
            100                 105                 110

Thr Val Ser Ala Glu Tyr Asn Tyr Ser Thr Asn Thr Thr Thr Thr
        115                 120                 125

Thr Glu Thr His Thr Trp Ser Asp Ser Thr Lys Val Thr Ile Pro Pro
    130                 135                 140

Lys Thr Tyr Val Glu Ala Ala Tyr Ile Ile Gln Asn Gly Thr Tyr Asn
145                 150                 155                 160

Val Pro Val Asn Val Glu Cys Asp Met Ser Gly Thr Leu Phe Cys Arg
                165                 170                 175

Gly Tyr Arg Asp Gly Ala Leu Ile Ala Ala Val Tyr Val Ser Val Ala
            180                 185                 190

Asp Leu Ala Asp Tyr Asn Pro Asn Leu Asn Leu Thr Asn Lys Gly Asp
        195                 200                 205

Gly Ile Ala His Phe Lys Gly Ser Gly Phe Ile Glu Gly Ala Gln Gly
    210                 215                 220

Leu Arg Ser Val Ile Gln Val Thr Glu Tyr Pro Leu Asp Asp Asn Lys
```

```
                    225                 230                 235                 240

Gly Arg Ser Thr Pro Ile Thr Tyr Leu Ile Asn Gly Ser Leu Ala Pro
                245                 250                 255

Asn Val Thr Leu Lys Asn Ser Asn Ile Lys Phe Gly Ser Gly Gly Gly
                260                 265                 270

Ser Gly Gly Gly Ser Gly Gly Ser Ala Ser Met Thr Val Tyr Asn
            275                 280                 285

Ala Thr Phe Thr Ile Asn Phe Tyr Asn Glu Gly Glu Trp Gly Gly Pro
        290                 295                 300

Glu Pro Tyr Gly Tyr Ile Lys Ala Tyr Leu Thr Asn Pro Asp His Asp
305                 310                 315                 320

Phe Glu Ile Trp Lys Gln Asp Asp Trp Gly Lys Ser Thr Pro Glu Arg
                325                 330                 335

Ser Thr Tyr Thr Gln Thr Ile Lys Ile Ser Ser Asp Thr Gly Ser Pro
                340                 345                 350

Ile Asn Gln Met Cys Phe Tyr Gly Asp Val Lys Glu Tyr Asp Val Gly
                355                 360                 365

Asn Ala Asp Asp Ile Leu Ala Tyr Pro Ser Gln Lys Val Cys Ser Thr
            370                 375                 380

Pro Gly Val Thr Val Arg Leu Asp Gly Asp Glu Lys Gly Ser Tyr Val
385                 390                 395                 400

Thr Ile Lys Tyr Ser Leu Thr Pro Ala
                405
```

```
<210> SEQ ID NO 13
<211> LENGTH: 2397
<212> TYPE: DNA
<213> ORGANISM: Artificial sequence
<220> FEATURE:
<223> OTHER INFORMATION: Recombinant fusion protein
<220> FEATURE:
<221> NAME/KEY: CDS
<222> LOCATION: (1)..(1197)
<223> OTHER INFORMATION: ET33-GSGGAS-ET34

<400> SEQUENCE: 13
```

```
atg aca gta tat aac gta act ttt acc att aaa ttc tat aat gaa ggt      48
Met Thr Val Tyr Asn Val Thr Phe Thr Ile Lys Phe Tyr Asn Glu Gly
1               5                   10                  15 gaa tgg ggg ggg cca gaa cct tac ggt aag ata tat gca tac ctt caa      96
Glu Trp Gly Gly Pro Glu Pro Tyr Gly Lys Ile Tyr Ala Tyr Leu Gln
                20                  25                  30 aat cca gat cat aat ttc gaa att tgg tca caa gat aat tgg ggg aag     144
Asn Pro Asp His Asn Phe Glu Ile Trp Ser Gln Asp Asn Trp Gly Lys
            35                  40                  45 gat acg cct gag aaa agt tct cac act caa aca att aaa ata agt agc     192
Asp Thr Pro Glu Lys Ser Ser His Thr Gln Thr Ile Lys Ile Ser Ser
50                  55                  60 cca aca ggg ggg cct ata aac caa atg tgt ttt tat ggt gat gta aaa     240
Pro Thr Gly Gly Pro Ile Asn Gln Met Cys Phe Tyr Gly Asp Val Lys
65                  70                  75                  80 gaa tac gac gta gga aat gca gat gat gtt ctc gcc tat cca agt caa     288
Glu Tyr Asp Val Gly Asn Ala Asp Asp Val Leu Ala Tyr Pro Ser Gln
                85                  90                  95 aaa gta tgc agt acg cct ggc aca aca ata agg ctt aac gga gat gag     336
Lys Val Cys Ser Thr Pro Gly Thr Thr Ile Arg Leu Asn Gly Asp Glu
                100                 105                 110 aaa ggt tct tat ata cag att aga tat tcc ttg gcc cca gct gga tcc     384
Lys Gly Ser Tyr Ile Gln Ile Arg Tyr Ser Leu Ala Pro Ala Gly Ser
                115                 120                 125
```

-continued

```
                115                 120                 125
ggt gga gct agc atg gga att atc aac att caa gac gaa att aat gac    432
Gly Gly Ala Ser Met Gly Ile Ile Asn Ile Gln Asp Glu Ile Asn Asp
130                 135                 140 tac atg aaa ggt atg tat ggt gca aca tct gtt aaa agc act tat gac    480
Tyr Met Lys Gly Met Tyr Gly Ala Thr Ser Val Lys Ser Thr Tyr Asp
145                 150                 155                 160 ccc tca ttc aaa gta ttt aac gaa tct gtg aca cct caa tat gat gtg    528
Pro Ser Phe Lys Val Phe Asn Glu Ser Val Thr Pro Gln Tyr Asp Val
                165                 170                 175 att cca aca gaa cct gta aat aat cat att act act aaa gta ata gat    576
Ile Pro Thr Glu Pro Val Asn Asn His Ile Thr Thr Lys Val Ile Asp
            180                 185                 190 aat cca ggg act tca gaa gta acc agt aca gta acg ttc aca tgg acg    624
Asn Pro Gly Thr Ser Glu Val Thr Ser Thr Val Thr Phe Thr Trp Thr
        195                 200                 205 gaa acc gac act gta acc tct gca gtg act aaa ggg tat aaa gtc ggt    672
Glu Thr Asp Thr Val Thr Ser Ala Val Thr Lys Gly Tyr Lys Val Gly
210                 215                 220 ggt tca gta agc tca aaa gca act ttt aaa ttt gct ttt gtt act tct    720
Gly Ser Val Ser Ser Lys Ala Thr Phe Lys Phe Ala Phe Val Thr Ser
225                 230                 235                 240 gat gtt act gta act gta tca gca gaa tat aat tat agt aca aca gaa    768
Asp Val Thr Val Thr Val Ser Ala Glu Tyr Asn Tyr Ser Thr Thr Glu
                245                 250                 255 aca aca aca aaa aca gat aca cgc aca tgg acg gat tcg acg aca gta    816
Thr Thr Thr Lys Thr Asp Thr Arg Thr Trp Thr Asp Ser Thr Thr Val
            260                 265                 270 aaa gcc cct cca aga act aat gta gaa gtt gca tat att atc caa act    864
Lys Ala Pro Pro Arg Thr Asn Val Glu Val Ala Tyr Ile Ile Gln Thr
        275                 280                 285 gga aat tat aac gtt ccg gtt aat gta gag tct gat atg act gga acg    912
Gly Asn Tyr Asn Val Pro Val Asn Val Glu Ser Asp Met Thr Gly Thr
290                 295                 300 cta ttt tgc aga ggg tat aga gat ggt gca cta att gca gcg gct tat    960
Leu Phe Cys Arg Gly Tyr Arg Asp Gly Ala Leu Ile Ala Ala Ala Tyr
305                 310                 315                 320 gtt tct ata aca gat tta gca gat tac aat cct aat ttg ggt ctt aca   1008
Val Ser Ile Thr Asp Leu Ala Asp Tyr Asn Pro Asn Leu Gly Leu Thr
                325                 330                 335 aat gaa ggg aat ggg gtt gct cat ttt aaa ggt gaa ggt tat ata gag   1056
Asn Glu Gly Asn Gly Val Ala His Phe Lys Gly Glu Gly Tyr Ile Glu
            340                 345                 350 ggt gcg caa ggc tta aga agc tac att caa gtt aca gaa tat cca gtg   1104
Gly Ala Gln Gly Leu Arg Ser Tyr Ile Gln Val Thr Glu Tyr Pro Val
        355                 360                 365 gat gat aat ggc aga cat tcg ata cca aaa act tat ata att aaa ggt   1152
Asp Asp Asn Gly Arg His Ser Ile Pro Lys Thr Tyr Ile Ile Lys Gly
370                 375                 380 tca tta gca ccc aat gtt act tta ata aat gat aga aag gaa ggt       1197
Ser Leu Ala Pro Asn Val Thr Leu Ile Asn Asp Arg Lys Glu Gly
385                 390                 395 agaatgggaa ttattaatat ccaagatgaa attaataatt acatgaaaga ggtatatggt   1257
gcaacaactg ttaaaagcac atacgatccc tcattcaaag tatttaatga atctgtgaca   1317
ccccaattca ctgaaattcc aacagaacct gtaaataatc aattaactac aaaaagagta   1377
gataatacgg gtagttaccc agtagaaagt actgtatcgt tcacatggac ggaaaccccat   1437 acagaaacaa gtgcagtaac tgagggagtg aaagccggca cctcaataag tactaaacaa   1497
```

-continued

```
tcttttaaat ttggttttgt taactctgat gttactttaa cggtatcagc agaatataat    1557
tatagtacaa caaatacaac tacaacaaca gaaacacaca cctggtcaga ttcaacaaaa    1617
gtaactattc ctcccaaaac ttatgtggag gctgcataca ttatccaaaa tggaacatat    1677
aatgttccgg ttaatgtaga atgtgatatg agtggaactt tattttgtag agggtataga    1737
gatggtgcgc ttattgcagc agtttatgtt tctgtagcgg atttagcaga ttacaatcca    1797
aatttaaatc ttacaaataa aggggatgga attgctcact ttaaaggttc gggttttata    1857
gagggtgcac aaggcttgcg aagcattatt caggttacag aatatccact agatgataat    1917
aaaggtcgct cgacaccaat aacttattta ataaatggtt cattagcacc aaatgttaca    1977
ttaaaaaata gcaacataaa atttggatcc ggtggagcta gcatgacagt atataacgca    2037
actttcacca ttaatttcta taatgaagga gaatgggggg ggccagaacc atatggttat    2097 ataaagcat  atcttacaaa tccagatcat gattttgaaa tttggaaaca agatgattgg    2157
gggaaaagta ctcctgagag aagtacttat acgcaaacga ttaaaataag tagcgacact    2217
ggttccccta taaaccaaat gtgttttat ggtgatgtga aagaatacga cgtaggaaat    2277
gcagatgata ttctcgctta ccaagtcaa aaagtatgca gtacacctgg tgtaacagta    2337
cgacttgatg gcgatgagaa aggttcttat gtgacaatta agtattcctt gactccagca    2397
```

<210> SEQ ID NO 14
<211> LENGTH: 399
<212> TYPE: PRT
<213> ORGANISM: Artificial sequence
<220> FEATURE:
<223> OTHER INFORMATION: Synthetic Construct

<400> SEQUENCE: 14

```
Met Thr Val Tyr Asn Val Thr Phe Thr Ile Lys Phe Tyr Asn Glu Gly
1               5                   10                  15

Glu Trp Gly Gly Pro Glu Pro Tyr Gly Lys Ile Tyr Ala Tyr Leu Gln
            20                  25                  30

Asn Pro Asp His Asn Phe Glu Ile Trp Ser Gln Asp Asn Trp Gly Lys
        35                  40                  45

Asp Thr Pro Glu Lys Ser Ser His Thr Gln Thr Ile Lys Ile Ser Ser
    50                  55                  60

Pro Thr Gly Gly Pro Ile Asn Gln Met Cys Phe Tyr Gly Asp Val Lys
65                  70                  75                  80

Glu Tyr Asp Val Gly Asn Ala Asp Val Leu Ala Tyr Pro Ser Gln
                85                  90                  95

Lys Val Cys Ser Thr Pro Gly Thr Thr Ile Arg Leu Asn Gly Asp Glu
            100                 105                 110

Lys Gly Ser Tyr Ile Gln Ile Arg Tyr Ser Leu Ala Pro Ala Gly Ser
        115                 120                 125

Gly Gly Ala Ser Met Gly Ile Ile Asn Ile Gln Asp Glu Ile Asn Asp
    130                 135                 140

Tyr Met Lys Gly Met Tyr Gly Ala Thr Ser Val Lys Ser Thr Tyr Asp
145                 150                 155                 160

Pro Ser Phe Lys Val Phe Asn Glu Ser Val Thr Pro Gln Tyr Asp Val
                165                 170                 175

Ile Pro Thr Glu Pro Val Asn Asn His Ile Thr Thr Lys Val Ile Asp
            180                 185                 190

Asn Pro Gly Thr Ser Glu Val Ser Thr Val Thr Phe Thr Trp Thr
        195                 200                 205
```

```
Glu Thr Asp Thr Val Thr Ser Ala Val Thr Lys Gly Tyr Lys Val Gly
    210                 215                 220

Gly Ser Val Ser Ser Lys Ala Thr Phe Lys Phe Ala Phe Val Thr Ser
225                 230                 235                 240

Asp Val Thr Val Thr Val Ser Ala Glu Tyr Asn Tyr Ser Thr Thr Glu
                245                 250                 255

Thr Thr Thr Lys Thr Asp Thr Arg Thr Trp Thr Asp Ser Thr Thr Val
            260                 265                 270

Lys Ala Pro Pro Arg Thr Asn Val Glu Val Ala Tyr Ile Ile Gln Thr
        275                 280                 285

Gly Asn Tyr Asn Val Pro Val Asn Val Glu Ser Asp Met Thr Gly Thr
    290                 295                 300

Leu Phe Cys Arg Gly Tyr Arg Asp Gly Ala Leu Ile Ala Ala Ala Tyr
305                 310                 315                 320

Val Ser Ile Thr Asp Leu Ala Asp Tyr Asn Pro Asn Leu Gly Leu Thr
                325                 330                 335

Asn Glu Gly Asn Gly Val Ala His Phe Lys Gly Glu Gly Tyr Ile Glu
            340                 345                 350

Gly Ala Gln Gly Leu Arg Ser Tyr Ile Gln Val Thr Glu Tyr Pro Val
        355                 360                 365

Asp Asp Asn Gly Arg His Ser Ile Pro Lys Thr Tyr Ile Ile Lys Gly
    370                 375                 380

Ser Leu Ala Pro Asn Val Thr Leu Ile Asn Asp Arg Lys Glu Gly
385                 390                 395

<210> SEQ ID NO 15
<211> LENGTH: 1197
<212> TYPE: DNA
<213> ORGANISM: Artificial sequence
<220> FEATURE:
<223> OTHER INFORMATION: Recombinant fusion protein
<220> FEATURE:
<221> NAME/KEY: CDS
<222> LOCATION: (1)..(1197)
<223> OTHER INFORMATION: ET33-GSGGAS-ET34-plant

<400> SEQUENCE: 15 atg ggt atc atc aac att caa gat gag att aac aat tac atg aag gaa      48
Met Gly Ile Ile Asn Ile Gln Asp Glu Ile Asn Asn Tyr Met Lys Glu
1               5                   10                  15 gtt tac ggt gct act act gtt aag tct act tac gat cct tct ttc aag      96
Val Tyr Gly Ala Thr Thr Val Lys Ser Thr Tyr Asp Pro Ser Phe Lys
            20                  25                  30 gtt ttc aat gaa tct gtt act cct caa ttc act gaa att cct act gaa     144
Val Phe Asn Glu Ser Val Thr Pro Gln Phe Thr Glu Ile Pro Thr Glu
        35                  40                  45 cct gtc aac aac cag ctt act act aag agg gtc gac aat act ggt tct     192
Pro Val Asn Asn Gln Leu Thr Thr Lys Arg Val Asp Asn Thr Gly Ser
    50                  55                  60 tac cct gtt gaa tct act gtt tct ttc act tgg act gaa act cat act     240
Tyr Pro Val Glu Ser Thr Val Ser Phe Thr Trp Thr Glu Thr His Thr
65                  70                  75                  80 gaa act tct gct gtt act gaa ggt gtt aag gct ggt act tct att tct     288
Glu Thr Ser Ala Val Thr Glu Gly Val Lys Ala Gly Thr Ser Ile Ser
                85                  90                  95 act aag caa tct ttc aag ttc ggt ttc gtg aac tct gat gtt act ctt     336
Thr Lys Gln Ser Phe Lys Phe Gly Phe Val Asn Ser Asp Val Thr Leu
            100                 105                 110
```

| | | |
|---|---|---|
| act gtt tct gct gag tac aac tac tct act act aac act act act<br>Thr Val Ser Ala Glu Tyr Asn Tyr Ser Thr Thr Asn Thr Thr Thr<br>115                      120                      125 | | 384 |
| act gaa act cat act tgg tct gat tct act aag gtt act att cct cct<br>Thr Glu Thr His Thr Trp Ser Asp Ser Thr Lys Val Thr Ile Pro Pro<br>130                      135                      140 | | 432 |
| aag act tac gtt gaa gct gct tac atc atc cag aat ggt act tac aat<br>Lys Thr Tyr Val Glu Ala Ala Tyr Ile Ile Gln Asn Gly Thr Tyr Asn<br>145                      150                      155                      160 | | 480 |
| gtt cct gtt aat gtt gaa tgc gat atg tct ggt act ctg ttc tgt cga<br>Val Pro Val Asn Val Glu Cys Asp Met Ser Gly Thr Leu Phe Cys Arg<br>                  165                      170                      175 | | 528 |
| ggt tat cgt gat ggt gct ctt att gct gct gtt tac gtt tct gtt gct<br>Gly Tyr Arg Asp Gly Ala Leu Ile Ala Ala Val Tyr Val Ser Val Ala<br>                  180                      185                      190 | | 576 |
| gat ctt gct gat tac aat cct aat ctt aat ctt act aat aag ggt gat<br>Asp Leu Ala Asp Tyr Asn Pro Asn Leu Asn Leu Thr Asn Lys Gly Asp<br>                  195                      200                      205 | | 624 |
| ggt att gct cat ttc aag ggt tct gga ttc att gaa ggt gct caa ggt<br>Gly Ile Ala His Phe Lys Gly Ser Gly Phe Ile Glu Gly Ala Gln Gly<br>210                      215                      220 | | 672 |
| ctt aga tct gtg atc caa gtt act gaa tac cct ctt gat gat aat aag<br>Leu Arg Ser Val Ile Gln Val Thr Glu Tyr Pro Leu Asp Asp Asn Lys<br>225                      230                      235                      240 | | 720 |
| ggt agg tct act cct att acg tac ctt atc aac ggt tct ctt gct cct<br>Gly Arg Ser Thr Pro Ile Thr Tyr Leu Ile Asn Gly Ser Leu Ala Pro<br>                  245                      250                      255 | | 768 |
| aat gtt act ctt aag aat tct aat att aag ttc gga tcc ggt gga gct<br>Asn Val Thr Leu Lys Asn Ser Asn Ile Lys Phe Gly Ser Gly Gly Ala<br>                  260                      265                      270 | | 816 |
| agc atg act gtg tac aat gct act ttc act atc aac ttt tac aat gaa<br>Ser Met Thr Val Tyr Asn Ala Thr Phe Thr Ile Asn Phe Tyr Asn Glu<br>                  275                      280                      285 | | 864 |
| ggt gaa tgg ggt ggt cct gaa cct tac ggt tac atc aag gca tac ctt<br>Gly Glu Trp Gly Gly Pro Glu Pro Tyr Gly Tyr Ile Lys Ala Tyr Leu<br>290                      295                      300 | | 912 |
| act aat cct gat cat gat ttc gag att tgg aag caa gat gat tgg ggt<br>Thr Asn Pro Asp His Asp Phe Glu Ile Trp Lys Gln Asp Asp Trp Gly<br>305                      310                      315                      320 | | 960 |
| aag tct act cct gag agg tct act tac act caa act att aag ata tct<br>Lys Ser Thr Pro Glu Arg Ser Thr Tyr Thr Gln Thr Ile Lys Ile Ser<br>                  325                      330                      335 | | 1008 |
| tct gat act ggt tct cct atc aac cag atg tgc ttc tac ggt gac gtc<br>Ser Asp Thr Gly Ser Pro Ile Asn Gln Met Cys Phe Tyr Gly Asp Val<br>                  340                      345                      350 | | 1056 |
| aag gaa tac gat gtc ggc aac gct gat gat att ctt gct tac cct tct<br>Lys Glu Tyr Asp Val Gly Asn Ala Asp Asp Ile Leu Ala Tyr Pro Ser<br>                  355                      360                      365 | | 1104 |
| caa aag gtt tgc tct act cct ggt gtt act gtt agg ctt gat ggt gat<br>Gln Lys Val Cys Ser Thr Pro Gly Val Thr Val Arg Leu Asp Gly Asp<br>370                      375                      380 | | 1152 |
| gag aag ggt tct tac gtt act att aag tac tct ctt act cct gct<br>Glu Lys Gly Ser Tyr Val Thr Ile Lys Tyr Ser Leu Thr Pro Ala<br>385                      390                      395 | | 1197 |

<210> SEQ ID NO 16
<211> LENGTH: 399
<212> TYPE: PRT
<213> ORGANISM: Artificial sequence
<220> FEATURE:
<223> OTHER INFORMATION: Synthetic Construct

<400> SEQUENCE: 16

```
Met Gly Ile Ile Asn Ile Gln Asp Glu Ile Asn Asn Tyr Met Lys Glu
1               5                   10                  15

Val Tyr Gly Ala Thr Thr Val Lys Ser Thr Tyr Asp Pro Ser Phe Lys
            20                  25                  30

Val Phe Asn Glu Ser Val Thr Pro Gln Phe Thr Glu Ile Pro Thr Glu
        35                  40                  45

Pro Val Asn Asn Gln Leu Thr Thr Lys Arg Val Asp Asn Thr Gly Ser
    50                  55                  60

Tyr Pro Val Glu Ser Thr Val Ser Phe Thr Trp Glu Thr His Thr
65                  70                  75                  80

Glu Thr Ser Ala Val Thr Glu Gly Val Lys Ala Gly Thr Ser Ile Ser
                85                  90                  95

Thr Lys Gln Ser Phe Lys Phe Gly Phe Val Asn Ser Asp Val Thr Leu
            100                 105                 110

Thr Val Ser Ala Glu Tyr Asn Tyr Ser Thr Thr Asn Thr Thr Thr Thr
        115                 120                 125

Thr Glu Thr His Thr Trp Ser Asp Ser Thr Lys Val Thr Ile Pro Pro
    130                 135                 140

Lys Thr Tyr Val Glu Ala Ala Tyr Ile Ile Gln Asn Gly Thr Tyr Asn
145                 150                 155                 160

Val Pro Val Asn Val Glu Cys Asp Met Ser Gly Thr Leu Phe Cys Arg
                165                 170                 175

Gly Tyr Arg Asp Gly Ala Leu Ile Ala Ala Val Tyr Val Ser Val Ala
            180                 185                 190

Asp Leu Ala Asp Tyr Asn Pro Asn Leu Asn Leu Thr Asn Lys Gly Asp
        195                 200                 205

Gly Ile Ala His Phe Lys Gly Ser Gly Phe Ile Glu Gly Ala Gln Gly
    210                 215                 220

Leu Arg Ser Val Ile Gln Val Thr Glu Tyr Pro Leu Asp Asp Asn Lys
225                 230                 235                 240

Gly Arg Ser Thr Pro Ile Thr Tyr Leu Ile Asn Gly Ser Leu Ala Pro
                245                 250                 255

Asn Val Thr Leu Lys Asn Ser Asn Ile Lys Phe Gly Ser Gly Gly Ala
            260                 265                 270

Ser Met Thr Val Tyr Asn Ala Thr Phe Thr Ile Asn Phe Tyr Asn Glu
        275                 280                 285

Gly Glu Trp Gly Gly Pro Glu Pro Tyr Gly Tyr Ile Lys Ala Tyr Leu
    290                 295                 300

Thr Asn Pro Asp His Asp Phe Glu Ile Trp Lys Gln Asp Trp Gly
305                 310                 315                 320

Lys Ser Thr Pro Glu Arg Ser Thr Tyr Thr Gln Thr Ile Lys Ile Ser
                325                 330                 335

Ser Asp Thr Gly Ser Pro Ile Asn Gln Met Cys Phe Tyr Gly Asp Val
            340                 345                 350

Lys Glu Tyr Asp Val Gly Asn Ala Asp Asp Ile Leu Ala Tyr Pro Ser
        355                 360                 365

Gln Lys Val Cys Ser Thr Pro Gly Val Thr Val Arg Leu Asp Gly Asp
    370                 375                 380

Glu Lys Gly Ser Tyr Val Thr Ile Lys Tyr Ser Leu Thr Pro Ala
385                 390                 395
```

```
<210> SEQ ID NO 17
<211> LENGTH: 1239
<212> TYPE: DNA
<213> ORGANISM: Artificial sequence
<220> FEATURE:
<223> OTHER INFORMATION: Recombinant fusion protein
<220> FEATURE:
<221> NAME/KEY: CDS
<222> LOCATION: (1)..(1239)
<223> OTHER INFORMATION: ET33-LO linker-ET34-plant

<400> SEQUENCE: 17
```

| | | | | | | | | | | | | | | | | |
|---|---|---|---|---|---|---|---|---|---|---|---|---|---|---|---|---|
| atg | ggt | atc | atc | aac | att | caa | gat | gag | att | aac | aat | tac | atg | aag | gaa | 48 |
| Met | Gly | Ile | Ile | Asn | Ile | Gln | Asp | Glu | Ile | Asn | Asn | Tyr | Met | Lys | Glu | |
| 1 | | | | 5 | | | | | 10 | | | | | 15 | | |
| gtt | tac | ggt | gct | act | act | gtt | aag | tct | act | tac | gat | cct | tct | ttc | aag | 96 |
| Val | Tyr | Gly | Ala | Thr | Thr | Val | Lys | Ser | Thr | Tyr | Asp | Pro | Ser | Phe | Lys | |
| | | | 20 | | | | | 25 | | | | | 30 | | | |
| gtt | ttc | aat | gaa | tct | gtt | act | cct | caa | ttc | act | gaa | att | cct | act | gaa | 144 |
| Val | Phe | Asn | Glu | Ser | Val | Thr | Pro | Gln | Phe | Thr | Glu | Ile | Pro | Thr | Glu | |
| | | 35 | | | | | 40 | | | | | 45 | | | | |
| cct | gtc | aac | aac | cag | ctt | act | act | aag | agg | gtc | gac | aat | act | ggt | tct | 192 |
| Pro | Val | Asn | Asn | Gln | Leu | Thr | Thr | Lys | Arg | Val | Asp | Asn | Thr | Gly | Ser | |
| | 50 | | | | | 55 | | | | | 60 | | | | | |
| tac | cct | gtt | gaa | tct | act | gtt | tct | ttc | act | tgg | act | gaa | act | cat | act | 240 |
| Tyr | Pro | Val | Glu | Ser | Thr | Val | Ser | Phe | Thr | Trp | Thr | Glu | Thr | His | Thr | |
| 65 | | | | | 70 | | | | | 75 | | | | | 80 | |
| gaa | act | tct | gct | gtt | act | gaa | ggt | gtt | aag | gct | ggt | act | tct | att | tct | 288 |
| Glu | Thr | Ser | Ala | Val | Thr | Glu | Gly | Val | Lys | Ala | Gly | Thr | Ser | Ile | Ser | |
| | | | | 85 | | | | | 90 | | | | | 95 | | |
| act | aag | caa | tct | ttc | aag | ttc | ggt | ttc | gtg | aac | tct | gat | gtt | act | ctt | 336 |
| Thr | Lys | Gln | Ser | Phe | Lys | Phe | Gly | Phe | Val | Asn | Ser | Asp | Val | Thr | Leu | |
| | | | 100 | | | | | 105 | | | | | 110 | | | |
| act | gtt | tct | gct | gag | tac | aac | tac | tct | act | act | aac | act | act | act | act | 384 |
| Thr | Val | Ser | Ala | Glu | Tyr | Asn | Tyr | Ser | Thr | Thr | Asn | Thr | Thr | Thr | Thr | |
| | | 115 | | | | | 120 | | | | | 125 | | | | |
| act | gaa | act | cat | act | tgg | tct | gat | tct | act | aag | gtt | act | att | cct | cct | 432 |
| Thr | Glu | Thr | His | Thr | Trp | Ser | Asp | Ser | Thr | Lys | Val | Thr | Ile | Pro | Pro | |
| | 130 | | | | | 135 | | | | | 140 | | | | | |
| aag | act | tac | gtt | gaa | gct | gct | tac | atc | atc | cag | aat | ggt | act | tac | aat | 480 |
| Lys | Thr | Tyr | Val | Glu | Ala | Ala | Tyr | Ile | Ile | Gln | Asn | Gly | Thr | Tyr | Asn | |
| 145 | | | | | 150 | | | | | 155 | | | | | 160 | |
| gtt | cct | gtt | aat | gtt | gaa | tgc | gat | atg | tct | ggt | act | ctg | ttc | tgt | cga | 528 |
| Val | Pro | Val | Asn | Val | Glu | Cys | Asp | Met | Ser | Gly | Thr | Leu | Phe | Cys | Arg | |
| | | | | 165 | | | | | 170 | | | | | 175 | | |
| ggt | tat | cgt | gat | ggt | gct | ctt | att | gct | gct | gtt | tac | gtt | tct | gtt | gct | 576 |
| Gly | Tyr | Arg | Asp | Gly | Ala | Leu | Ile | Ala | Ala | Val | Tyr | Val | Ser | Val | Ala | |
| | | | 180 | | | | | 185 | | | | | 190 | | | |
| gat | ctt | gct | gat | tac | aat | cct | aat | ctt | aat | ctt | act | aat | aag | ggt | gat | 624 |
| Asp | Leu | Ala | Asp | Tyr | Asn | Pro | Asn | Leu | Asn | Leu | Thr | Asn | Lys | Gly | Asp | |
| | | 195 | | | | | 200 | | | | | 205 | | | | |
| ggt | att | gct | cat | ttc | aag | ggt | tct | gga | ttc | att | gaa | ggt | gct | caa | ggt | 672 |
| Gly | Ile | Ala | His | Phe | Lys | Gly | Ser | Gly | Phe | Ile | Glu | Gly | Ala | Gln | Gly | |
| | 210 | | | | | 215 | | | | | 220 | | | | | |
| ctt | aga | tct | gtg | atc | caa | gtt | act | gaa | tac | cct | ctt | gat | gat | aat | aag | 720 |
| Leu | Arg | Ser | Val | Ile | Gln | Val | Thr | Glu | Tyr | Pro | Leu | Asp | Asp | Asn | Lys | |
| 225 | | | | | 230 | | | | | 235 | | | | | 240 | |
| ggt | agg | tct | act | cct | att | acg | tac | ctt | atc | aac | ggt | tct | ctt | gct | cct | 768 |
| Gly | Arg | Ser | Thr | Pro | Ile | Thr | Tyr | Leu | Ile | Asn | Gly | Ser | Leu | Ala | Pro | |
| | | | | 245 | | | | | 250 | | | | | 255 | | |
| aat | gtt | act | ctt | aag | aat | tct | aat | att | aag | ttc | gga | tcc | cca | gct | ttg | 816 |
| Asn | Val | Thr | Leu | Lys | Asn | Ser | Asn | Ile | Lys | Phe | Gly | Ser | Pro | Ala | Leu | |

```
                260                 265                 270
ctt aag gag gct cca aga gct gag gaa gag ttg cca cca gct agc atg       864
Leu Lys Glu Ala Pro Arg Ala Glu Glu Glu Leu Pro Pro Ala Ser Met
        275                 280                 285 act gtg tac aat gct act ttc act atc aac ttt tac aat gaa ggt gaa       912
Thr Val Tyr Asn Ala Thr Phe Thr Ile Asn Phe Tyr Asn Glu Gly Glu
    290                 295                 300 tgg ggt ggt cct gaa cct tac ggt tac atc aag gca tac ctt act aat       960
Trp Gly Gly Pro Glu Pro Tyr Gly Tyr Ile Lys Ala Tyr Leu Thr Asn
305                 310                 315                 320 cct gat cat gat ttc gag att tgg aag caa gat gat tgg ggt aag tct      1008
Pro Asp His Asp Phe Glu Ile Trp Lys Gln Asp Asp Trp Gly Lys Ser
                325                 330                 335 act cct gag agg tct act tac act caa act att aag ata tct tct gat      1056
Thr Pro Glu Arg Ser Thr Tyr Thr Gln Thr Ile Lys Ile Ser Ser Asp
            340                 345                 350 act ggt tct cct atc aac cag atg tgc ttc tac ggt gac gtc aag gaa      1104
Thr Gly Ser Pro Ile Asn Gln Met Cys Phe Tyr Gly Asp Val Lys Glu
        355                 360                 365 tac gat gtc ggc aac gct gat gat att ctt gct tac cct tct caa aag      1152
Tyr Asp Val Gly Asn Ala Asp Asp Ile Leu Ala Tyr Pro Ser Gln Lys
    370                 375                 380 gtt tgc tct act cct ggt gtt act gtt agg ctt gat ggt gat gag aag      1200
Val Cys Ser Thr Pro Gly Val Thr Val Arg Leu Asp Gly Asp Glu Lys
385                 390                 395                 400 ggt tct tac gtt act att aag tac tct ctt act cct gct                  1239
Gly Ser Tyr Val Thr Ile Lys Tyr Ser Leu Thr Pro Ala
                405                 410

<210> SEQ ID NO 18
<211> LENGTH: 413
<212> TYPE: PRT
<213> ORGANISM: Artificial sequence
<220> FEATURE:
<223> OTHER INFORMATION: Synthetic Construct

<400> SEQUENCE: 18

Met Gly Ile Ile Asn Ile Gln Asp Glu Ile Asn Asn Tyr Met Lys Glu
1               5                   10                  15

Val Tyr Gly Ala Thr Thr Val Lys Ser Thr Tyr Asp Pro Ser Phe Lys
            20                  25                  30

Val Phe Asn Glu Ser Val Thr Pro Gln Phe Thr Glu Ile Pro Thr Glu
        35                  40                  45

Pro Val Asn Asn Gln Leu Thr Thr Lys Arg Val Asp Asn Thr Gly Ser
    50                  55                  60

Tyr Pro Val Glu Ser Thr Val Ser Phe Thr Trp Thr Glu Thr His Thr
65                  70                  75                  80

Glu Thr Ser Ala Val Thr Glu Gly Val Lys Ala Gly Thr Ser Ile Ser
                85                  90                  95

Thr Lys Gln Ser Phe Lys Phe Gly Phe Val Asn Ser Asp Val Thr Leu
            100                 105                 110

Thr Val Ser Ala Glu Tyr Asn Tyr Ser Thr Thr Asn Thr Thr Thr Thr
        115                 120                 125

Thr Glu Thr His Thr Trp Ser Asp Ser Thr Lys Val Thr Ile Pro Pro
    130                 135                 140

Lys Thr Tyr Val Glu Ala Ala Tyr Ile Ile Gln Asn Gly Thr Tyr Asn
145                 150                 155                 160

Val Pro Val Asn Val Glu Cys Asp Met Ser Gly Thr Leu Phe Cys Arg
```

```
                165                 170                 175
Gly Tyr Arg Asp Gly Ala Leu Ile Ala Ala Val Tyr Val Ser Val Ala
            180                 185                 190

Asp Leu Ala Asp Tyr Asn Pro Asn Leu Asn Leu Thr Asn Lys Gly Asp
        195                 200                 205

Gly Ile Ala His Phe Lys Gly Ser Gly Phe Ile Glu Gly Ala Gln Gly
    210                 215                 220

Leu Arg Ser Val Ile Gln Val Thr Glu Tyr Pro Leu Asp Asp Asn Lys
225                 230                 235                 240

Gly Arg Ser Thr Pro Ile Thr Tyr Leu Ile Asn Gly Ser Leu Ala Pro
                245                 250                 255

Asn Val Thr Leu Lys Asn Ser Asn Ile Lys Phe Gly Ser Pro Ala Leu
            260                 265                 270

Leu Lys Glu Ala Pro Arg Ala Glu Glu Leu Pro Pro Ala Ser Met
        275                 280                 285

Thr Val Tyr Asn Ala Thr Phe Thr Ile Asn Phe Tyr Asn Glu Gly Glu
    290                 295                 300

Trp Gly Gly Pro Glu Pro Tyr Gly Tyr Ile Lys Ala Tyr Leu Thr Asn
305                 310                 315                 320

Pro Asp His Asp Phe Glu Ile Trp Lys Gln Asp Asp Trp Gly Lys Ser
                325                 330                 335

Thr Pro Glu Arg Ser Thr Tyr Thr Gln Thr Ile Lys Ile Ser Ser Asp
            340                 345                 350

Thr Gly Ser Pro Ile Asn Gln Met Cys Phe Tyr Gly Asp Val Lys Glu
        355                 360                 365

Tyr Asp Val Gly Asn Ala Asp Asp Ile Leu Ala Tyr Pro Ser Gln Lys
    370                 375                 380

Val Cys Ser Thr Pro Gly Val Thr Val Arg Leu Asp Gly Asp Glu Lys
385                 390                 395                 400

Gly Ser Tyr Val Thr Ile Lys Tyr Ser Leu Thr Pro Ala
                405                 410

<210> SEQ ID NO 19
<211> LENGTH: 1197
<212> TYPE: DNA
<213> ORGANISM: Artificial sequence
<220> FEATURE:
<223> OTHER INFORMATION: Recombinant fusion protein
<220> FEATURE:
<221> NAME/KEY: CDS
<222> LOCATION: (1)..(1197)
<223> OTHER INFORMATION: ET34-GSGGAS-ET33

<400> SEQUENCE: 19 atg aca gta tat aac gca act ttc acc att aat ttc tat aat gaa gga       48
Met Thr Val Tyr Asn Ala Thr Phe Thr Ile Asn Phe Tyr Asn Glu Gly
1               5                   10                  15 gaa tgg ggg ggg cca gaa cca tat ggt tat ata aaa gca tat ctt aca       96
Glu Trp Gly Gly Pro Glu Pro Tyr Gly Tyr Ile Lys Ala Tyr Leu Thr
                20                  25                  30 aat cca gat cat gat ttt gaa att tgg aaa caa gat gat tgg ggg aaa      144
Asn Pro Asp His Asp Phe Glu Ile Trp Lys Gln Asp Asp Trp Gly Lys
            35                  40                  45 agt act cct gag aga agt act tat acg caa acg att aaa ata agt agc      192
Ser Thr Pro Glu Arg Ser Thr Tyr Thr Gln Thr Ile Lys Ile Ser Ser
        50                  55                  60 gac act ggt tcc cct ata aac caa atg tgt ttt tat ggt gat gtg aaa      240
Asp Thr Gly Ser Pro Ile Asn Gln Met Cys Phe Tyr Gly Asp Val Lys
```

-continued

```
                65                  70                  75                  80 gaa tac gac gta gga aat gca gat gat att ctc gct tat cca agt caa        288
Glu Tyr Asp Val Gly Asn Ala Asp Asp Ile Leu Ala Tyr Pro Ser Gln
                85                  90                  95 aaa gta tgc agt aca cct ggt gta aca gta cga ctt gat ggc gat gag        336
Lys Val Cys Ser Thr Pro Gly Val Thr Val Arg Leu Asp Gly Asp Glu
                100                 105                 110 aaa ggt tct tat gtg aca att aag tat tcc ttg act cca gca gga tcc        384
Lys Gly Ser Tyr Val Thr Ile Lys Tyr Ser Leu Thr Pro Ala Gly Ser
            115                 120                 125 ggt gga gct agc atg gga att att aat atc caa gat gaa att aat aat        432
Gly Gly Ala Ser Met Gly Ile Ile Asn Ile Gln Asp Glu Ile Asn Asn
        130                 135                 140 tac atg aaa gag gta tat ggt gca aca act gtt aaa agc aca tac gat        480
Tyr Met Lys Glu Val Tyr Gly Ala Thr Thr Val Lys Ser Thr Tyr Asp
145                 150                 155                 160 ccc tca ttc aaa gta ttt aat gaa tct gtg aca ccc caa ttc act gaa        528
Pro Ser Phe Lys Val Phe Asn Glu Ser Val Thr Pro Gln Phe Thr Glu
                165                 170                 175 att cca aca gaa cct gta aat aat caa tta act aca aaa aga gta gat        576
Ile Pro Thr Glu Pro Val Asn Asn Gln Leu Thr Thr Lys Arg Val Asp
                180                 185                 190 aat acg ggt agt tac cca gta gaa agt act gta tcg ttc aca tgg acg        624
Asn Thr Gly Ser Tyr Pro Val Glu Ser Thr Val Ser Phe Thr Trp Thr
            195                 200                 205 gaa acc cat aca gaa aca agt gca gta act gag gga gtg aaa gcc ggc        672
Glu Thr His Thr Glu Thr Ser Ala Val Thr Glu Gly Val Lys Ala Gly
        210                 215                 220 acc tca ata agt act aaa caa tct ttt aaa ttt ggt ttt gtt aac tct        720
Thr Ser Ile Ser Thr Lys Gln Ser Phe Lys Phe Gly Phe Val Asn Ser
225                 230                 235                 240 gat gtt act tta acg gta tca gca gaa tat aat tat agt aca aca aat        768
Asp Val Thr Leu Thr Val Ser Ala Glu Tyr Asn Tyr Ser Thr Thr Asn
                245                 250                 255 aca act aca aca aca gaa aca cac acc tgg tca gat tca aca aaa gta        816
Thr Thr Thr Thr Thr Glu Thr His Thr Trp Ser Asp Ser Thr Lys Val
                260                 265                 270 act att cct ccc aaa act tat gtg gag gct gca tac att atc caa aat        864
Thr Ile Pro Pro Lys Thr Tyr Val Glu Ala Ala Tyr Ile Ile Gln Asn
            275                 280                 285 gga aca tat aat gtt ccg gtt aat gta gaa tgt gat atg agt gga act        912
Gly Thr Tyr Asn Val Pro Val Asn Val Glu Cys Asp Met Ser Gly Thr
        290                 295                 300 tta ttt tgt aga ggg tat aga gat ggt gcg ctt att gca gca gtt tat        960
Leu Phe Cys Arg Gly Tyr Arg Asp Gly Ala Leu Ile Ala Ala Val Tyr
305                 310                 315                 320 gtt tct gta gcg gat tta gca gat tac aat cca aat tta aat ctt aca       1008
Val Ser Val Ala Asp Leu Ala Asp Tyr Asn Pro Asn Leu Asn Leu Thr
                325                 330                 335 aat aaa ggg gat gga att gct cac ttt aaa ggt tcg ggt ttt ata gag       1056
Asn Lys Gly Asp Gly Ile Ala His Phe Lys Gly Ser Gly Phe Ile Glu
                340                 345                 350 ggt gca caa ggc ttg cga agc att att cag gtt aca gaa tat cca cta       1104
Gly Ala Gln Gly Leu Arg Ser Ile Ile Gln Val Thr Glu Tyr Pro Leu
            355                 360                 365 gat gat aat aaa ggt cgc tcg aca cca ata act tat tta ata aat ggt       1152
Asp Asp Asn Lys Gly Arg Ser Thr Pro Ile Thr Tyr Leu Ile Asn Gly
        370                 375                 380 tca tta gca cca aat gtt aca tta aaa aat agc aac ata aaa ttt           1197
```

Ser Leu Ala Pro Asn Val Thr Leu Lys Asn Ser Asn Ile Lys Phe
385                 390                 395

<210> SEQ ID NO 20
<211> LENGTH: 399
<212> TYPE: PRT
<213> ORGANISM: Artificial sequence
<220> FEATURE:
<223> OTHER INFORMATION: Synthetic Construct

<400> SEQUENCE: 20

Met Thr Val Tyr Asn Ala Thr Phe Thr Ile Asn Phe Tyr Asn Glu Gly
1               5                   10                  15

Glu Trp Gly Gly Pro Glu Pro Tyr Gly Tyr Ile Lys Ala Tyr Leu Thr
            20                  25                  30

Asn Pro Asp His Asp Phe Glu Ile Trp Lys Gln Asp Trp Gly Lys
        35                  40                  45

Ser Thr Pro Glu Arg Ser Thr Tyr Thr Gln Thr Ile Lys Ile Ser Ser
50                  55                  60

Asp Thr Gly Ser Pro Ile Asn Gln Met Cys Phe Tyr Gly Asp Val Lys
65                  70                  75                  80

Glu Tyr Asp Val Gly Asn Ala Asp Asp Ile Leu Ala Tyr Pro Ser Gln
                85                  90                  95

Lys Val Cys Ser Thr Pro Gly Val Thr Val Arg Leu Asp Gly Asp Glu
            100                 105                 110

Lys Gly Ser Tyr Val Thr Ile Lys Tyr Ser Leu Thr Pro Ala Gly Ser
        115                 120                 125

Gly Gly Ala Ser Met Gly Ile Ile Asn Ile Gln Asp Glu Ile Asn Asn
    130                 135                 140

Tyr Met Lys Glu Val Tyr Gly Ala Thr Thr Val Lys Ser Thr Tyr Asp
145                 150                 155                 160

Pro Ser Phe Lys Val Phe Asn Glu Ser Val Thr Pro Gln Phe Thr Glu
                165                 170                 175

Ile Pro Thr Glu Pro Val Asn Asn Gln Leu Thr Thr Lys Arg Val Asp
            180                 185                 190

Asn Thr Gly Ser Tyr Pro Val Glu Ser Thr Val Ser Phe Thr Trp Thr
        195                 200                 205

Glu Thr His Thr Glu Thr Ser Ala Val Thr Glu Gly Val Lys Ala Gly
    210                 215                 220

Thr Ser Ile Ser Thr Lys Gln Ser Phe Lys Phe Gly Phe Val Asn Ser
225                 230                 235                 240

Asp Val Thr Leu Thr Val Ser Ala Glu Tyr Asn Tyr Ser Thr Thr Asn
                245                 250                 255

Thr Thr Thr Thr Thr Glu Thr His Thr Trp Ser Asp Ser Thr Lys Val
            260                 265                 270

Thr Ile Pro Pro Lys Thr Tyr Val Glu Ala Ala Tyr Ile Ile Gln Asn
        275                 280                 285

Gly Thr Tyr Asn Val Pro Val Asn Val Glu Cys Asp Met Ser Gly Thr
    290                 295                 300

Leu Phe Cys Arg Gly Tyr Arg Asp Gly Ala Leu Ile Ala Ala Val Tyr
305                 310                 315                 320

Val Ser Val Ala Asp Leu Ala Asp Tyr Asn Pro Asn Leu Asn Leu Thr
                325                 330                 335

Asn Lys Gly Asp Gly Ile Ala His Phe Lys Gly Ser Gly Phe Ile Glu
            340                 345                 350

```
Gly Ala Gln Gly Leu Arg Ser Ile Ile Gln Val Thr Glu Tyr Pro Leu
            355                 360                 365

Asp Asp Asn Lys Gly Arg Ser Thr Pro Ile Thr Tyr Leu Ile Asn Gly
        370                 375                 380

Ser Leu Ala Pro Asn Val Thr Leu Lys Asn Ser Asn Ile Lys Phe
385                 390                 395

<210> SEQ ID NO 21
<211> LENGTH: 1197
<212> TYPE: DNA
<213> ORGANISM: Artificial sequence
<220> FEATURE:
<223> OTHER INFORMATION: Recombinant fusion protein
<220> FEATURE:
<221> NAME/KEY: CDS
<222> LOCATION: (1)..(1197)
<223> OTHER INFORMATION: ET34-GSGGAS-ET33-plant

<400> SEQUENCE: 21 atg act gtg tac aat gct act ttc act atc aac ttt tac aat gaa ggt      48
Met Thr Val Tyr Asn Ala Thr Phe Thr Ile Asn Phe Tyr Asn Glu Gly
1               5                  10                  15 gaa tgg ggt ggt cct gaa cct tac ggt tac atc aag gca tac ctt act      96
Glu Trp Gly Gly Pro Glu Pro Tyr Gly Tyr Ile Lys Ala Tyr Leu Thr
            20                  25                  30 aat cct gat cat gat ttc gag att tgg aag caa gat gat tgg ggt aag     144
Asn Pro Asp His Asp Phe Glu Ile Trp Lys Gln Asp Asp Trp Gly Lys
        35                  40                  45 tct act cct gag agg tct act tac act caa act att aag ata tct tct     192
Ser Thr Pro Glu Arg Ser Thr Tyr Thr Gln Thr Ile Lys Ile Ser Ser
    50                  55                  60 gat act ggt tct cct atc aac cag atg tgc ttc tac ggt gac gtc aag     240
Asp Thr Gly Ser Pro Ile Asn Gln Met Cys Phe Tyr Gly Asp Val Lys
65                  70                  75                  80 gaa tac gat gtc ggc aac gct gat gat att ctt gct tac cct tct caa     288
Glu Tyr Asp Val Gly Asn Ala Asp Asp Ile Leu Ala Tyr Pro Ser Gln
                85                  90                  95 aag gtt tgc tct act cct ggt gtt act gtt agg ctt gat ggt gat gag     336
Lys Val Cys Ser Thr Pro Gly Val Thr Val Arg Leu Asp Gly Asp Glu
            100                 105                 110 aag ggt tct tac gtt act att aag tac tct ctt act cct gct gga tcc     384
Lys Gly Ser Tyr Val Thr Ile Lys Tyr Ser Leu Thr Pro Ala Gly Ser
        115                 120                 125 ggt gga gct agc atg ggt atc atc aac att caa gat gag att aac aat     432
Gly Gly Ala Ser Met Gly Ile Ile Asn Ile Gln Asp Glu Ile Asn Asn
    130                 135                 140 tac atg aag gaa gtt tac ggt gct act act gtt aag tct act tac gat     480
Tyr Met Lys Glu Val Tyr Gly Ala Thr Thr Val Lys Ser Thr Tyr Asp
145                 150                 155                 160 cct tct ttc aag gtt ttc aat gaa tct gtt act cct caa ttc act gaa     528
Pro Ser Phe Lys Val Phe Asn Glu Ser Val Thr Pro Gln Phe Thr Glu
                165                 170                 175 att cct act gaa cct gtc aac aac cag ctt act act aag agg gtc gac     576
Ile Pro Thr Glu Pro Val Asn Asn Gln Leu Thr Thr Lys Arg Val Asp
            180                 185                 190 aat act ggt tct tac cct gtt gaa tct act gtt tct tta act tgg act     624
Asn Thr Gly Ser Tyr Pro Val Glu Ser Thr Val Ser Leu Thr Trp Thr
        195                 200                 205 gaa act cat act gaa act tct gct gtt act gaa ggt gtt aag gct ggt     672
Glu Thr His Thr Glu Thr Ser Ala Val Thr Glu Gly Val Lys Ala Gly
    210                 215                 220
```

```
act tct att tct act aag caa tct ttc aag ttc ggt ttc gtg aac tct      720
Thr Ser Ile Ser Thr Lys Gln Ser Phe Lys Phe Gly Phe Val Asn Ser
225                 230                 235                 240 gat gtt act ctt act gtt tct gct gag tac aac tac tct act act aac      768
Asp Val Thr Leu Thr Val Ser Ala Glu Tyr Asn Tyr Ser Thr Thr Asn
                245                 250                 255 act act act act act gaa act cat act tgg tct gat tct act aag gtt      816
Thr Thr Thr Thr Thr Glu Thr His Thr Trp Ser Asp Ser Thr Lys Val
            260                 265                 270 act att cct cct aag act tac gtt gaa gct gct tac atc atc cag aat      864
Thr Ile Pro Pro Lys Thr Tyr Val Glu Ala Ala Tyr Ile Ile Gln Asn
        275                 280                 285 ggt act tac aat gtt cct gtt aat gtt gaa tgc gat atg tct ggt act      912
Gly Thr Tyr Asn Val Pro Val Asn Val Glu Cys Asp Met Ser Gly Thr
    290                 295                 300 ctg ttc tgt cga ggt tat cgt gat ggt gct ctt att gct gct gtt tac      960
Leu Phe Cys Arg Gly Tyr Arg Asp Gly Ala Leu Ile Ala Ala Val Tyr
305                 310                 315                 320 gtt tct gtt gct gat ctt gct gat tac aat cct aat ctt aat ctt act     1008
Val Ser Val Ala Asp Leu Ala Asp Tyr Asn Pro Asn Leu Asn Leu Thr
                325                 330                 335 aat aag ggt gat ggt att gct cat ttc aag ggt tct gga ttc att gaa     1056
Asn Lys Gly Asp Gly Ile Ala His Phe Lys Gly Ser Gly Phe Ile Glu
            340                 345                 350 ggt gct caa ggt ctt aga tct gtg atc caa gtt act gaa tac cct ctt     1104
Gly Ala Gln Gly Leu Arg Ser Val Ile Gln Val Thr Glu Tyr Pro Leu
        355                 360                 365 gat gat aat aag ggt agg tct act cct att acg tac ctt atc aac ggt     1152
Asp Asp Asn Lys Gly Arg Ser Thr Pro Ile Thr Tyr Leu Ile Asn Gly
    370                 375                 380 tct ctt gct cct aat gtt act ctt aag aat tct aat att aag ttc         1197
Ser Leu Ala Pro Asn Val Thr Leu Lys Asn Ser Asn Ile Lys Phe
385                 390                 395

<210> SEQ ID NO 22
<211> LENGTH: 399
<212> TYPE: PRT
<213> ORGANISM: Artificial sequence
<220> FEATURE:
<223> OTHER INFORMATION: Synthetic Construct

<400> SEQUENCE: 22

Met Thr Val Tyr Asn Ala Thr Phe Thr Ile Asn Phe Tyr Asn Glu Gly
1               5                   10                  15

Glu Trp Gly Gly Pro Glu Pro Tyr Gly Tyr Ile Lys Ala Tyr Leu Thr
            20                  25                  30

Asn Pro Asp His Asp Phe Glu Ile Trp Lys Gln Asp Asp Trp Gly Lys
        35                  40                  45

Ser Thr Pro Glu Arg Ser Thr Tyr Thr Gln Thr Ile Lys Ile Ser Ser
    50                  55                  60

Asp Thr Gly Ser Pro Ile Asn Gln Met Cys Phe Tyr Gly Asp Val Lys
65                  70                  75                  80

Glu Tyr Asp Val Gly Asn Ala Asp Ile Leu Ala Tyr Pro Ser Gln
            85                  90                  95

Lys Val Cys Ser Thr Pro Gly Val Thr Val Arg Leu Asp Gly Asp Glu
            100                 105                 110

Lys Gly Ser Tyr Val Thr Ile Lys Tyr Ser Leu Thr Pro Ala Gly Ser
        115                 120                 125

Gly Gly Ala Ser Met Gly Ile Ile Asn Ile Gln Asp Glu Ile Asn Asn
```

```
                130                 135                 140
Tyr Met Lys Glu Val Tyr Gly Ala Thr Thr Val Lys Ser Thr Tyr Asp
145                 150                 155                 160

Pro Ser Phe Lys Val Phe Asn Glu Ser Val Thr Pro Gln Phe Thr Glu
                165                 170                 175

Ile Pro Thr Glu Pro Val Asn Asn Gln Leu Thr Thr Lys Arg Val Asp
            180                 185                 190

Asn Thr Gly Ser Tyr Pro Val Glu Ser Thr Val Ser Leu Thr Trp Thr
        195                 200                 205

Glu Thr His Thr Glu Thr Ser Ala Val Thr Glu Gly Val Lys Ala Gly
    210                 215                 220

Thr Ser Ile Ser Thr Lys Gln Ser Phe Lys Phe Gly Phe Val Asn Ser
225                 230                 235                 240

Asp Val Thr Leu Thr Val Ser Ala Glu Tyr Asn Tyr Ser Thr Thr Asn
                245                 250                 255

Thr Thr Thr Thr Thr Glu Thr His Thr Trp Ser Asp Ser Thr Lys Val
            260                 265                 270

Thr Ile Pro Pro Lys Thr Tyr Val Glu Ala Ala Tyr Ile Ile Gln Asn
        275                 280                 285

Gly Thr Tyr Asn Val Pro Val Asn Val Glu Cys Asp Met Ser Gly Thr
    290                 295                 300

Leu Phe Cys Arg Gly Tyr Arg Asp Gly Ala Leu Ile Ala Ala Val Tyr
305                 310                 315                 320

Val Ser Val Ala Asp Leu Ala Asp Tyr Asn Pro Asn Leu Asn Leu Thr
                325                 330                 335

Asn Lys Gly Asp Gly Ile Ala His Phe Lys Gly Ser Gly Phe Ile Glu
            340                 345                 350

Gly Ala Gln Gly Leu Arg Ser Val Ile Gln Val Thr Glu Tyr Pro Leu
        355                 360                 365

Asp Asp Asn Lys Gly Arg Ser Thr Pro Ile Thr Tyr Leu Ile Asn Gly
    370                 375                 380

Ser Leu Ala Pro Asn Val Thr Leu Lys Asn Ser Asn Ile Lys Phe
385                 390                 395

<210> SEQ ID NO 23
<211> LENGTH: 801
<212> TYPE: DNA
<213> ORGANISM: Bacillus thuringiensis
<220> FEATURE:
<221> NAME/KEY: CDS
<222> LOCATION: (1)..(801)
<223> OTHER INFORMATION: ET33

<400> SEQUENCE: 23 atg gga att att aat atc caa gat gaa att aat aat tac atg aaa gag      48
Met Gly Ile Ile Asn Ile Gln Asp Glu Ile Asn Asn Tyr Met Lys Glu
1               5                   10                  15 gta tat ggt gca aca act gtt aaa agc aca tac gat ccc tca ttc aaa      96
Val Tyr Gly Ala Thr Thr Val Lys Ser Thr Tyr Asp Pro Ser Phe Lys
            20                  25                  30 gta ttt aat gaa tct gtg aca ccc caa ttc act gaa att cca aca gaa     144
Val Phe Asn Glu Ser Val Thr Pro Gln Phe Thr Glu Ile Pro Thr Glu
        35                  40                  45 cct gta aat aat caa tta act aca aaa aga gta gat aat acg ggt agt     192
Pro Val Asn Asn Gln Leu Thr Thr Lys Arg Val Asp Asn Thr Gly Ser
    50                  55                  60 tac cca gta gaa agt act gta tcg ttc aca tgg acg gaa acc cat aca     240
```

-continued

| | | |
|---|---|---|
| Tyr Pro Val Glu Ser Thr Val Ser Phe Thr Trp Thr Glu Thr His Thr<br>65                          70                     75                   80 | | |
| gaa aca agt gca gta act gag gga gtg aaa gcc ggc acc tca ata agt<br>Glu Thr Ser Ala Val Thr Glu Gly Val Lys Ala Gly Thr Ser Ile Ser<br>                        85                     90                       95 | 288 | |
| act aaa caa tct ttt aaa ttt ggt ttt gtt aac tct gat gtt act tta<br>Thr Lys Gln Ser Phe Lys Phe Gly Phe Val Asn Ser Asp Val Thr Leu<br>                      100                   105                 110 | 336 | |
| acg gta tca gca gaa tat aat tat agt aca aca aat aca act aca aca<br>Thr Val Ser Ala Glu Tyr Asn Tyr Ser Thr Thr Asn Thr Thr Thr Thr<br>             115                   120                 125 | 384 | |
| aca gaa aca cac acc tgg tca gat tca aca aaa gta act att cct ccc<br>Thr Glu Thr His Thr Trp Ser Asp Ser Thr Lys Val Thr Ile Pro Pro<br>    130                   135                 140 | 432 | |
| aaa act tat gtg gag gct gca tac att atc caa aat gga aca tat aat<br>Lys Thr Tyr Val Glu Ala Ala Tyr Ile Ile Gln Asn Gly Thr Tyr Asn<br>145                       150                 155                 160 | 480 | |
| gtt ccg gtt aat gta gaa tgt gat atg agt gga act tta ttt tgt aga<br>Val Pro Val Asn Val Glu Cys Asp Met Ser Gly Thr Leu Phe Cys Arg<br>                     165                   170               175 | 528 | |
| ggg tat aga gat ggt gcg ctt att gca gca gtt tat gtt tct gta gcg<br>Gly Tyr Arg Asp Gly Ala Leu Ile Ala Ala Val Tyr Val Ser Val Ala<br>             180                   185                 190 | 576 | |
| gat tta gca gat tac aat cca aat tta aat ctt aca aat aaa ggg gat<br>Asp Leu Ala Asp Tyr Asn Pro Asn Leu Asn Leu Thr Asn Lys Gly Asp<br>           195                  200                 205 | 624 | |
| gga att gct cac ttt aaa ggt tcg ggt ttt ata gag ggt gca caa ggc<br>Gly Ile Ala His Phe Lys Gly Ser Gly Phe Ile Glu Gly Ala Gln Gly<br>    210                   215                 220 | 672 | |
| ttg cga agc att att cag gtt aca gaa tat cca cta gat gat aat aaa<br>Leu Arg Ser Ile Ile Gln Val Thr Glu Tyr Pro Leu Asp Asp Asn Lys<br>225                       230                 235                 240 | 720 | |
| ggt cgc tcg aca cca ata act tat tta ata aat ggt tca tta gca cca<br>Gly Arg Ser Thr Pro Ile Thr Tyr Leu Ile Asn Gly Ser Leu Ala Pro<br>             245                   250                 255 | 768 | |
| aat gtt aca tta aaa aat agc aac ata aaa ttt<br>Asn Val Thr Leu Lys Asn Ser Asn Ile Lys Phe<br>    260                   265 | 801 | |

```
<210> SEQ ID NO 24
<211> LENGTH: 267
<212> TYPE: PRT
<213> ORGANISM: Bacillus thuringiensis

<400> SEQUENCE: 24
```

Met Gly Ile Ile Asn Ile Gln Asp Glu Ile Asn Asn Tyr Met Lys Glu
1                   5                     10                   15

Val Tyr Gly Ala Thr Thr Val Lys Ser Thr Tyr Asp Pro Ser Phe Lys
                    20                     25                     30

Val Phe Asn Glu Ser Val Thr Pro Gln Phe Thr Glu Ile Pro Thr Glu
                  35                     40                   45

Pro Val Asn Asn Gln Leu Thr Thr Lys Arg Val Asp Asn Thr Gly Ser
    50                     55                     60

Tyr Pro Val Glu Ser Thr Val Ser Phe Thr Trp Thr Glu Thr His Thr
65                          70                     75                   80

Glu Thr Ser Ala Val Thr Glu Gly Val Lys Ala Gly Thr Ser Ile Ser
                    85                     90                   95

Thr Lys Gln Ser Phe Lys Phe Gly Phe Val Asn Ser Asp Val Thr Leu
                  100                  105                110

```
Thr Val Ser Ala Glu Tyr Asn Tyr Ser Thr Thr Asn Thr Thr Thr
            115                 120                 125

Thr Glu Thr His Thr Trp Ser Asp Ser Thr Lys Val Thr Ile Pro Pro
    130                 135                 140

Lys Thr Tyr Val Glu Ala Ala Tyr Ile Ile Gln Asn Gly Thr Tyr Asn
145                 150                 155                 160

Val Pro Val Asn Val Glu Cys Asp Met Ser Gly Thr Leu Phe Cys Arg
                165                 170                 175

Gly Tyr Arg Asp Gly Ala Leu Ile Ala Ala Val Tyr Val Ser Val Ala
            180                 185                 190

Asp Leu Ala Asp Tyr Asn Pro Asn Leu Asn Leu Thr Asn Lys Gly Asp
        195                 200                 205

Gly Ile Ala His Phe Lys Gly Ser Gly Phe Ile Glu Gly Ala Gln Gly
    210                 215                 220

Leu Arg Ser Ile Ile Gln Val Thr Glu Tyr Pro Leu Asp Asp Asn Lys
225                 230                 235                 240

Gly Arg Ser Thr Pro Ile Thr Tyr Leu Ile Asn Gly Ser Leu Ala Pro
                245                 250                 255

Asn Val Thr Leu Lys Asn Ser Asn Ile Lys Phe
            260                 265

<210> SEQ ID NO 25
<211> LENGTH: 381
<212> TYPE: DNA
<213> ORGANISM: Bacillus thuringiensis
<220> FEATURE:
<221> NAME/KEY: CDS
<222> LOCATION: (1)..(381)
<223> OTHER INFORMATION: ET34

<400> SEQUENCE: 25 atg aca gta tat aac gca act ttc acc att aat ttc tat aat gaa gga      48
Met Thr Val Tyr Asn Ala Thr Phe Thr Ile Asn Phe Tyr Asn Glu Gly
1               5                   10                  15 gaa tgg ggg ggg cca gaa cca tat ggt tat ata aaa gca tat ctt aca      96
Glu Trp Gly Gly Pro Glu Pro Tyr Gly Tyr Ile Lys Ala Tyr Leu Thr
                20                  25                  30 aat cca gat cat gat ttt gaa att tgg aaa caa gat gat tgg ggg aaa     144
Asn Pro Asp His Asp Phe Glu Ile Trp Lys Gln Asp Asp Trp Gly Lys
            35                  40                  45 agt act cct gag aga agt act tat acg caa acg att aaa ata agt agc     192
Ser Thr Pro Glu Arg Ser Thr Tyr Thr Gln Thr Ile Lys Ile Ser Ser
        50                  55                  60 gac act ggt tcc cct ata aac caa atg tgt ttt tat ggt gat gtg aaa     240
Asp Thr Gly Ser Pro Ile Asn Gln Met Cys Phe Tyr Gly Asp Val Lys
65                  70                  75                  80 gaa tac gac gta gga aat gca gat gat att ctc gct tat cca agt caa     288
Glu Tyr Asp Val Gly Asn Ala Asp Asp Ile Leu Ala Tyr Pro Ser Gln
                85                  90                  95 aaa gta tgc agt aca cct ggt gta aca gta cga ctt gat ggc gat gag     336
Lys Val Cys Ser Thr Pro Gly Val Thr Val Arg Leu Asp Gly Asp Glu
            100                 105                 110 aaa ggt tct tat gtg aca att aag tat tcc ttg act cca gca taa         381
Lys Gly Ser Tyr Val Thr Ile Lys Tyr Ser Leu Thr Pro Ala
        115                 120                 125

<210> SEQ ID NO 26
<211> LENGTH: 126
<212> TYPE: PRT
```

<213> ORGANISM: Bacillus thuringiensis

<400> SEQUENCE: 26

```
Met Thr Val Tyr Asn Ala Thr Phe Thr Ile Asn Phe Tyr Asn Glu Gly
1               5                   10                  15

Glu Trp Gly Gly Pro Glu Pro Tyr Gly Tyr Ile Lys Ala Tyr Leu Thr
            20                  25                  30

Asn Pro Asp His Asp Phe Glu Ile Trp Lys Gln Asp Asp Trp Gly Lys
        35                  40                  45

Ser Thr Pro Glu Arg Ser Thr Tyr Thr Gln Thr Ile Lys Ile Ser Ser
    50                  55                  60

Asp Thr Gly Ser Pro Ile Asn Gln Met Cys Phe Tyr Gly Asp Val Lys
65                  70                  75                  80

Glu Tyr Asp Val Gly Asn Ala Asp Asp Ile Leu Ala Tyr Pro Ser Gln
                85                  90                  95

Lys Val Cys Ser Thr Pro Gly Val Thr Val Arg Leu Asp Gly Asp Glu
            100                 105                 110

Lys Gly Ser Tyr Val Thr Ile Lys Tyr Ser Leu Thr Pro Ala
        115                 120                 125
```

<210> SEQ ID NO 27
<211> LENGTH: 805
<212> TYPE: DNA
<213> ORGANISM: Bacillus thuringiensis
<220> FEATURE:
<221> NAME/KEY: DNA
<222> LOCATION: (1)..(805)
<223> OTHER INFORMATION: Cryptic tIC100, frameshift at position 84

<400> SEQUENCE: 27

```
atgggaatta tcaacattca agacgaaatt aatgactaca tgaaaggtat gtatggtgca     60
acatctgtta aaagcactta tgaccccctc attcaaagta tttaacgaat ctgtgacacc    120
tcaatatgat gtgattccaa cagaacctgt aaataatcat attactacta agtaataga    180
taatccaggg acttcagaag taaccagtac agtaacgttc acatggacgg aaaccgacac    240
tgtaacctct gcagtgacta aagggtataa agtcggtggt tcagtaagct caaaagcaac    300
ttttaaattt gcttttgtta cttctgatgt tactgtaact gtatcagcag aatataatta    360
tagtacaaca gaaacaacaa caaaaacaga tacacgcaca tggacggatt cgacgacagt    420
aaaagcccct ccaagaacta atgtagaagt tgcatatatt atccaaactg gaaattataa    480
cgttccggtt aatgtagagt ctgatatgac tggaacgcta ttttgcagag ggtatagaga    540
tggtgcacta attgcagcgg cttatgtttc tataacagat ttagcagatt acaatcctaa    600
tttgggtctt acaaatgaag ggaatggggt tgctcatttt aaaggtgaag ttatataga    660
gggtgcgcaa ggcttaagaa gctacattca agttacagaa tatccagtgg atgataatgg    720
cagacattcg ataccaaaaa cttatataat taaaggttca ttagcaccca atgttacttt    780
aataaatgat agaaaggaag gtaga                                         805
```

<210> SEQ ID NO 28
<211> LENGTH: 33
<212> TYPE: DNA
<213> ORGANISM: Artificial sequence
<220> FEATURE:
<223> OTHER INFORMATION: Synthetic oligonucleotide
<220> FEATURE:
<221> NAME/KEY: DNA
<222> LOCATION: (1)..(33)
<223> OTHER INFORMATION: Mutagenesis primer for tIC100 - reverse -continued

```
            sequence

<400> SEQUENCE: 28
cgttaaatac tttgaatgag gggtcataag tgc                            33

<210> SEQ ID NO 29
<211> LENGTH: 33
<212> TYPE: DNA
<213> ORGANISM: Artificial sequence
<220> FEATURE:
<223> OTHER INFORMATION: Synthetic oligonucleotide
<220> FEATURE:
<221> NAME/KEY: DNA
<222> LOCATION: (1)..(33)
<223> OTHER INFORMATION: Mutagenesis primer for tIC100 - forward
      sequence

<400> SEQUENCE: 29
gcacttatga cccctcattc aaagtattta acg                            33

<210> SEQ ID NO 30
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: DNA
<222> LOCATION: (1)..(21)
<223> OTHER INFORMATION: Pst oligo

<400> SEQUENCE: 30
aaaatgagca accccattcc c                                         21

<210> SEQ ID NO 31
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: DNA
<222> LOCATION: (1)..(21)
<223> OTHER INFORMATION: EcoRI oligo

<400> SEQUENCE: 31
attattttga attcttttat c                                         21

<210> SEQ ID NO 32
<211> LENGTH: 1200
<212> TYPE: DNA
<213> ORGANISM: Artificial sequence
<220> FEATURE:
<223> OTHER INFORMATION: Recombinant fusion protein
<220> FEATURE:
<221> NAME/KEY: CDS
<222> LOCATION: (1)..(1200)
<223> OTHER INFORMATION: tIC101-GSGGAS-tIC100 fusion peptide

<400> SEQUENCE: 32 atg aca gta tat aac gta act ttt acc att aaa ttc tat aat gaa ggt      48
Met Thr Val Tyr Asn Val Thr Phe Thr Ile Lys Phe Tyr Asn Glu Gly
1               5                   10                  15 gaa tgg ggg ggg cca gaa cct tac ggt aag ata tat gca tac ctt caa      96
Glu Trp Gly Gly Pro Glu Pro Tyr Gly Lys Ile Tyr Ala Tyr Leu Gln
            20                  25                  30 aat cca gat cat aat ttc gaa att tgg tca caa gat aat tgg ggg aag     144
Asn Pro Asp His Asn Phe Glu Ile Trp Ser Gln Asp Asn Trp Gly Lys
```

```
                 35                  40                  45
gat acg cct gag aaa agt tct cac act caa aca att aaa ata agt agc    192
Asp Thr Pro Glu Lys Ser Ser His Thr Gln Thr Ile Lys Ile Ser Ser
     50                  55                  60 cca aca ggg ggg cct ata aac caa atg tgt ttt tat ggt gat gta aaa    240
Pro Thr Gly Gly Pro Ile Asn Gln Met Cys Phe Tyr Gly Asp Val Lys
 65                  70                  75                  80 gaa tac gac gta gga aat gca gat gat gtt ctc gcc tat cca agt caa    288
Glu Tyr Asp Val Gly Asn Ala Asp Asp Val Leu Ala Tyr Pro Ser Gln
                 85                  90                  95 aaa gta tgc agt acg cct ggc aca aca ata agg ctt aac gga gat gag    336
Lys Val Cys Ser Thr Pro Gly Thr Thr Ile Arg Leu Asn Gly Asp Glu
            100                 105                 110 aaa ggt tct tat ata cag att aga tat tcc ttg gcc cca gct gga tcc    384
Lys Gly Ser Tyr Ile Gln Ile Arg Tyr Ser Leu Ala Pro Ala Gly Ser
            115                 120                 125 ggt gga gct agc atg gga att atc aac att caa gac gaa att aat gac    432
Gly Gly Ala Ser Met Gly Ile Ile Asn Ile Gln Asp Glu Ile Asn Asp
        130                 135                 140 tac atg aaa ggt atg tat ggt gca aca tct gtt aaa agc act tat gac    480
Tyr Met Lys Gly Met Tyr Gly Ala Thr Ser Val Lys Ser Thr Tyr Asp
145                 150                 155                 160 ccc tca ttc aaa gta ttt aac gaa tct gtg aca cct caa tat gat gtg    528
Pro Ser Phe Lys Val Phe Asn Glu Ser Val Thr Pro Gln Tyr Asp Val
                165                 170                 175 att cca aca gaa cct gta aat aat cat att act act aaa gta ata gat    576
Ile Pro Thr Glu Pro Val Asn Asn His Ile Thr Thr Lys Val Ile Asp
            180                 185                 190 aat cca ggg act tca gaa gta acc agt aca gta acg ttc aca tgg acg    624
Asn Pro Gly Thr Ser Glu Val Thr Ser Thr Val Thr Phe Thr Trp Thr
            195                 200                 205 gaa acc gac act gta acc tct gca gtg act aaa ggg tat aaa gtc ggt    672
Glu Thr Asp Thr Val Thr Ser Ala Val Thr Lys Gly Tyr Lys Val Gly
        210                 215                 220 ggt tca gta agc tca aaa gca act ttt aaa ttt gct ttt gtt act tct    720
Gly Ser Val Ser Ser Lys Ala Thr Phe Lys Phe Ala Phe Val Thr Ser
225                 230                 235                 240 gat gtt act gta act gta tca gca gaa tat aat tat agt aca aca gaa    768
Asp Val Thr Val Thr Val Ser Ala Glu Tyr Asn Tyr Ser Thr Thr Glu
                245                 250                 255 aca aca aca aaa aca gat aca cgc aca tgg acg gat tcg acg aca gta    816
Thr Thr Thr Lys Thr Asp Thr Arg Thr Trp Thr Asp Ser Thr Thr Val
            260                 265                 270 aaa gcc cct cca aga act aat gta gaa gtt gca tat att atc caa act    864
Lys Ala Pro Pro Arg Thr Asn Val Glu Val Ala Tyr Ile Ile Gln Thr
        275                 280                 285 gga aat tat aac gtt ccg gtt aat gta gag tct gat atg act gga acg    912
Gly Asn Tyr Asn Val Pro Val Asn Val Glu Ser Asp Met Thr Gly Thr
290                 295                 300 cta ttt tgc aga ggg tat aga gat ggt gca cta att gca gcg gct tat    960
Leu Phe Cys Arg Gly Tyr Arg Asp Gly Ala Leu Ile Ala Ala Ala Tyr
305                 310                 315                 320 gtt tct ata aca gat tta gca gat tac aat cct aat ttg ggt ctt aca   1008
Val Ser Ile Thr Asp Leu Ala Asp Tyr Asn Pro Asn Leu Gly Leu Thr
                325                 330                 335 aat gaa ggg aat ggg gtt gct cat ttt aaa ggt gaa ggt tat ata gag   1056
Asn Glu Gly Asn Gly Val Ala His Phe Lys Gly Glu Gly Tyr Ile Glu
            340                 345                 350 ggt gcg caa ggc tta aga agc tac att caa gtt aca gaa tat cca gtg   1104
Gly Ala Gln Gly Leu Arg Ser Tyr Ile Gln Val Thr Glu Tyr Pro Val
```

```
Gly Ala Gln Gly Leu Arg Ser Tyr Ile Gln Val Thr Glu Tyr Pro Val
            355                 360                 365 gat gat aat ggc aga cat tcg ata cca aaa act tat ata att aaa ggt      1152
Asp Asp Asn Gly Arg His Ser Ile Pro Lys Thr Tyr Ile Ile Lys Gly
        370                 375                 380 tca tta gca ccc aat gtt act tta ata aat gat aga aag gaa ggt aga      1200
Ser Leu Ala Pro Asn Val Thr Leu Ile Asn Asp Arg Lys Glu Gly Arg
385                 390                 395                 400

<210> SEQ ID NO 33
<211> LENGTH: 400
<212> TYPE: PRT
<213> ORGANISM: Artificial sequence
<220> FEATURE:
<223> OTHER INFORMATION: Synthetic Construct

<400> SEQUENCE: 33

Met Thr Val Tyr Asn Val Thr Phe Thr Ile Lys Phe Tyr Asn Glu Gly
1               5                   10                  15

Glu Trp Gly Gly Pro Glu Pro Tyr Gly Lys Ile Tyr Ala Tyr Leu Gln
            20                  25                  30

Asn Pro Asp His Asn Phe Glu Ile Trp Ser Gln Asp Asn Trp Gly Lys
        35                  40                  45

Asp Thr Pro Glu Lys Ser Ser His Thr Gln Thr Ile Lys Ile Ser Ser
    50                  55                  60

Pro Thr Gly Gly Pro Ile Asn Gln Met Cys Phe Tyr Gly Asp Val Lys
65                  70                  75                  80

Glu Tyr Asp Val Gly Asn Ala Asp Val Leu Ala Tyr Pro Ser Gln
                85                  90                  95

Lys Val Cys Ser Thr Pro Gly Thr Thr Ile Arg Leu Asn Gly Asp Glu
            100                 105                 110

Lys Gly Ser Tyr Ile Gln Ile Arg Tyr Ser Leu Ala Pro Ala Gly Ser
        115                 120                 125

Gly Gly Ala Ser Met Gly Ile Ile Asn Ile Gln Asp Glu Ile Asn Asp
    130                 135                 140

Tyr Met Lys Gly Met Tyr Gly Ala Thr Ser Val Lys Ser Thr Tyr Asp
145                 150                 155                 160

Pro Ser Phe Lys Val Phe Asn Glu Ser Val Thr Pro Gln Tyr Asp Val
                165                 170                 175

Ile Pro Thr Glu Pro Val Asn Asn His Ile Thr Thr Lys Val Ile Asp
            180                 185                 190

Asn Pro Gly Thr Ser Glu Val Thr Ser Thr Val Thr Phe Thr Trp Thr
        195                 200                 205

Glu Thr Asp Thr Val Thr Ser Ala Val Thr Lys Gly Tyr Lys Val Gly
    210                 215                 220

Gly Ser Val Ser Ser Lys Ala Thr Phe Lys Phe Ala Phe Val Thr Ser
225                 230                 235                 240

Asp Val Thr Val Thr Val Ser Ala Glu Tyr Asn Tyr Ser Thr Thr Glu
                245                 250                 255

Thr Thr Thr Lys Thr Asp Thr Arg Thr Trp Thr Asp Ser Thr Thr Val
            260                 265                 270

Lys Ala Pro Pro Arg Thr Asn Val Glu Val Ala Tyr Ile Ile Gln Thr
        275                 280                 285

Gly Asn Tyr Asn Val Pro Val Asn Val Glu Ser Asp Met Thr Gly Thr
    290                 295                 300

Leu Phe Cys Arg Gly Tyr Arg Asp Gly Ala Leu Ile Ala Ala Ala Tyr
```

```
305                 310                 315                 320
Val Ser Ile Thr Asp Leu Ala Asp Tyr Asn Pro Asn Leu Gly Leu Thr
                325                 330                 335

Asn Glu Gly Asn Gly Val Ala His Phe Lys Gly Glu Gly Tyr Ile Glu
            340                 345                 350

Gly Ala Gln Gly Leu Arg Ser Tyr Ile Gln Val Thr Glu Tyr Pro Val
            355                 360                 365

Asp Asp Asn Gly Arg His Ser Ile Pro Lys Thr Tyr Ile Ile Lys Gly
        370                 375                 380

Ser Leu Ala Pro Asn Val Thr Leu Ile Asn Asp Arg Lys Glu Gly Arg
385                 390                 395                 400

<210> SEQ ID NO 34
<211> LENGTH: 6
<212> TYPE: PRT
<213> ORGANISM: Artificial sequence
<220> FEATURE:
<223> OTHER INFORMATION: GSGGAS linker sequence

<400> SEQUENCE: 34

Gly Ser Gly Gly Ala Ser
1               5

<210> SEQ ID NO 35
<211> LENGTH: 16
<212> TYPE: PRT
<213> ORGANISM: Artificial sequence
<220> FEATURE:
<223> OTHER INFORMATION: (GGGS)3 linker sequence

<400> SEQUENCE: 35

Gly Ser Gly Gly Gly Ser Gly Gly Gly Ser Gly Gly Gly Ser Ala Ser
1               5                   10                  15

<210> SEQ ID NO 36
<211> LENGTH: 16
<212> TYPE: PRT
<213> ORGANISM: Artificial sequence
<220> FEATURE:
<223> OTHER INFORMATION: lysine oxidase linker sequence

<400> SEQUENCE: 36

Pro Ala Leu Leu Lys Glu Ala Pro Arg Ala Glu Glu Glu Leu Pro Pro
1               5                   10                  15
```

The invention claimed is:

1. An isolated polynucleotide sequence encoding an insecticidal polypeptide combination comprising SEQ ID NO:2 and SEQ ID NO:4.

2. A polynucleotide sequence which hybridizes under stringent conditions of from about 0.02M NaCl to about 1.5M NaCl at temperatures of from about 50° C. to about 70° C. to a complement of the polynucleotide sequence of claim 1 and encodes a polypeptide comprising SEQ ID NO:2 and SEQ ID NO:4.

3. The polynucleotide sequence of claim 1, wherein said polypeptide combination further comprises SEQ ID NO:14.

4. The polynucleotide sequence of claim 1, wherein said polypeptide combination comprises a fusion of SEQ ID NO:2 and SEQ ID NO:4.

5. The polynucleotide sequence of claim 4, wherein said SEQ ID NO:2 and SEQ ID NO:4 are fused using a linker sequence.

6. The polynucleotide sequence of claim 5, wherein said polypeptide combination comprises SEQ ID NO:6, SEQ ID NO:8, SEQ ID NO:10 or SEQ ID NO:33.

7. The polynucleotide sequence of claim 1 comprising SEQ ID NO:1 and SEQ ID NO:3.

8. A vector for use in transforming a host cell, wherein said vector comprises the polynucleotide sequence of claim 1.

9. The vector of claim 8, wherein said host cell is selected from the group consisting of a plant cell and a bacterial cell.

10. A plant tissue transformed with the polynucleotide sequence of claim 1.

11. A method for protecting a cotton plant from boll weevil infestation, said method comprising providing to a boll weevil in its diet the plant tissue of claim 10.

12. The plant tissue of claim 10, wherein said tissue comprises said polypeptide combination present in a Coleopteran insect inhibitory effective amount.

13. The plant tissue of claim 10, wherein said tissue is selected from the group consisting of a plant cell, an embryonic plant tissue, plant calli, a leaf, a plant stem, a plant root, a plant flower, a fruit, a fruiting body, a boll, and a plant seed.

14. A plant regenerated from the plant tissue of claim 10.

15. The plant of claim 14, wherein said plant comprises said polypeptide combination present in a Coleopteran insect inhibitory effective amount.

16. The plant of claim 14, wherein said plant is selected from the group consisting of corn, wheat, cotton, soybean, oat, rice, rye, sorghum, sugarcane, tomato, tobacco, kapok, flax, potato, barley, turf grass, pasture grass, berry bush, fruit tree, legume, vegetable, ornamental plant, shrub, cactus, succulent, deciduous tree, and evergreen tree.

17. A method for protecting a cotton plant from boll weevil infestation, said method comprising providing to a boll weevil in its diet the plant of claim 14.

18. A method of making a transgenic plant resistant to Coleopteran insect infestation, said method comprising the steps of:
   a) incorporating into a genome of a plant cell the polynucleotide sequence of claim 1;
   b) isolating and propagating a plant cell transformed with said polynucleotide sequence;
   c) regenerating a plant from said plant cell transformed with said polynucleotide sequence; and
   d) propagating said plant; wherein said plant expresses an insecticidally effective amount of said polypeptide combination.

19. The method of claim 18, wherein said plant cell is either a monocot or a dicot plant cell.

20. The method of claim 19, wherein said monocot plant cell is selected from the group consisting of corn, wheat, rye, barley, rice, banana, sugarcane, oat, flax, turf grass, pasture grass, and sorghum cells.

21. The method of claim 19, wherein said dicot plant cell is selected from the group consisting of cotton, soybean, canola, potato, tomato, fruit tree, shrub, vegetable, and berry cells.

22. A plant cell transformed with the polynucleotide sequence of claim 1.

23. The plant cell of claim 22, wherein said cell produces an amount of said polypeptide combination effective for controlling a Coleopteran insect pest infestation.

24. A method of making a host cell resistant to Coleopteran insect pest infestation comprising the steps of:
   a) transforming said host cell with the polynucleotide sequence of claim 1; and
   b) selecting a host cell expressing said polypeptide combination.

25. The method of claim 24, wherein said Coleopteran insect pest is a cotton boll weevil and said host cell is a cotton plant cell.

* * * * *